(12) United States Patent
Trono et al.

(10) Patent No.: US 8,338,168 B2
(45) Date of Patent: Dec. 25, 2012

(54) CHIMERIC GLYCOPROTEINS AND PSEUDOTYPED LENTIVIRAL VECTORS

(75) Inventors: Didier Trono, Collonge (CH); Francois-Loic Cosset, Lyons (FR); Virginie Sandrin, Lyons (FR); Bertrand Boson, Lyons (FR); Didier Negre, Lyons (FR); Patrick Salmon, Arenthon (FR)

(73) Assignees: Institut National de la Sante et de la Recherche Medicale (INSERM), Paris (FR); Institut Clayton de la Recherche, Geneva (CH)

( * ) Notice: Subject to any disclaimer, the term of this patent is extended or adjusted under 35 U.S.C. 154(b) by 1237 days.

(21) Appl. No.: 10/512,474

(22) PCT Filed: Apr. 25, 2003

(86) PCT No.: PCT/IB03/01597
§ 371 (c)(1),
(2), (4) Date: Mar. 9, 2006

(87) PCT Pub. No.: WO03/091442
PCT Pub. Date: Nov. 6, 2003

(65) Prior Publication Data
US 2006/0257366 A1   Nov. 16, 2006

Related U.S. Application Data

(60) Provisional application No. 60/375,654, filed on Apr. 26, 2002.

(51) Int. Cl.
*C12N 15/00* (2006.01)
*C12N 15/64* (2006.01)

(52) U.S. Cl. ................ 435/320.1; 435/325; 435/91.4

(58) Field of Classification Search ............. 435/320.1, 435/325, 91.4
See application file for complete search history.

(56) References Cited

U.S. PATENT DOCUMENTS

| | | | |
|---|---|---|---|
| 4,682,195 A | 7/1987 | Yilmaz |
| 4,683,202 A | 7/1987 | Mullis |
| 5,466,468 A | 11/1995 | Schneider et al. |
| 5,645,897 A | 7/1997 | Andra |
| 5,686,279 A | 11/1997 | Finer et al. |
| 5,705,629 A | 1/1998 | Bhongle |
| 5,846,225 A | 12/1998 | Rosengart et al. |
| 5,846,233 A | 12/1998 | Lilley et al. |
| 5,925,565 A | 7/1999 | Berlioz et al. |
| 5,928,906 A | 7/1999 | Koster et al. |
| 5,935,819 A | 8/1999 | Eichner et al. |
| 5,994,136 A | 11/1999 | Naldini et al. |
| 6,013,516 A | 1/2000 | Verma et al. |
| 6,136,597 A | 10/2000 | Hope et al. |
| 2001/0051375 A1* | 12/2001 | Kelly et al. .............. 435/456 |

FOREIGN PATENT DOCUMENTS
EP   266 032   5/1988

OTHER PUBLICATIONS

Christodoulopoulos et al, (Journal of Virology, 75(9): 4129-4138, 2001).*
Stitz et al, (Virology, 273: 16-20, 2000).*
Gladow et al (J Gene Med, 2(6): 409-15, 2000).*
Mangeot et al (Journal of Virology, 74(8): 8307-8315, 2000).*
Rasko et al (Proc. Natl. Acad. Sci, 96: 2129-2134, 1999).*
Salmon et al, "A chimeric galv-derived envelop glycoprotein harboring the cytoplasmic tail of MLV envelope efficiently pseudotypes HIV-1 vectors", 2000, p. 23, vol. 2sup., Journal of Gene Medicine.
Christodoulopoulos et al, "Sequences in the Cytoplasmic Tail of the Gibbon Ape Leukemia Virus Envelope Protein That Prevent Its Incorporation Into Lentivirus Vectors", May 2001, pp. 4129-4138, vol. 75, No. 9, Journal of Virology.
Negre et al, "Lentiviral vectors derived from simian immunodeficiency virus", Sep. 2001, pp. 53-74, vol. 261, Current Topics in Microbiology and Immunology.
Stitz et al, Lentiviral Vectors Pseudotyped with Envelope Glycoproteins Derived from Gibbon Ape Leukemia Virus and Murine Leukemia Virus 10A1:, Jul. 20, 2000, pp. 16-20, vol. 273, No. 1, Virology, Academic Press, Orlando, US.
Sandrin et al, "Lentiviral vectors pseudotyped with a modified RD114 enveloope glycoprotein show increased stability in sera and augmented transduction of primary lymphocytes and CD34+ cells derived from human and nonhuman primates", Aug. 1, 2002, pp. 823-832, vol. 100, No. 3, Blood, United States.
Kelly et al, "RD114-Pseudotyped oncoretroviral vectors: Biological and physical properties", Jun. 2001, pp. 262-277, vol. 938, Annals of the New York Academy of Sciences.
Negre et al, "Characterization of novel safe lentiviral vectors derived from that efficiently transducer mature human dendritic cells", Oct. 2000, pp. 1613-1623, vol. 7, No. 9, Gene Therapy, England.

* cited by examiner

*Primary Examiner* — Gerald Leffers, Jr.
*Assistant Examiner* — Magdalene Sgagias
(74) *Attorney, Agent, or Firm* — B. Aaron Schulman, Esq.; Stites & Harbison PLLC

(57) ABSTRACT

The present invention provides improved chimeric glycoproteins (GPs) and improved lentiviral vectors pseudotyped with those glycoproteins. Also provided are methods and compositions for making such glycoproteins and vectors, and improved methods of in vitro and in vivo transduction of cells with such vectors. Improved chimeric GPs encode the extracellular and transmembrane domains of GALV or RD114 GPs fused to the cytoplasmic tail of MLV-A GP. Vectors pseudotyped with these GAL V/TR and RD 114/TR GP chimeras have significantly higher titers than vectors coated with the parental GPs. Additionally, RD114/TR-pseudotyped vectors are efficiently concentrated and are resistant to inactivation induced by the complement of both human and macaque sera. RD114 GP-pseudotyped lentiviral vectors have particular utility for in vivo gene transfer applications.

15 Claims, 12 Drawing Sheets

FIG. 2

FIG. 7

CHIMERIC GLYCOPROTEINS AND PSEUDOTYPED LENTIVIRAL VECTORS

This application claims benefit of U.S. Provisional Application No. 60/375,654, filed Apr. 26, 2002.

BACKGROUND OF THE INVENTION

1. Field of the Invention

The present invention relates to chimeric glycoproteins and improved lentiviral vectors pseudotyped with those glycoproteins, methods and compositions for making such glycoproteins and vectors, and methods of in vitro and in vivo transduction of cells with such vectors. The improved compositions and vectors are of particular utility for in vivo gene transfer applications.

2. Description of Related Art

Vectors derived from retroviruses offer particularly flexible properties in gene transfer applications given the numerous possible associations of various viral surface glycoproteins (determining cell tropism) with different types of viral cores (determining genome replication and integration)[1]. For example, association of the VSV-G glycoprotein with viral cores derived from lentiviruses results in vector pseudotypes that have broad tropism and can integrate into non-proliferating target cells[2]. They have proved useful for the transduction of several cell types ex vivo and in vivo[3-7]. Yet there is considerable interest in exploring the properties of lentiviral vectors pseudotyped with alternative viral glycoproteins[8-15]. This parameter is likely to modulate the physico-chemical properties of the vectors, their interaction with the host immune system and their host-range. Several studies have indeed shown that the transduction efficiency of target cells is dependent on the type of glycoprotein used to coat retroviral vectors[16-21]. Additionally, some in vivo gene transfer applications will require vectors that are targeted for specific cell entry and/or gene expression after systemic administration[22]. Due to the wide distribution of its receptor, a lipid component of the plasma membrane[23], VSV-G pseudotypes may bind to the surface of all cells encountered after inoculation before reaching the target cells. Moreover, VSV-G-pseudotyped vectors are rapidly inactivated by human serum[24] and this might impose a limitation on the use of VSV-G as a glycoprotein to pseudotype vectors for systemic gene delivery.

Lentiviral vectors derived from simian immunodeficiency virus (SIV) have been generated in several laboratories[1], including our own[25]. Characterization of these vectors has indicated that they are similar to those derived from human immunodeficiency virus (HIV-1) with respect to the insertion of transgenes in non-proliferating cells, although SIV vectors perform better than HIV-1 vectors in simian cells[25].

SUMMARY OF THE INVENTION

The present invention is directed to chimeric and mutant glycoproteins for use in making pseudotyped viral vector particles. In particular embodiments, the chimeric glycoprotein comprises a cytoplasmic tail domain derived from MLV-A and a transmembrane and extracellular domain derived from feline endogenous virus RD114.

In additional embodiments, the glycoproteins incorporate minimal modifications that allow efficient pseudotype formation with lentivirus-based vectors. Specific embodiments include glycoproteins comprising cleavage sites within the cytoplasmic tail domain compatible with the retroviral core protease of the retroviral vector that is to be pseudotyped with the altered glycoprotein. In particular embodiments, modifications are introduced into a stretch of 8 amino-acids, which encompass a substrate for the viral core protease and whose cleavage is critical for the fusogenicity of the viral glycoprotein. These modifications allow pseudotyping with either oncoretroviral or with different lentiviral cores.

In conjunction with these embodiments, a further embodiment of the invention is a method for matching the amino acid sequence of the cytoplasmic tail of chimeric and mutant glycoproteins with the proteases of retroviral cores, resulting in dramatically improved glycoprotein assembly on those cores.

The invention also encompasses nucleic acid constructs encoding such glycoproteins. In a preferred embodiment, the nucleic acid comprises the sequence of SEQ ID NO: 1. In additional aspect, the construct is an expression construct suitable for expression the glycoproteins such that they are incorporated into recombinant viral vector particles. In an additional aspect, the invention comprises a cell transfected with such nucleic acid constructs.

One embodiment of the invention comprises a vector particle comprising a chimeric glycoprotein wherein the chimeric glycoprotein comprises a cytoplasmic tail domain derived from MLV-A and a transmembrane and extracellular domain derived from feline endogenous virus RD114. In an additional aspect, the vector particle is a pseudotyped vector particle. In a further aspect, the vector particle further comprises a recombinant viral vector construct.

In another embodiment, the vector particle comprises a vector construct wherein the vector construct is derived from a retrovirus or lentivirus. In one aspect, the vector construct is derived from SIV or HIV.

In another embodiment the vector particle comprises a vector construct, which further comprises a transgene. In one aspect, the transgene is a marker or reporter gene. In a particular embodiment, the transgene is a green fluorescent protein (GFP). In another aspect, the transgene is a therapeutic gene. In particular embodiments, the transgene is an oncogene or a proto-oncogene. In another particular embodiment, the transgene is a drug susceptibility gene.

An additional embodiment of the present invention is a method of transducing cells comprising:
  a) obtaining cells to be transduced;
  b) obtaining a pseudotyped vector particle in accordance with claim 8; and
  c) contacting the cells with the vector particle of (b) under conditions sufficient to result in transduction. In an additional embodiment, the method further comprises the step of providing retronectin in an amount sufficient to enhance transduction. In one aspect of the method the cells are transduced in vitro. In another, the cells are transduced in vivo. In further embodiments, the cells are vertebrate cells, primate cells, or human cells. The cells are also contemplated to be CD34+ or PBL cells. Another embodiment of the method encompasses a cell transduced by the method.

Yet another embodiment is a method for producing a recombinant pseudotyped viral vector particle comprising:
  (a) transfecting a cell with:
    (i) at least one vector construct;
    (ii) at least one packaging construct; and
    (iii) an expression construct encoding a chimeric glycoprotein of claim 1 to yield a producer cell;
  (b) culturing the producer cell in a medium; and
  (d) separating the producer cell from the medium to recover the recombinant viral vector particle from the medium.

Another embodiment comprises contacting the cell with a vector particle made in accordance with the methods of the invention and under conditions to effect the transduction of the cell by the recombinant vector. The cell is specifically contemplated to be a human cell, which includes a hematopoietic stem cell or a human CD34+ cell. In an additional embodiment, the cell is treated to stimulate cell proliferation without substantial loss of stem cell pluripotency. In additional aspects, the cell is transduced in vivo or in vitro. In further embodiments, the transduced cell is introduced into an animal subject. The animal subject is a human subject in a preferred embodiment.

A typical example of ex vivo gene therapy encompassed by the invention is a patient suffering from chronic granulatous disease (CGD), whose CD34+ cells can be isolated from the bone marrow or the peripheral blood and transduced ex vivo with a lentivector expressing the gp91phox gene before reimplantation. In the case of patients suffering from severe combined immunodeficiency (SCID), the inventors contemplate a similar approach, using vector constructs of the invention expressing the gene defective in the patient, for example, the gene encoding the common gamma chain of the Interleukin receptor. For the genetic treatment of HIV infection, the present inventors contemplate intracellular immunization, wherein cells are rendered resistant to the HIV virus through the introduction of antiviral genes. In embodiments of the intracellular immunization for HIV, targets of the vectors of the invention include hematopoietic progenitors, peripheral blood CD4+ T cells, and monocytes. As will be recognized by the skilled artisan, similar intracellular immunization methods can be used for other viral infections as well. For the immunotherapy of cancers, tumor cells or antigen presenting cells such as dendritic cells will be genetically engineered with the lentivectors of the invention. For cancer therapies some transgenes that may be used in the lentivector constructs of the invention are those that can inhibit, and/or kill, and/or prevent the proliferation, and/or mediate the apoptosis of, the cancer/tumor cell and/or genes such as TNF.

The vector particles described herein may also be used in vivo, by direct injection into the blood or into a specific organ. For example, in one embodiment intracerebral injection of lentivectors expressing the Glial Cell Derived Nerve Growth Factor (GDNF), can be used for the treatment of Parkinson's disease. In another example, intraportal injection of a lentivector expressing coagulation factor VIII for the correction of hemophilia A is envisioned. In yet another example, intravenous or intramuscular injection of a lentivector of the present invention expressing the dystrophin gene for the treatment of Duchenne Muscular Dystrophy is envisioned. Thus, one of ordinary skill in the art will appreciate the extensive use of the vector constructs and particles of the present invention in terms of gene therapies.

As used herein the specification or claim(s) when used in conjunction with the word "comprising", the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 7A. Representation of RD114 GP cytoplasmic-tail mutants. Alignment of the TM subunits of the RD114 GP with the TMs of type C (MLV-A) or type D (Mason-Pfizer monkey virus-MPMV) mammalian retrovirus Env glycoproteins. (SEQ ID NOS; 28-43, respectively) shows the identical amino-acids in the TMs of MLV-A and MPMV relative to that of RD114. Conserved amino-acids such as I, L or V for aliphatic residues; K or R for positively charged residues and D or E for negatively charged residues are highlighted. The transmembrane domain (M) of the different GPs is boxed. The cytoplasmic tail is formed of two segments: the tail (T) of the mature GP found on virions after removal of the GP carboxy-terminal end (R) by the viral core protease. The protease cleavage sites (boxed) and the YXXL (SEQ ID NO: 26) endocytosis motif (underlined) are shown in the different GPs.

FIG. 7B. Sequences of the carboxy-terminal ends that were modified in RD114 GP are underlined for each mutant. Only the transmembrane domains of the different chimeric GPs is boxed. (*) shows the position of the premature stop codon inserted in the RDRless chimeric GP. (') represents the position of cleavage mediated by the viral core protease.

DESCRIPTION OF ILLUSTRATIVE EMBODIMENTS

Figure 1:
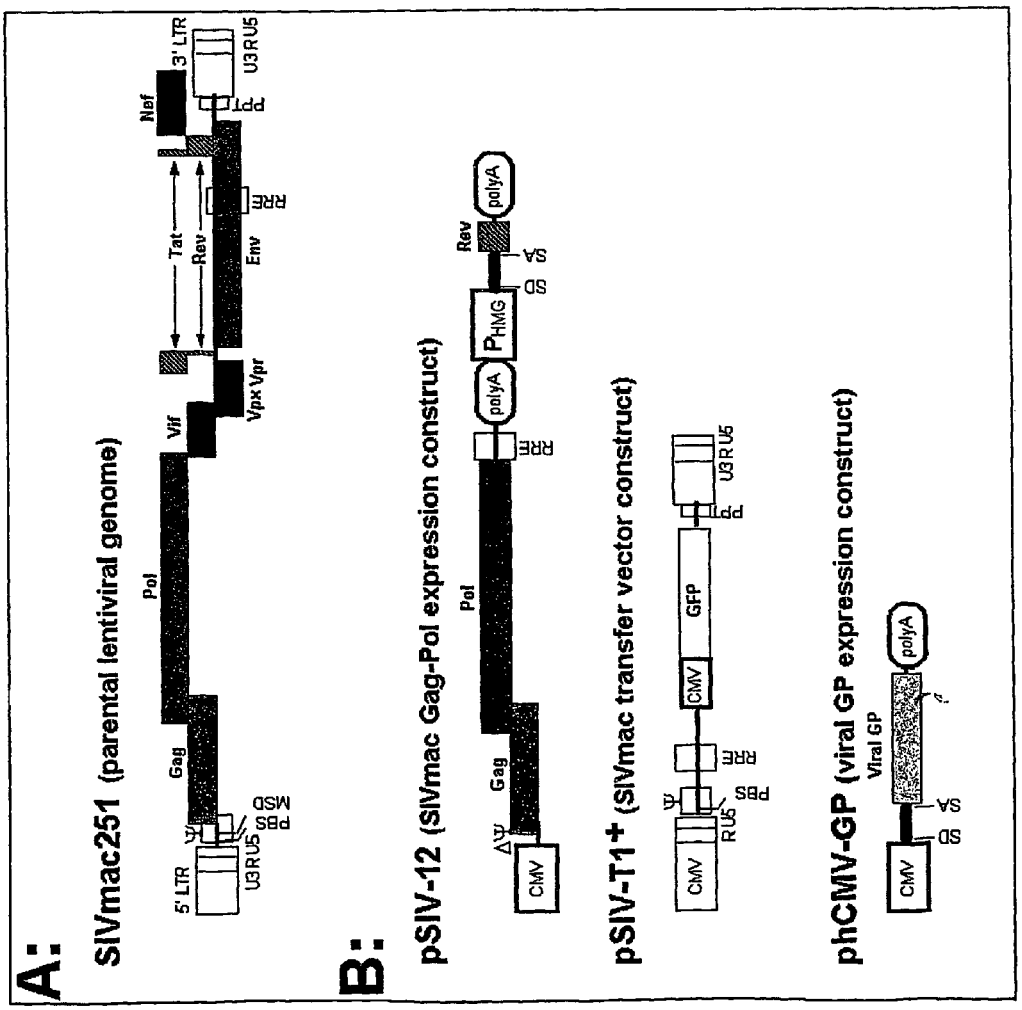
FIG. 1A. Generation of SIVmac251-derived vectors. The genome of an infectious molecular clone of SIVmac (SIVmac251).
FIG. 1B. SIVmac251 was used to derive constructs encoding the packaging functions and constructs carrying the transfer vector. Expression constructs expressing various viral glycoproteins (GP) were also designed. The filled boxes represent the viral genes. The open boxes show the cis-acting sequences. LTR, long terminal repeat; CMV, human cytomegalovirus immediate-early promoter; PBS, primer binding site; MSD, major splice donor site; Ψ, packaging sequence; RRE, Rev-responsive element; $P_{HMG}$, 3-hydroxy-3-methylglutaryl coenzyme A reductase (HMG) promoter; polyA, polyadenylation site; SD, splice donor site; SA, splice acceptor site; SV40, simian virus 40 early promoter. Vector particles were produced by co-transfection of plasmids harboring the packaging functions, the viral glycoproteins and the transfer vector into 293T cells. The supernatants of transfected cells were collected during transient expression, concentrated by ultracentrifugation, and used for target cell transduction.

We have made chimeric GPs encoding the extracellular and transmembrane domains of GALV or RD114 GPs fused to the cytoplasmic tail (designated TR) of MLV-A GP. Surprisingly, SIV-derived vectors pseudotyped with these GALV/TR and RD114/TR GP chimeras have significantly higher titers than vectors coated with the parental GPs. Additionally, RD114/TR-pseudotyped vectors are efficiently concentrated and are resistant to inactivation induced by the complement of both human and macaque sera. Modified RD114 GP-pseudotyped lentiviral vectors are therefore of particular value for in vivo gene transfer applications. Furthermore, as compared to vectors pseudotyped with other retroviral GPs or with VSV-G, RD114/TR-pseudotyped vectors show augmented transduction of human and macaque primary blood lymphocytes and CD34$^+$ cells.

Furthermore, RD114 GP mutants that bear alterations in their transmembrane domains and/or cytoplasmic tails can modulate pseudotype formation either with MLV, SIV or HIV-1 viral core particles. We demonstrate that a cleavage site compatible with the retroviral core protease must be present in the cytoplasmic tail of the RD114 GP to enable efficient pseudotyping. While incompatibility of the cleavage site with the MLV protease alters infectivity of pseudotyped virions but not GP incorporation on MLV cores, compatibility of the cleavage site with the lentiviral protease conditions both GP incorporation and infectivity of pseudotyped lentiviral cores. There is therefore a novel pathway of viral assembly whereby determinants harboured by the cytoplasmic tail of a GP that restrict its incorporation on lentiviral cores should be removed by the viral protease to allow GP incorporation and infectivity of pseudotyped virions.

1. The Cytoplasmic Tail of the RD114 GP Controls Cell-Cell and Virus-Cell Fusogenicity For type C and type D mammalian retrovirus GPs, the cytoplasmic tail is of central importance in the processes that regulate both viral assembly and fusogenicity. Several evidences establish its influence on glycoprotein localisation, cell surface density, cell-cell fusion, interaction/incorporation with heterologous or homologous viral cores and infectivity of the virions. The cytoplasmic tail of these GPs is a structural motif that contains a carboxy-terminal peptide, named R, which harbours a tyrosine endocytosis signal—YXXL—(5), and whose cleavage by the viral protease strongly modulates the properties of the GP. In the native form of the GP, before cleavage, the R peptide is thought to interact i) with the adaptin complex of the cellular endocytosis machinery, ii) with the carboxy-terminal end of the mature GP found in virions (domain T of the cytoplasmic tail in FIG. 1A) and iii) with virion internal proteins (1, 8, 13, 14, 17, 19, 43). Characterisation of mutants of the RD114 glycoprotein (this report) indicates the existence of related signals carried by its cytoplasmic tail. Thus, the RDΔYXXL mutant GPs, in which the YXXL motif was disrupted by point mutagenesis, leads to increased cell-cell fusion most likely via increased cell surface expression, as suggested by studies of others using distinct onco-retroviral and lentiviral glycoproteins (1, 8, 13). However mutations that increased cell-cell fusogenicity and/or cell-surface expression may not necessarily enhance viral incorporation and/or viral infectivity, as inferred by the characterisation of the RDRless, RDPrMLV, RDPrSIV$_{RQAG}$, RDPrHIV and RDΔYXXL mutant GPs. Additionally, our data indicate that the infectivity of pseudotyped vectors depends on the compatibility between the—modified—cytoplasmic tails of RD114 GP and the type of viral core.

Figure 5:
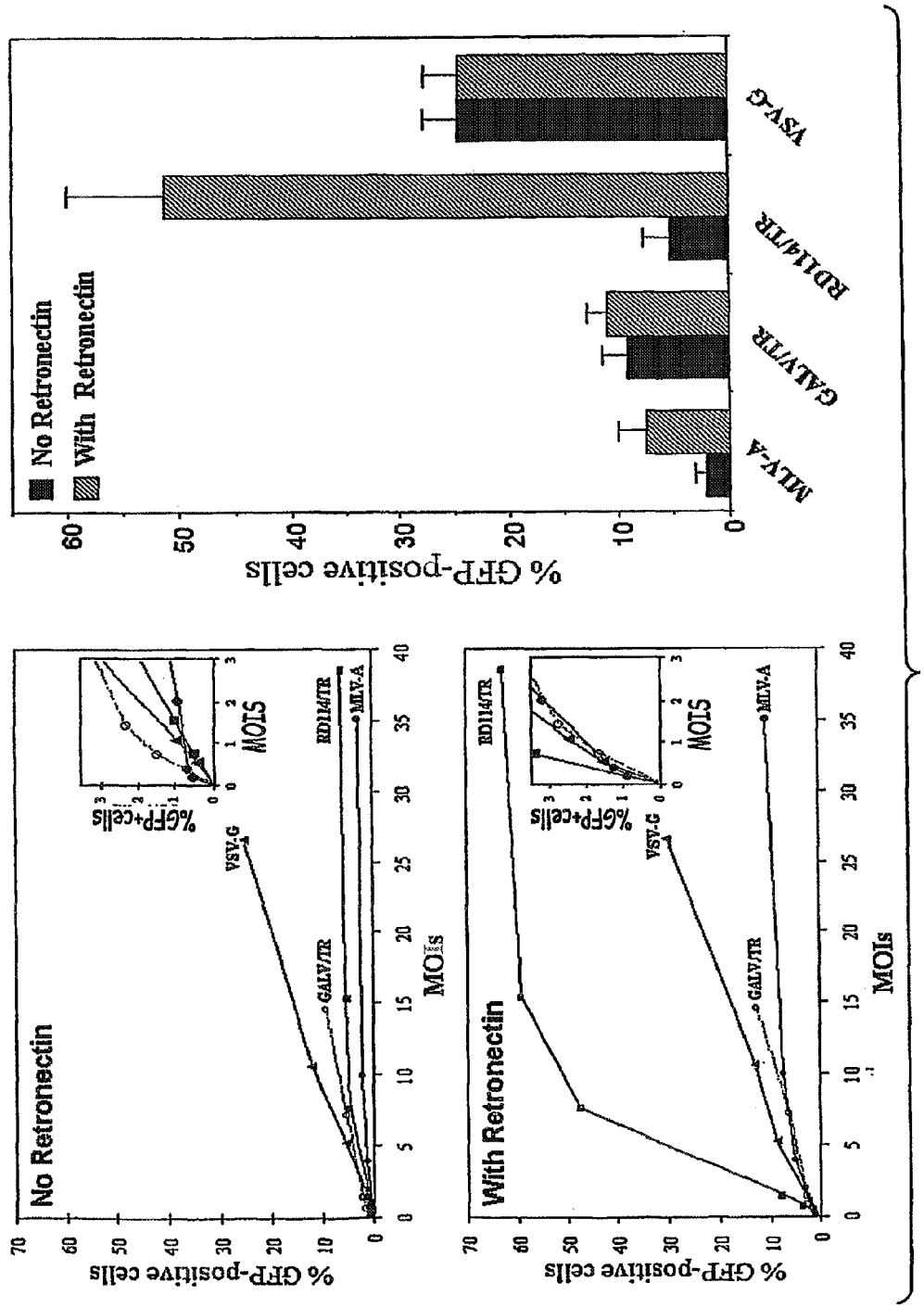
FIG. 5A. Transduction of human and macaque $CD34^+$ cells. $CD34^+$ cells, derived from human mobilized blood were pre-stimulated by overnight incubation with TPO and were transduced for 16 hrs at different multiplicities of infection (MOIs) with SIV-vectors pseudotyped with VSV-G (triangles), MLV-A GP (closed circles), GALV/TR GP (open circles) or RD114/TR GP (closed squares). For each sample of $CD34^+$ cells, transductions were performed in duplicate: in the absence or in the presence of CH-296 retronectin polypeptides coated on the plates. After infection, cells were washed in PBS and cultured in the presence of Flt3-L, TPO, and SCF for an additional 3 days until transduction efficiency was assessed. The dose-response curves of representative experiments are shown for the same batches of $CD34^+$ cells as well as the statistical analyses of the maximal transduction efficiencies of at least four experiments performed with $CD34^+$ cells derived from different donors and stocks of pseudotyped vectors.
FIG. 5B. Transduction of human and macaque $CD34^+$ cells. $CD34^+$ cells, derived from cynomolgus macaque bone marrow were pre-stimulated by overnight incubation with TPO and were transduced for 16 hrs at different multiplicities of infection (MOIs) with SIV-vectors pseudotyped with VSV-G (triangles), MLV-A GP (closed circles), GALV/TR GP (open circles) or RD114/TR GP (closed squares). For each sample of $CD34^+$ cells, transductions were performed in duplicate: in the absence or in the presence of CH-296 retronectin polypeptides coated on the plates. After infection, cells were washed in PBS and cultured in the presence of Flt3-L, TPO, and SCF for an additional 3 days until transduction efficiency was assessed. The dose-response curves of representative experiments are shown for the same batches of $CD34^+$ cells as well as the statistical analyses of the maximal transduction efficiencies of at least four experiments performed with $CD34^+$ cells derived from different donors and stocks of pseudotyped vectors.
Figure 5:
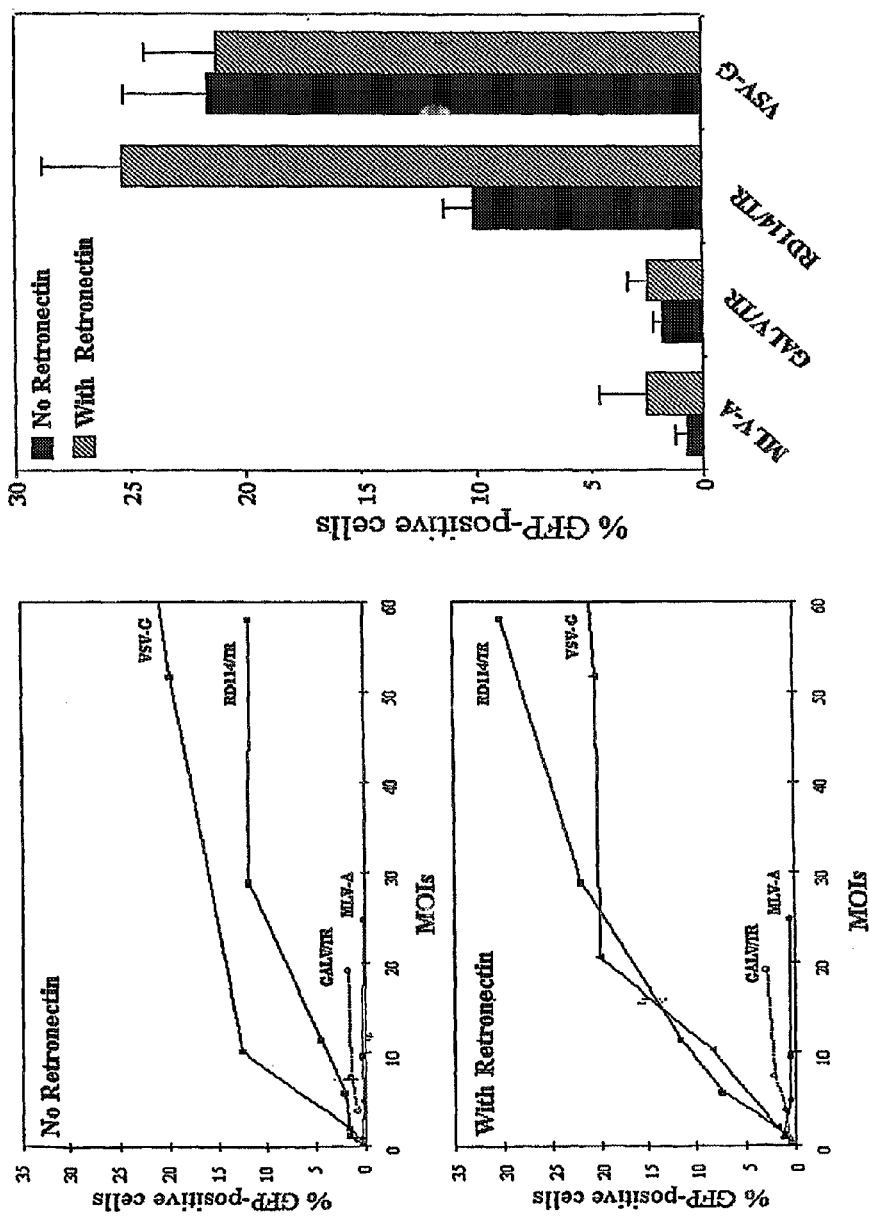

Several genetic evidences obtained with other type C and D mammalian retrovirus GPs indicate that the cytoplasmic tail in its uncleaved—cellular—form acts both as an intrinsic negative regulator of GP fusogenicity (2, 14, 17, 30, 33, 43) and as a partner of the matrix protein during virion assembly (2, 3). Results obtained with the CT mutants of the RD114 glycoprotein indicate that the fusion control of the latter GP is modulated by its cytoplasmic tail in a manner similar to that of type C and D glycoproteins. Indeed cleavage of the cytoplasmic tail was found essential to activate the fusion potential for several type C and D glycoproteins (2, 14, 30, 33), through a not yet defined mechanism. Lack of cleavage of the CT results in poorly fusogenic glycoproteins. Also, premature cleavage, achieved through the insertion of a stop codon at the position of cleavage, strongly enhances syncytia formation (2, 30, 33). Moreover our data directly confirm that the carboxy-terminal end of the RD114 GP must be cleaved during or after virion assembly to allow infectivity (FIG. 5). Additionally mutations in either the region that forms the mature cytoplasmic tail (domain T—FIG. 1B) or in the R peptide alter the control of cell-cell fusion (14, 17, 43), most likely as a result of disruption of the structure and/or integrity of this cytoplasmic tail. Likewise RD114 GP mutants that bear several mutations in the cytoplasmic tail, e.g., RDPrMLV, RDPrSIV$_{RQAG}$ and RDPrHIV mutants may have enhanced cytotoxicity because of the loss of fusion inhibitory control by their mutated cytoplasmic tails.

2. A Novel Pathway of Pseudotype Formation with Lentiviral Cores

Figure 3:
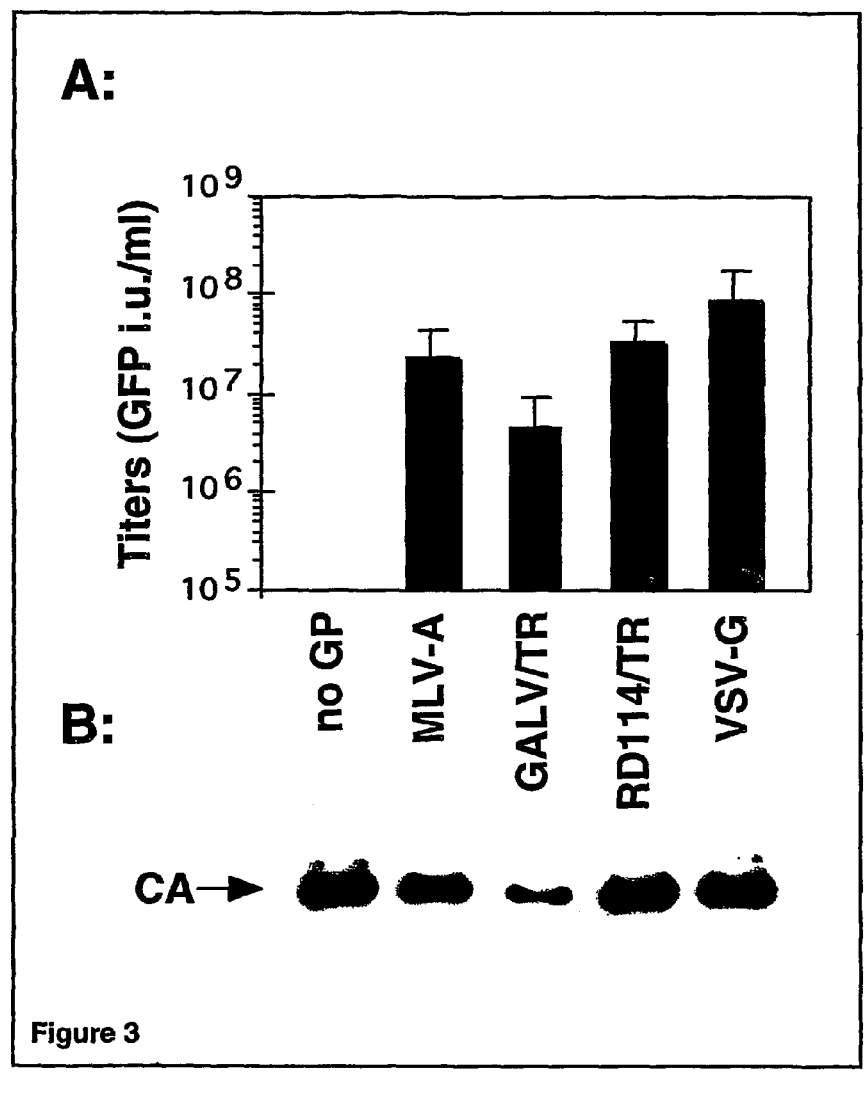
FIG. 3A. Characterization of pseudotyped SIV-based vector stocks. Infectious titers of SIVmac-based vector stocks pseudotyped with the indicated GPs and concentrated by ultracentrifugation. The mean titers±SD from nine individual experiments performed on TE671 target cells are shown.
FIG. 3B. (B) Detection of physical particles was performed by immunoblotting of representative purified vector stocks using anti-SIV-CA (capsid) antibodies.
Figure 4:
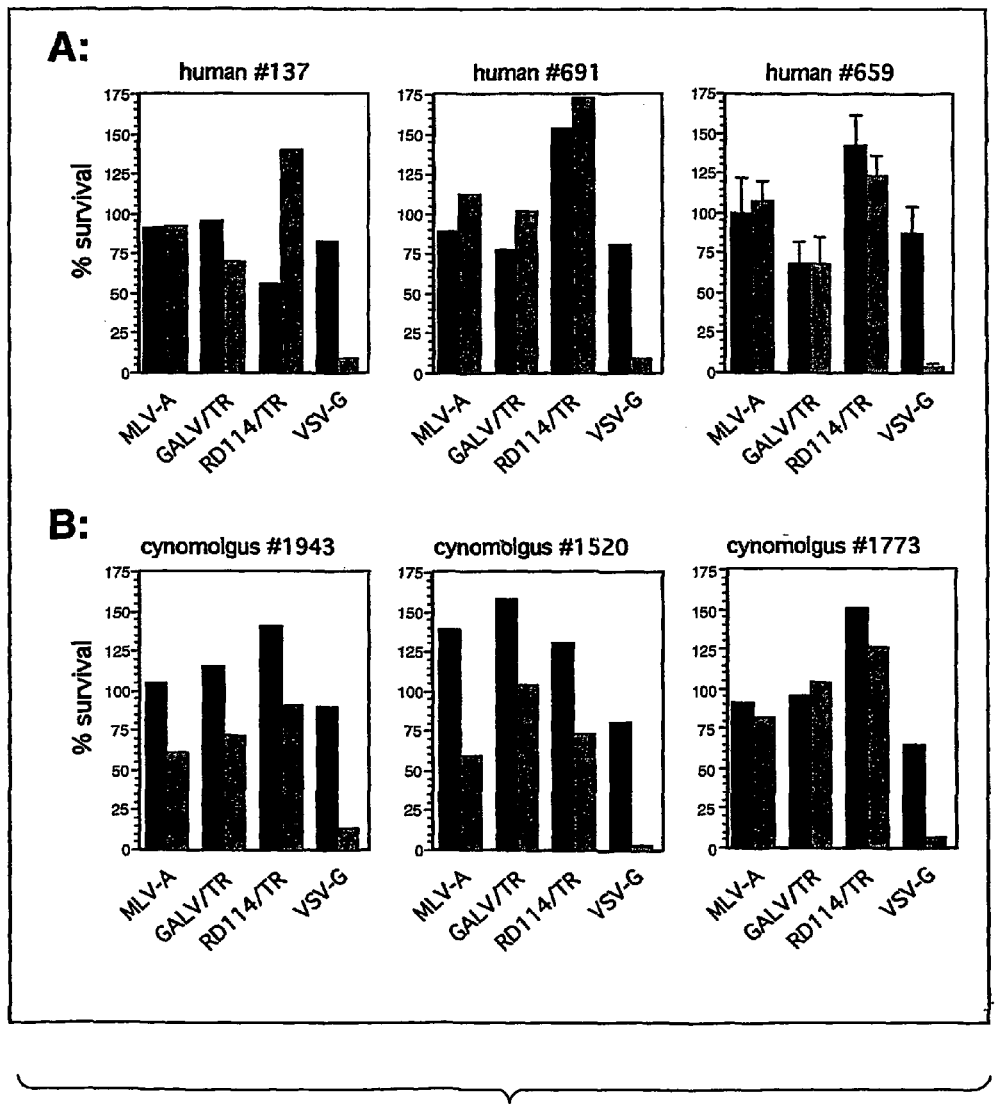
FIG. 4A. Stability of pseudotyped SIV-vector virions in human sera. Infectious pseudotyped SIV-vector particles (50, 000 GFP i.u. in 50 μl of suspension buffer) were mixed with 50 μl of fresh (dashed bars) or heat-inactivated (black bars) human sera. As a reference, virions were mixed with 50 μl of heat-inactivated fetal calf serum (FCS). Virion/sera mixtures were incubated at 37° C. for one hr and then used to transduce TE671 target cells. Values show the titers of primate sera-incubated virions relative to the titers of the same virions incubated in FCS (%). The results of experiments performed with sera of three different individual donors are shown. The experiments with human serum #659 were performed in triplicate and are displayed as mean values±SD.
FIG. 4B. Stability of pseudotyped SIV-vector virions in macaque sera. Infectious pseudotyped SIV-vector particles (50,000 GFP i.u. in 50 µl of suspension buffer) were mixed with 50 µl of fresh (dashed bars) or heat-inactivated (black bars) macaque sera. As a reference, virions were mixed with 50 µl of heat-inactivated fetal calf serum (FCS). Virion/sera mixtures were incubated at 37° C. for one hr and then used to transduce TE671 target cells. Values show the titers of primate sera-incubated virions relative to the titers of the same virions incubated in FCS (%). The results of experiments performed with sera of three different individual donors are shown. The experiments with human serum #659 were performed in triplicate and are displayed as mean values±SD.

Modifications of the cytoplasmic tail of the RD114 GP had little effect on the incorporation of the RD114 GP chimeras on MLV cores, in contrast to lentiviral cores (FIG. 4). This indicated that onco-retroviral cores are more permissive than lentiviral cores for GP incorporation, or, alternatively, that determinants of incompatibility carried by the RD114 GP were restricted to lentiviral cores. However the infectivity of the pseudotyped MLV vector particles was greatly influenced by the type of cleavage site introduced in the cytoplasmic tail of the RD114 GP chimeras (FIG. 3). While the replacement of the RD114 GP cleavage site with that of MLV had not effect on infectivity, the insertion of lentiviral cleavage sites dramatically decreased infection. Consistent with the deficient processing of the cytoplasmic tails of the TM proteins of these latter mutants when incorporated on MLV core particles (FIG. 5A), these results suggested that the poor infectivity of the latter vector pseudotypes was due to lack of activation of fusion potential of the incorporated GP chimeras. For MLV GP, abolishing cleavage of the cytoplasmic tail, achieved through mutations of the cleavage site itself or of the viral protease, resulted in mutants that incorporated normal levels of GP but which were not infectious (33).

Interestingly, the low infectivity of SIV vectors pseudotyped with wild-type RD114 GP could not only be explained by incompatibility of the cleavage site of its cytoplasmic tail with the lentiviral core protease. Indeed, our data suggest that, in contrast to the MLV-A GP, the cytoplasmic tail of the unmodified RD114 glycoprotein may not allow optimal interactions with the lentiviral core, preventing an efficient incorporation of the latter GP (FIG. 4). Examination of the properties of the RD114 GP chimeras may provide a molecular basis for this negative interaction. Indeed replacement of the cytoplasmic tail of the RD114 glycoprotein with that of the incorporation-competent MLV-A GP, resulted in up to 10 fold increased viral incorporation (FIG. 4), demonstrating that the cytoplasmic tail of the RD114 GP contains determinants of incompatibility with the lentiviral core. Interestingly, compatibility could be restored by introducing changes in the specificity of the cleavage site of its cytoplasmic tail. One possibility is that such changes may have induced structural modifications of the cytoplasmic tail that resulted in optimised interactions with SIV core, for example, by reducing steric incompatibilities with the SIV matrix proteins. Yet, our data also suggest the alternative, non-exclusive, possibility that cleavage of the cytoplasmic tail could be associated to GP incorporation. Substitutions of the RD114 GP cleavage site with cleavage sites derived either from the cytoplasmic tail of the pseudotyping-competent MLV-A GP (mutant RDPrMLV) or from SIV Gag proteins (mutant $RDPrSIV_{RQAG}$) resulted in the enhancement of both incorporation on SIV core particles and of viral titers, with the exception of the $RDPrSIV_{ARLM}$ GP mutant. In a recent related study, Cannon et al. found that the unmodified GALV GP was excluded from incorporation on HIV-1 cores (4). Truncation of the R peptide as well as replacement of either the GALV CT or of its cleavage site with the corresponding sequences derived from MLV-A resulted in both increased GP incorporation and viral titers (4), in good agreement with our data obtained with a distinct type of retroviral glycoprotein. Collectively these data therefore suggest that the infectivity of pseudotyped lentiviral vectors is the result of compatibility of the CT of the pseudotyping glycoprotein with the viral core and can be modulated through its cleavage by the viral core protease. While these assumptions should be confirmed by the direct assessment for cleavage of the cytoplasmic tail, we envisage the possibility of a link between cleavage of the cytoplasmic tail and GP incorporation on non-permissive cores. Despite the localisation of onco-retrovirus glycoproteins in plasma membrane lipid rafts (29), where lentiviruses have been shown to initiate budding (25), it is possible that the cytoplasmic tails of these uncleaved GPs are not compatible with the network of matrix proteins. The presence of few active lentiviral protease in the vicinity of the viral assembly site may then cleave the cytoplasmic tails of these GP in a manner dependent on their compatibility with the cleavage site harboured by their CT. This would result in removal of the R peptide and thus in elimination of incompatibility determinants that prevented incorporation on the lentiviral cores. The tailored GPs may then be incorporated on lentiviral particles possibly following a passive mechanism of incorporation.

3. Viral Vectors

Viruses of many types have formed the basis for vectors. Virus infection involves the introduction of the viral genome into the host cell. That property is co-opted for use as a gene delivery vehicle in viral based vectors. The viruses used are often derived from pathogenic viral species that already have many of the necessary traits and abilities to transfect cells. However, not all viruses will successfully transfect all cell types at all stages of the cell cycle. Thus, in the development of viral vectors, viral genomes are often modified to enhance their utility and effectiveness for introducing foreign gene constructs (transgenes) or other nucleic acids. At the same time, modifications may be introduced that reduce or eliminate their ability to cause disease.

Lentiviruses are a subgroup of retroviruses that can infect nondividing cells owing to the karyophilic properties of their preintegration complex, which allow for its active import through the nucleopore. Correspondingly, lentiviral vectors derived from human immunodeficiency virus type 1 (HIV-1) can mediate the efficient delivery, integration and long-term expression of transgenes into non-mitotic cells both in vitro and in vivo (Naldini et al., 1996a; Naldini et al., 1996b; Blomer et al., 1997). For example, HIV-based vectors can efficiently transduce human $CD34^+$ hematopoietic cells in the absence of cytokine stimulation (Akkina et al., 1996; Sutton et al., 1998; Uchida et al., 1998; Miyoshi et al., 1999; Case et al., 1999), and these cells are capable of long-term engraftment in NOD/SCID mice (Miyoshi et al., 1999). Furthermore, bone marrow from these primary recipients can repopulate secondary mice with transduced cells, confirming the lentivector-mediated genetic modification of very primitive hematopoietic precursors, most probably bona fide stem cells. Since none of the other currently available gene delivery systems has such an ability, lentiviral vectors provide a previously unexplored basis for the study of hematopoiesis and similar phenomena, and for the gene therapy of inherited and acquired disorders via the genetic modification of human stem cells (HCLs).

This important capability is subject to significant biosafety concerns (Akkina et al., 1996; Sutton et al., 1998; Uchida et al., 1998). The accidental generation of replication-competent recombinants (RCRs) during the production of lentiviral vector stocks represents one of the major problems to be solved before lentiviral vectors can be considered for human gene therapy.

In the retroviral genome, a single RNA molecule that also contains all the necessary cis-acting elements carries all the coding sequences. Biosafety of a vector production system is therefore best achieved by distributing the sequences encoding its various components over as many independent units as possible, to maximize the number of crossovers that would be required to re-create an RCR. Lentivector particles are generated by co-expressing the virion packaging elements and the vector genome in host producer cells, e.g. 293 human embryonic kidney cells. In the case of HIV-1-based vectors, the core and enzymatic components of the virion come from HIV-1, while the envelope protein is derived from a heterologous virus, most often VSV. The genomic complexity of HIV, where a whole set of genes encodes virulence factors essential for pathogenesis but dispensable for transferring the virus genetic cargo, substantially aids the development of clinically acceptable vector systems.

Multiply attenuated packaging systems typically now comprise only three of the nine genes of HIV-1: gag, encoding the virion main structural proteins, pol, responsible for the retrovirus-specific enzymes, and rev, which encodes a post-transcriptional regulator necessary for efficient gag and pol expression (Dull, et al., 1998). From such an extensively deleted packaging system, the parental virus cannot be reconstituted, since some 60% of its genome has been completely eliminated. In one version of an HIV-based packaging system, Gag/Pol, Rev, VSV G and the vector are produced from four separate DNA units. Also, the overlap between vector and helper sequences has been reduced to a few tens of nucleotides so that opportunities for homologous recombination are minimized.

HIV type 1 (HIV-1) based vector particles may be generated by co-expressing the virion packaging elements and the vector genome in a so-called producer cell, e.g. 293T human embryonic kidney cells. These cells may be transiently transfected with a number of plasmids. Typically from three to four plasmids are employed, but the number may be greater depending upon the degree to which the lentiviral components are broken up into separate units. Generally, one plasmid encodes the core and enzymatic components of the virion, derived from HIV-1. This plasmid is termed the packaging plasmid. Another plasmid encodes the envelope protein(s), most commonly the G protein of vesicular stomatitis virus (VSV G) because of its high stability and broad tropism. This plasmid may be termed the envelope expression plasmid. Yet another plasmid encodes the genome to be transferred to the target cell, that is, the vector itself, and is called the transfer vector. Recombinant viruses with titers of several millions of transducing units per milliliter (TU/ml) can be generated by this technique and variants thereof. After ultracentrifugation concentrated stocks of approximately $10^9$ TU/ml can be obtained.

The vector itself is the only genetic material transferred to the target cells. It typically comprises the transgene cassette flanked by cis-acting elements necessary for its encapsidation, reverse transcription, nuclear import and integration. As has been previously done with oncoretroviral vectors, lentiviral vectors have been made that are "self-inactivating" in that they lose the transcriptional capacity of the viral long terminal repeat (LTR) once transferred to target cells (Zufferey, et al. 1998). This modification further reduces the risk of emergence of replication competent recombinants (RCR) and avoids problems linked to promoter interference.

4. Pseudotyping Viral Vectors

Protein incorporation on retroviruses is not specific to the homologous viral glycoproteins. Over 40 different host cell-derived proteins have been identified on the exterior of HIV-1 viral particles, including major histocompatibility complex class I (MHC-I) and MHC-II molecules, adhesion molecules, co-stimulation molecules and complement control proteins[48]. Additionally, many heterologous viral glycoproteins can be incorporated into retrovirus particles and mediate infectivity[49]. This process, known as pseudotyping, allows retroviral vectors to transduce a broader range of cells and tissues. Engineering of lentiviral vectors with the VSV-G glycoprotein exemplifies the ability of a heterologous glycoprotein to extend the tropism of a vector[2]. However, co-expression of a given glycoprotein (GPs) with a heterologous viral core will not necessarily give rise to highly infectious viral particles[8,14,15,50].

The env gene can be derived from any virus, including retroviruses. Examples of retroviral-derived env genes include, but are not limited to: Moloney murine leukemia virus (MoMuLV or MMLV), Harvey murine sarcoma virus (HaMuSV or HSV), murine mammary tumor virus (MuMTV or MMTV), gibbon ape leukemia virus (GaLV or GALV), human immunodeficiency virus (HIV) and Rous sarcoma virus (RSV). Other env genes such as Vesicular stomatitis virus (VSV) protein G (VSV G), that of hepatitis viruses and of influenza also can be used.

While VSV G protein is a desirable env gene because VSV G confers broad host range on the recombinant virus, VSV G can be deleterious to the host cell, e.g. the packaging cell. Thus, when a gene such as that for VSV G is used, an inducible promoter system may be employed so that VSV G expression can be regulated to minimize host toxicity when VSV G is expression is not required. For example, the tetracycline-regulated gene expression system of Gossen & Bujard, (1992) can be employed to provide for inducible expression of VSV G when tetracycline is withdrawn from the transferred cell. Thus, the tet/VP16 transactivator is present on a first vector and the VSV G coding sequence is cloned downstream from a promoter controlled by tet operator sequences on another vector.

The vector providing the viral env nucleic acid sequence is associated operably with regulatory sequences, e.g., a promoter or enhancer. The regulatory sequence can be any eukaryotic promoter or enhancer, including for example, EF1α, PGK, the Moloney murine leukemia virus promoter-enhancer element, the human cytomegalovirus enhancer, the vaccinia P7.5 promoter or the like (also see examples listed in Tables 1 and 2 below). In some cases, such as the Moloney murine leukemia virus promoter-enhancer element, the promoter-enhancer elements are located within or adjacent to the LTR sequences. Preferably, the regulatory sequence is one which is not endogenous to the lentivirus from which the vector is being constructed. Thus, if the vector is being made from SIV, the SIV regulatory sequence found in the SIV LTR would be replaced by a regulatory element which does not originate from SIV.

One may further target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific. Retroviral vectors can be made target-specific by inserting, for example, a glycolipid or a protein. Targeting often is accomplished by using an antigen-binding portion of an antibody or a recombinant antibody-type molecule, such as a single chain antibody, to target the retroviral vector.

Two types of mechanisms are thought to lead to assembly of homologous and heterologous, viral or cellular, glycoproteins on viral particles. The passive model of GP incorporation implies non-obligatory interactions between the pseudotyping glycoprotein and the viral core, provided that the former is sufficiently abundant at the site of virus budding[51] and that its cytoplasmic tail does not bear determinants that are sterically incompatible with viral assembly or virion morphology[49]. In this respect, heterologous GPs harboring short cytoplasmic tails such as those of FPV, LCMV and VSV (FIG. 2) are likely to be incorporated on lentiviral particles via a passive mechanism. On the other hand, in the active model of GP incorporation, interactions between the cytoplasmic tail of the pseudotyping glycoprotein and components of the virion core dictate assembly of viral particles. There is ample evidence in the literature to support the critical role of such interactions in viral assembly (reviewed in[39,49]), at least for lentiviruses[52-55].

Figure 2:
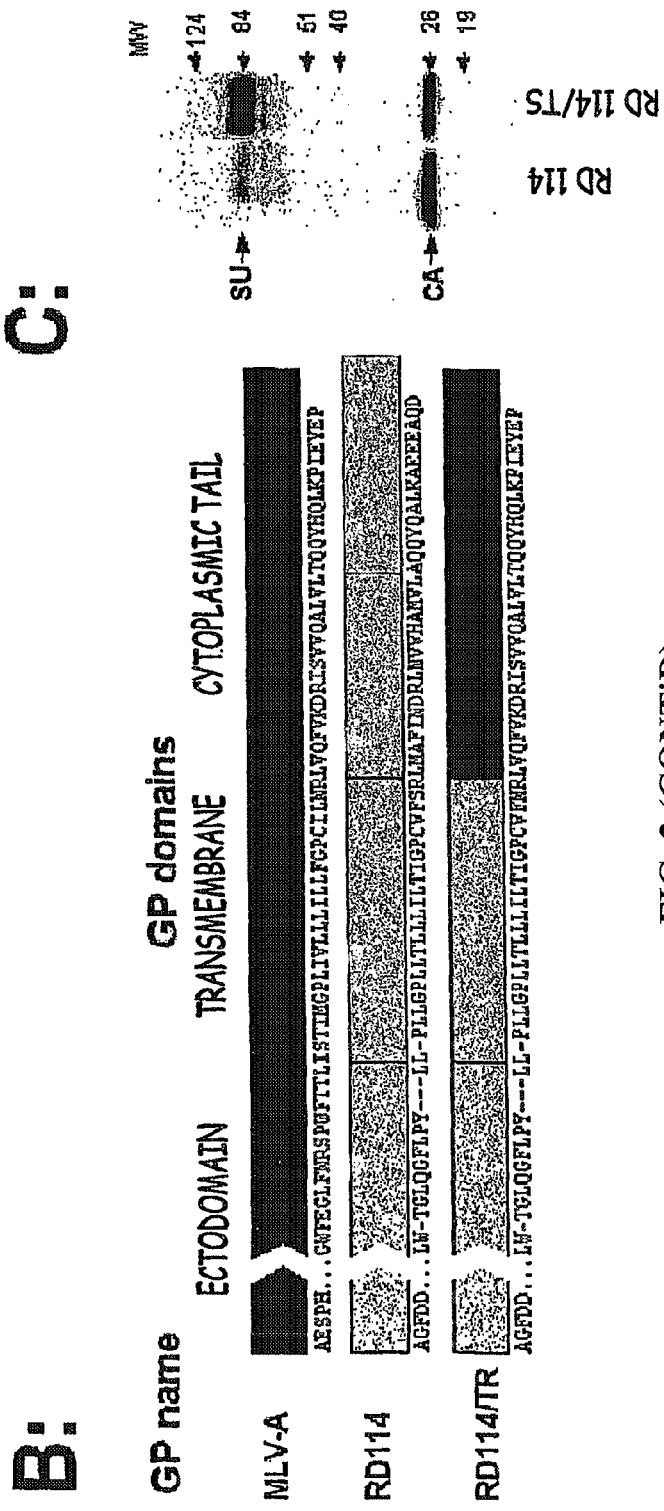
FIG. 2A. Infectious titers of SIVmac-derived vectors pseudotyped with different viral glycoproteins. Vectors carrying the GFP marker gene were generated with the indicated GPs of retroviral or non-retroviral (stars) origins. EboV, Ebola virus; FPV-HA, hemagglutinin of fowl plague virus; GALV, gibbon ape leukemia virus; MLV-A, amphotropic murine leukemia virus; LCMV, lymphocytic choriomeningitis virus; VSV, vesicular stomatitis virus. TE671 target cells were infected with dilutions of non-concentrated vector preparations and the percentage of GFP-positive cells was determined 3 days post-infection. Infectious titers were calculated as GFP i.u./ml. In duplicate experiments, vector producer cells expressing the FPV-HA were treated with 2U of Clostridium perfringens neuraminidase (Sigma-Aldrich, France) for 24 hrs to induce the release of HA-pseudotyped particles from the surface of producer cells (FPV-HA+NA).
FIG. 2B. Schematic representation of the RD114/TR chimeric GP in which the cytoplasmic domain of the RD114 glycoprotein was replaced with that of the MLV-A GP. The sequences of the three topological domains, ectodomain, transmembrane and cytoplasmic tail, are shown for MLV-A RD114 and RD114/TR (SEQ ID NOS: 23 24 and 25, respectively). The GALV/TR chimeric GP was modified in a similar manner.
FIG. 2C. Incorporation of RD114 and RD114/TR GPs in virions was assessed in immunoblots of SIV vector particles pelleted through 20% sucrose cushions, using anti-RD114 SU and anti-CA antibodies. The position of the molecular weight markers is shown (kDa)

In a recent study we proposed that pseudotyping of lentiviral core particles with the glycoproteins of type C and D mammalian retroviruses involves an alternative pathway of assembly[14]. The GPs of some of these retroviruses, like the GALV and the RD114 viruses, have been shown to harbor in their cytoplasmic tail a determinant that restricts incorporation on lentiviral cores[8,14]. The relatively short cytoplasmic tails of type C/D mammalian retrovirus GPs, of about 30-40 amino-acid-long, harbor a 15-20 amino-acid-long carboxy-terminal peptide, named R for MLVs, whose cleavage by the homologous viral core protease is required to activate the fusion potential of the glycoprotein[56-58]. For pseudotype formation with homologous type C/D viral cores, lack of cleavage of the R peptide by the viral protease alters infectivity of pseudotyped virions but not GP incorporation[14,56,58]. In contrast, the compatibility of the cleavage site with the lentiviral protease affects both GP incorporation and infectivity of pseudotyped lentiviral cores particles[14]. Thus, a possible pathway of incorporation of these GPs on lentiviral cores may involve cleavage of the R peptide by active core protease at the site of virion assembly, resulting in removal of the cytoplasmic tail determinant that impaired pseudotyping. Based on these observations, we have generated efficient SIV-derived vectors pseudotyped with chimeric GPs derived from GALV[8] and RD114 (FIG. 2). These mutant glycoproteins, named GALV/TR and RD114/TR (FIG. 2), respectively, harbor the cytoplasmic tail of the MLV-A GP whose cleavage site is compatible with the HIV-1 and SIV proteases. It is likely due to this property that they are efficiently incorporated on lentiviral particles (FIG. 2C).

5. Stability of Lentiviral Vector Pseudotypes in Primate Sera

VSV-G-pseudotyped lentiviral vectors have proved useful to transduce several cell types in vivo or in vitro[3-7]. Yet their high sensitivity to human[24] and non-human primate (FIG. 4) complement may preclude their utility for in vivo systemic administration. In contrast to VSV-G pseudotypes, vectors generated with retroviral glycoproteins were stable in human and macaque sera, with RD114/TR-pseudotyped SIV vectors being constantly resistant to human sera, suggesting that the latter vectors could be particularly suitable for systemic gene delivery (FIG. 4). Several factors contribute in determining complement sensitivity and depend on: i) sera from different individuals, ii) type of producer cells[34,36], iii) presence of α(1-3)galactose sugar epitope in glycoproteins[59-61] or iv) type of pseudotyping GP[34,36,62]. Retroviruses produced by human cells are usually resistant in human serum[34,36], with the exception of VSV-G-pseudotyped vectors[24]. However, in a recent study, it was found that onco-retroviral vectors coated with MLV GPs and produced by human cells were differentially sensitive to complement inactivation in sera from non-human Old World primates in a manner that correlated with increasing evolutionary distance from humans[63]. Sensitivity to macaque sera resulted in more than 99% vector degradation[63]. Thus, in apparent disagreement with these latter results obtained with onco-retroviral vectors, here we found that lentiviral vectors pseudotyped with retroviral GPs are relatively stable in macaque sera (FIG. 4B). A factor that could modulate response to sera and explain the discrepancy between onco-retroviral and lentiviral particles may be the incorporation of the CD46, CD55, and CD59 complement inhibitory molecules into lentiviral particles, as reported for HIV and SIV[48,64].

6. Transduction of Primary Cells with Pseudotyped SIV Vectors

The broad tropism of VSV-G-pseudotyped lentiviral vectors may not be suitable for particular gene transfer applications where cell type-specific gene delivery would be required. More selective tropisms could be achieved by taking advantage of the natural tropisms of glycoproteins derived from some membrane-enveloped viruses or, alternatively, by engineering the host-range of incorporation-competent GPs (e.g., MLV, GALV/TR or FPV-HA)[65,66]. For instance, the use of surface glycoproteins derived from viruses that cause lung infection and infect via the airway epithelia, like Ebola virus or Influenza virus, may prove useful for gene therapy of the human airway[10]. Nevertheless, it should be noted that lentiviral vector pseudotypes might not always retain the host range of the parental viruses from which the pseudotyping glycoproteins were derived. For example, although the glycoprotein of the Mokola virus, a neurotropic lyssavirus, efficiently pseudotypes HIV-1 vectors[12], the pseudotyped vectors do not reproduce the specific neurotropism of the parental virus[9].

Recent reports have demonstrated that onco-retroviral vectors pseudotyped with the RD114 GP efficiently transduce human and canine CD34+ cells[16-18,21]. Transduced cells could repopulate NOD/SCID mice and dogs with an efficiency similar to that of non-transduced cells and displayed multilineage expression[16-18]. From these studies, it was suggested that, in human CD34+ cells, the "major barrier to gene transfer is at the receptor level and is not due to the quiescence of the target cells"[18]. We attempted to test this hypothesis with lentiviral vectors pseudotyped with the MLV-A, GALV/TR, RD114/TR and VSV-G glycoproteins. In contrast to the former studies, we used conditions of infection that would minimize the influence of factors that may affect virus/receptor interactions and/or transduction, i.e., no reiterated infections, absence of retronectin or stromal cells and only minimal cytokine treatment. Thus, human CD34+ cells were transduced by a single and short virus/cell exposure under cytokine treatment that would not allow MLV vectors to transduce the CD34+ cells[26]. Because of these sub-optimal conditions, the maximal levels of gene transfer were relatively low; yet they allowed reliable comparison of the specific influence of the pseudotyping GPs in CD34+ cells transduction. The best glycoproteins under these conditions were clearly the VSV-G and GALV/TR GPs (FIG. 5A). Compared to VSV-G, much lower transduction levels were achieved with vectors pseudotyped with the MLV-A and RD114/TR GPs. These results may reflect differences in the pattern of receptor expression on the CD34+ cells for the different GPs and seem to contradict those previously reported with onco-retroviral vectors[18]. However, in agreement with the previous studies[16-18], the combined use of the RD114/TR GP and retronectin strongly increased transduction of human cells, allowing RD114/TR-pseudotyped lentiviral vectors to surpass those pseudotyped with VSV-G (FIG. 5). The mechanisms by which CH-296 retronectin fragment enhances infection may involve the co-localization of retroviral particles and target cells[43], owing to the property of CH-296 to bind both the cell surface, through its attachment to $\alpha_{4/5}\beta_1$ integrins, and the viral glycoprotein, through a high-affinity heparin II domain[42]. Although alternative explanations, involving inhibition of apoptosis and stimulation of cell division, have been proposed[67], our results are in favor of the former mechanism since differential effects of CH-296 were detected according to the type of glycoprotein used to pseudotype the lentiviral core particles. Proteins of the extra-cellular matrix, such as heparan sulfate proteoglycans, play a major role in the initial steps of infection and perhaps are more important to mediate viral/cell attachment[68] than the viral receptors themselves, that primarily serve to trigger membrane fusion[69,70]. Motifs that differentially influence binding to extra-cellular matrix proteins have been identified in glycoproteins of several enveloped viruses[71,72]. They may be particularly efficient in the RD114 glycoprotein and stimulate CH-296-mediated attachment to cells.

RD114/TR-pseudotyped SIV vectors very efficiently transduced human and macaque PBLs (FIG. 6), in the absence of retronectin. Indeed, in these cells, there was a striking difference in the transduction efficiencies observed with vectors pseudotyped with either VSV-G or MLV-A GP and those coated with RD114/TR GP. The reasons for this discrepancy may lie in difference in expression of the receptors for these GPs. Alternatively these results may not necessarily involve differences in receptor density and/or initial virus/receptor interaction parameters. Several reports have shown that transduction efficiency does not correlate with the level of receptor expression[17,73] but rather establish the importance of post-binding events such as receptor clustering, membrane fusion mechanism, site of fusion, uncoating and migration of the viral particle from the site of uncoating and the nucleus[74,75]. It can therefore be surmised that, for transduction of PBLs with SIV vectors, the RD114 receptor modulates post-binding events in a more efficient fashion than the VSV-G or MLV-A receptors.

Cells may be transduced in vivo or in vitro, depending on the ultimate application. Even in the context of human gene therapy, such as gene therapy of human stem cells, one may transduce the stem cell in vivo or, alternatively, transduce in vitro followed by infusion of the transduced stem cell into a human subject. In one aspect of this embodiment, the human stem cell can be removed from a human, e.g., a human patient, using methods well known to those of skill in the art and transduced as noted above. The transduced stem cells are then reintroduced into the same or a different human.

Where a human subject is treated directly by introduction of the vector into the subject, the treatment is typically carried out by intravenous administration of the vector. When cells, for instance $CD34^+$ cells, dendritic cells, peripheral blood cells or tumor cells are transduced ex vivo, the vector particles are incubated with the cells using a dose generally in the order of between 1 to 50 multiplicities of infection (MOI) which also corresponds to $1\times10^5$ to $50\times10^5$ transducing units of the viral vector per $10^5$ cells. This of course includes amount of vector corresponding to 1, 2, 3, 4, 5, 6, 7, 8, 9, 10, 15, 20, 25, 30, 35, 40, 45, and 50 MOI. Typically, the amount of vector may be expressed in terms of HeLa transducing units (TU). Other routes for vector administration include intrarterially, endoscopically, intralesionally, percutaneously, subcutaneously, intramuscular, intrathecally, intraorbitally, intradermally, intraperitoneally, transtracheally, subcuticularly, by intrastemal injection, by inhalation or intranasal spraying, by endotracheal route and the like. In embodiments concerning tumor/cancer therapies with the vectors of the invention the expression vector can be delivered by direct injection into the tumor or into the tumor vasculature.

7. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous nucleic acid encoded by the vectors of this invention. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a lentivector of the invention bearing a therapeutic gene construct, has been introduced. Therefore, recombinant cells are distinguishable from naturally occurring cells which do not contain a recombinantly introduced nucleic acid.

In certain embodiments, it is contemplated that RNAs or proteinaceous sequences may be co-expressed with other selected RNAs or proteinaceous sequences in the same host cell. Co-expression may be achieved by co-transfecting the host cell with two or more distinct recombinant vectors. Alternatively, a single recombinant vector may be constructed to include multiple distinct coding regions for RNAs, which could then be expressed in host cells transfected with the single vector.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials. Some examples of host cells used in this invention include but are not limited to virus packaging cells, virus producer cells, 293T cells, human hematopoietic progenitor cells, human hematopoietic stem cells, $CD34^+$ cells $CD4^+$ cells, and the like.

A. Tissues and Cells

It will be understood by the skilled artisan that the invention is not limited to any one particular cell type and that one may use the lentiviral vectors and methods of the invention for the expression of transgenes in many cell types. Some examples of cell types contemplated include terminally differentiated cells such as neurons, lung cells, muscle cells, liver cells, pancreatic cells, endothelial cells, cardiac cells, skin cells, bone marrow stromal cells, ear and eye cells. Additionally, stem cells and progenitor cells such as pancreatic ductal cells, neural precursors, and mesodermal stem cells are also contemplated. Most notably, however, the more preferred lentivectors of the present invention have highly desirable features that permit the high level expression of transgenes in human progenitor cells while meeting human biosafety requirements.

For the production of virus particles, one may employ any cell that is compatible with the expression of lentiviral Gag and Pol genes, or any cell that can be engineered to support such expression. For example, producer cells such as 293T cells, TE 671 and HT1080 cells may be used.

Of course, as noted, the lentivectors of the invention will be particularly useful in the transduction of human hematopoietic progenitor cell or a hematopoietic stem cell, obtained either from the bone marrow, the peripheral blood or the umbilical cord blood, as well as in the transduction of a $CD4^+$ T cell, a peripheral blood B or T lymphocyte cell, a peripheral blood mononuclear cell, a dendritic cell, and a monocytic cell. Particularly preferred targets are $CD34^+$ cells.

A tissue may comprise a host cell or cells to be transformed or contacted with a nucleic acid delivery composition and/or an additional agent. The tissue may be part or separated from an organism. In certain embodiments, a tissue and its constituent cells may comprise, but is not limited to, blood (e.g., hematopoietic cells (such as human hematopoietic progenitor cells, human hematopoietic stem cells, $CD34^+$ cells $CD4^+$ cells), lymphocytes and other blood lineage cells), bone marrow, brain, stem cells, blood vessel, liver, lung, bone, breast, cartilage, cervix, colon, cornea, embryonic, endometrium, endothelial, epithelial, esophagus, fascia, fibroblast, follicular, ganglion cells, glial cells, goblet cells, kidney, lymph node, muscle, neuron, ovaries, pancreas, peripheral blood, prostate, skin, skin, small intestine, spleen, stomach, testes.

B. Organisms

In certain embodiments, the host cell or tissue may be comprised in at least one organism. In certain embodiments, the organism may be, human, primate or murine. In other embodiments the organism may be any eukaryote or even a prokaryote (e.g., a eubacteria, an archaea), as would be understood by one of ordinary skill in the art. Some lentivectors of the invention may employ control sequences that allow them to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of the lentivectors of the invention, as well as production of the nucleic acids encoded by the lentivectors and their cognate polypeptides, proteins, or peptides some of which are therapeutic genes or proteins which will be used for gene therapies.

C. Injectable Compositions and Pharmaceutical Formulations

To achieve gene-therapy using the lentiviral vector compositions of the present invention, one would generally contact a cell in need thereof with a lentiviral vector comprising a therapeutic gene. The cell will further be in an organism such as a human in need of the gene therapy. The routes of administration will vary, naturally, with the location and nature of the disease, and include, e.g., intravenous, intraarterial, intradermal, transdermal, intramuscular, intranasal, subcutaneous, percutaneous, intratracheal, intraperitoneal, intratumoral, perfusion and lavage. The cells will also sometimes be isolated from the organisms, exposed to the lentivector ex vivo, and reimplanted afterwards.

Injection of lentiviral nucleic acid constructs of the invention may be delivered by syringe or any other method used for injection of a solution, as long as the expression construct can pass through the particular gauge of needle required for injection. A novel needleless injection system has recently been described (U.S. Pat. No. 5,846,233) having a nozzle defining an ampule chamber for holding the solution and an energy device for pushing the solution out of the nozzle to the site of delivery. A syringe system has also been described for use in gene therapy that permits multiple injections of predetermined quantities of a solution precisely at any depth (U.S. Pat. No. 5,846,225).

Solutions of the nucleic acids as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intraarterial, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

The terms "contacted" and "exposed," when applied to a cell, are used herein to describe the process by which a therapeutic lentiviral vector is delivered to a target cell.

For gene-therapy to discrete, solid, accessible tumors, intratumoral injection, or injection into the tumor vasculature is specifically contemplated. Local, regional or systemic administration also may be appropriate. For tumors of >4 cm, the volume to be administered will be about 4-10 ml (preferably 10 ml), while for tumors of <4 cm, a volume of about 1-3 ml will be used (preferably 3 ml). Multiple injections delivered as single dose comprise about 0.1 to about 0.5 ml volumes. The viral particles may advantageously be contacted by administering multiple injections to the tumor, spaced at approximately 1 cm intervals. Systemic administration is preferred for conditions such as hematological malignancies.

Continuous administration also may be applied where appropriate. Delivery via syringe or catherization is preferred. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs.

Treatment regimens may vary as well, and often depend on type of disease and location of diseased tissue, and factors such as the health and the age of the patient. The clinician will be best suited to make such decisions based on the known efficacy and toxicity (if any) of the therapeutic formulations based on lentiviral vectors of the present invention.

The treatments may include various "unit doses." A unit dose is defined as containing a predetermined-quantity of the therapeutic composition comprising a lentiviral vector of the present invention. The quantity to be administered, and the particular route and formulation, are within the skill of those in the clinical arts. A unit dose need not be administered as a single injection but may comprise continuous infusion over a set period of time. Unit dose of the present invention may conveniently be described in terms of transducing units (T.U.) of lentivector, as defined by tittering the vector on a cell line such as HeLa or 293. Unit doses range from $10^3$, $10^4$, $10^5$, $10^6$, $10^7$, $10^8$, $10^9$, $10^{10}$, $10^{11}$, $10^{12}$, $10^{13}$ T.U. and higher.

8. Nucleic Acids

A. Transgenes and Disease Treatments

One embodiment of the present invention is to transfer nucleic acids encoding a therapeutic gene, especially a gene that provides therapy for hematopoietic and lympho-hematopoietic disorders, such as the inherited or acquired disorders described above. In one embodiment the nucleic acids encode a full-length, substantially full-length, or functional equivalent form of such a gene. These genes may be known as transgenes.

It is believed that the lentivectors of the present invention may be employed to deliver any transgene that one desires, depending on the application. In the case of delivery to hematopoietic progenitor cells, one will typically select a transgene that will confer a desirable function on such cells, including, for example, globin genes, hematopoietic growth factors, which include erythropoietin (EPO), the interleukins (such as Interleukin-1 (IL-1), Interleukin-2 (IL-2), Interleukin-3 (IL-3), Interleukin-6 (IL-6), Interleukin-12 (IL-12), etc.) and the colony-stimulating factors (such as granulocyte colony-stimulating factor, granulocyte/macrophage colony-stimulating factor, or stem-cell colony-stimulating factor), the platelet-specific integrin αIIbβ, multidrug resistance genes, the gp91 or gp 47 genes that are defective in patients with chronic granulomatous disease (CGD), antiviral genes rendering cells resistant to infections with pathogens such as human immunodeficiency virus, genes coding for blood coagulation factors VIII or IX which are mutated in hemophiliacs, ligands involved in T cell-mediated immune responses such as T cell antigen receptors, B cell antigen receptors (immunoglobulins), the interleukin receptor common γ chain, as well as combination of T and B cell antigen receptors alone or in combination with single chain antibodies such as ScFv, tumor necrosis factor (TNF), IL-2, IL-12, gamma interferon, CTLA4, B7 and the like, genes expressed in tumor cells such as Melana, MAGE genes (such as MAGE-1, MAGE-3), P198, P1A, gp100 etc.

A principal application of the present invention will be to provide for vectors that deliver desired transgenes to hematopoietic cells for a number of possible reasons. This might include, but of course not be limited to, the treatment of myelosupression and neutropenias which may be caused as a result of chemotherapy or immunosupressive therapy or infections such as AIDS, genetic disorders, cancers and the like.

Exemplary genetic disorders of hematopoietic cells that are contemplated include sickle cell anemia, thalassemias, hemaglobinopathies, Glanzmann thrombasthenia, lysosomal storage disorders (such as Fabry disease, Gaucher disease, Niemann-Pick disease, and Wiskott-Aldrich syndrome), severe combined immunodeficiency syndromes (SCID), as well as diseases resulting from the lack of systemic production of a secreted protein, for example, coagulation factor VIII and/or IX. In such cases, one would desire to introduce transgenes such as globin genes, hematopoietic growth factors, which include erythropoietin (EPO), the interleukins (especially Interleukin-1, Interleukin-2, Interleukin-3, Interleukin-6, Interleukin-12, etc.) and the colony-stimulating factors (such as granulocyte colony-stimulating factor, granulocyte/macrophage colony-stimulating factor, or stem-cell colony-stimulating factor), the platelet-specific integrin αIIbβ, multidrug resistance genes, the gp91 or gp 47 genes which are defective in patients with chronic granulomatous disease (CGD), antiviral genes rendering cells resistant to infections with pathogens such as human immunodeficiency virus, genes coding for blood coagulation factors VIII or IX which are mutated in hemophiliacs, ligands involved in T cell-mediated immune responses such as T cell antigen receptors, B cell antigen receptors (immunoglobulins), the interleukin receptor common γ chain, a combination of both T and B cell antigen receptors alone and/or in combination with single chain antibodies (ScFv), IL2, IL12, TNF, gamma interferon, CTLA4, B7 and the like, genes expressed in tumor cells such as Melana, MAGE genes (such as MAGE-1, MAGE-3), P198, P1A, gp100 etc.

Exemplary cancers are those of hematopoietic origin, for example, arising from myeloid, lymphoid or erythroid lineages, or precursor cells thereof. Exemplary myeloid disorders include, but are not limited to, acute promyeloid leukemia (APML), acute myelogenous leukemia (AML) and chronic myelogenous leukemia (CML). Lymphoid malignancies which may be treated utilizing the lentivectors of the present invention include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas contemplated as candidates for treatment utilizing the lentiviral vectors of the present invention include, but are not limited to non-Hodgkin lymphoma and variants thereof, peripheral T-cell lymphomas, adult T-cell leukemia/lymphoma (ATL), cutaneous T-cell lymphoma (CTCL), large granular lymphocytic leukemia (LGF) and Hodgkin's disease.

Thus, in some embodiments of the present invention, the treatment of a hematopoietic and lympho-hematopoietic disorder involves the administration of a lentiviral vector of the invention comprising a therapeutic nucleic acid expression construct to a cell of hematopoietic origin. The use of a lentiviral vector of the invention comprising a therapeutic nucleic acid expression construct for the manufacture of a medicament intended for the treatment of a hematopoietic and lympho-hematopoietic disorder is also within the scope of the invention. It is contemplated that the hematopoietic cells take up the construct and express the therapeutic polypeptide encoded by nucleic acid, thereby restoring the cells normal phenotype.

A nucleic acid may be made by any technique known to one of ordinary skill in the art. Non-limiting examples of synthetic nucleic acid, particularly a synthetic oligonucleotide, include a nucleic acid made by in vitro chemical synthesis using phosphotriester, phosphite or phosphoramidite chemistry and solid phase techniques such as described in EP 266,032, or via deoxynucleoside H-phosphonate intermediates as described by Froehler et al., 1986, and U.S. Pat. No. 5,705,629. A non-limiting example of enzymatically produced nucleic acid include one produced by enzymes in amplification reactions such as PCR™ (see for example, U.S. Pat. No. 4,683,202 and U.S. Pat. No. 4,682,195) or the synthesis of oligonucleotides described in U.S. Pat. No. 5,645, 897. A non-limiting example of a biologically produced nucleic acid includes recombinant nucleic acid production in living cells (see for example, Sambrook et al. 2000).

A nucleic acid may be purified on polyacrylamide gels, cesium chloride centrifugation gradients, or by any other means known to one of ordinary skill in the art (see for example, Sambrook et al. 2000).

The term "nucleic acid" will generally refer to at least one molecule or strand of DNA, RNA or a derivative or mimic thereof, comprising at least one nucleobase, such as, for example, a naturally occurring purine or pyrimidine base found in DNA (e.g., adenine "A," guanine "G," thymine "T," and cytosine "C") or RNA (e.g. A, G, uracil "U," and C). The term "nucleic acid" encompasses the terms "oligonucleotide" and "polynucleotide." The term "oligonucleotide" refers to at least one molecule of between about 3 and about 100 nucleobases in length. The term "polynucleotide" refers to at least one molecule of greater than about 100 nucleobases in length. These definitions generally refer to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule.

In certain embodiments, a "gene" refers to a nucleic acid that is transcribed. As used herein, a "gene segment" is a nucleic acid segment of a gene. In certain aspects, the gene includes regulatory sequences involved in transcription, or message production or composition. In particular embodiments, the gene comprises transcribed sequences that encode for a protein, polypeptide or peptide. In other particular aspects, the gene comprises a nucleic acid, and/or encodes a polypeptide or peptide-coding sequences of a gene that is defective or mutated in a hematopoietic and lympho-hematopoietic disorder. In keeping with the terminology described herein, an "isolated gene" may comprise transcribed nucleic acid(s), regulatory sequences, coding sequences, or the like, isolated substantially away from other such sequences, such as other naturally occurring genes, regulatory sequences, polypeptide or peptide encoding sequences, etc. In this respect, the term "gene" is used for simplicity to refer to a nucleic acid comprising a nucleotide sequence that is transcribed, and the complement thereof. In particular aspects, the transcribed nucleotide sequence comprises at least one functional protein, polypeptide and/or peptide encoding unit. As will be understood by those in the art, this functional term "gene" includes both genomic sequences, RNA or cDNA sequences, or smaller engineered nucleic acid segments, including nucleic acid segments of a non-transcribed part of a gene, including but not limited to the non-transcribed promoter or enhancer regions of a gene. Smaller engineered gene nucleic acid segments may express, or may be adapted to express using nucleic acid manipulation technology, proteins, polypeptides, domains, peptides, fusion proteins, mutants and/or such like. Thus, a "truncated gene" refers to a nucleic acid sequence that is missing a stretch of contiguous nucleic acid residues.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

n to n+y where n is an integer from 1 to the last number of the sequence and y is the length of the nucleic acid segment minus one, where n+y does not exceed the last number of the sequence. Thus, for a 10-mer, the nucleic acid segments correspond to bases 1 to 10, 2 to 11, 3 to 12 . . . and/or so on. For a 15-mer, the nucleic acid segments correspond to bases 1 to 15, 2 to 16, 3 to 17 . . . and/or so on. For a 20-mer, the nucleic acid segments correspond to bases 1 to 20, 2 to 21, 3 to 22 . . . and/or so on.

The nucleic acid(s) of the present invention, regardless of the length of the sequence itself, may be combined with other nucleic acid sequences, including but not limited to, promoters, enhancers, polyadenylation signals, restriction enzyme sites, multiple cloning sites, coding segments, and the like, to create one or more nucleic acid construct(s). The overall length may vary considerably between nucleic acid constructs. Thus, a nucleic acid segment of almost any length may be employed, with the total length preferably being limited by the ease of preparation or use in the intended recombinant nucleic acid protocol.

The term "vector" is used to refer to a carrier nucleic acid molecule into which a nucleic acid sequence can be inserted for introduction into a cell where it can be replicated. Vectors of the present invention are lentivirus based as described above and in other parts of the specification. The nucleic acid molecules carried by the vectors of the invention encode therapeutic genes and will be used for carrying out gene-therapies. One of skill in the art would be well equipped to construct such a therapeutic vector through standard recombinant techniques (see, for example, Maniatis et al., 1988 and Ausubel et al., 1994).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described below.

B. Multiple Cloning Sites

Vectors of the present invention can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

C. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997)

D. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

E. Polyadenylation Signals

In eukaryotic gene expression, one will typically include a polyadenylation signal to effect proper polyadenylation of the transcript. The nature of the polyadenylation signal is not believed to be crucial to the successful practice of the invention, and any such sequence may be employed. Some examples include the SV40 polyadenylation signal or the bovine growth hormone polyadenylation signal, convenient and known to function well in various target cells. Polyadenylation may increase the stability of the transcript or may facilitate cytoplasmic transport.

F. Origins of Replication

In order to propagate a vector of the invention in a host cell, it may contain one or more origins of replication sites (often termed "ori"), which is a specific nucleic acid sequence at which replication is initiated. Alternatively an autonomously replicating sequence (ARS) can be employed if the host cell is yeast.

G. Selectable and Screenable Markers

In certain embodiments of the invention, cells transduced with the lentivectors of the present invention may be identified in vitro or in vivo by including a marker in the expression vector. Such markers would confer an identifiable change to the transduced cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genetic constructs that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

9. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906). Furthermore, it is contemplated the control sequences that direct transcription and/or expression of sequences within non-nuclear organelles such as mitochondria, chloroplasts, and the like, can be employed as well. Control sequences comprising promoters, enhancers and other locus or transcription controlling/modulating elements are also referred to as "transcriptional cassettes".

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al., 2000). The promoters employed may be constitutive, tissue-specific, inducible, and/or useful under the appropriate conditions to direct high level expression of the introduced DNA segment, such as is advantageous for gene therapy or for applications such as the large-scale production of recombinant proteins and/or peptides. The promoter may be heterologous or endogenous.

Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Tables 1 lists non-limiting examples of elements/promoters that may be employed, in the context of the present invention, to regulate the expression of a RNA. Table 2 provides non-limiting examples of inducible elements, which are regions of a nucleic acid sequence that can be activated in response to a specific stimulus.

TABLE 1

Promoter and/or Enhancer

| Promoter/Enhancer | References |
| --- | --- |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-Dra | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |

TABLE 1-continued

| Promoter/Enhancer | References |
| --- | --- |
| γ-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $α_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| CD11b | Hickstein et al., 1992 |
| Gibbon Ape Leukemia Virus | Holbrook et al., 1987; Quinn et al., 1989 |

TABLE 2

Inducible Elements

| Element | Inducer | References |
| --- | --- | --- |
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | Poly(rI)x Poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |

TABLE 2-continued

Inducible Elements

| Element | Inducer | References |
|---|---|---|
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Non-limiting examples of such regions include the human LIMK2 gene (Nomoto et al., 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), DIA dopamine receptor gene (Lee, et al., 1997), insulin-like growth factor II (Wu et al., 1997), and human platelet endothelial cell adhesion molecule-1 (Almendro et al., 1996).

The lentiviral vectors of the present invention are designed, primarily, to transform cells with a therapeutic gene under the control of regulated eukaryotic promoters. Although the gp91-phox promoter is preferred, other promoter and regulatory signal elements as described in the Tables 1 and 2 above may also be used. Additionally any promoter/enhancer combination (as per the Eukaryotic Promoter Data Base EPDB) could also be used to drive expression of structural genes encoding the therapeutic gene of interest that is used in context with the lentiviral vectors of the present invention. Alternatively, a tissue-specific promoter for cancer gene therapy or the targeting of tumors may be employed with the lentiviral vectors of the present invention for treatment of cancers, especially hematological cancers.

Typically promoters and enhancers that control the transcription of protein encoding genes in eukaryotic cells are composed of multiple genetic elements. The cellular machinery is able to gather and integrate the regulatory information conveyed by each element, allowing different genes to evolve distinct, often complex patterns of transcriptional regulation. Activation or repression of the promoter and enhancer elements may be had through contacting those elements with the appropriate transcriptional activators or repressors, such as those described in FIG. 1B for the gp91-phox promoter and disclosed in Luo and Skalnik (1996) J. Biol. Chem. 271: 18203-210, and Luo and Skalnik (1996) J. Biol. Chem. 271: 23445-23451. With respect to the gp91-phox promoter, the activity of Interferon-gamma in modulating the transcription and expression of the expression cassette is an example of how such promoter or enhancer elements and the factors that interact with them may be employed in the practice of the present invention.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins. See, for example, the model for the regulation of the gp91-phox promoter presented in FIG. 1B.

Exemplary enhancers contemplated in the present invention are the DNAase HyperSensitive elements and their homologs described by Lien L L, Lee Y, Orkin S H, (1997) "Regulation of the myeloid-cell-expressed human gp91-phox gene as studied by transfer of yeast artificial chromosome clones into embryonic stem cells: suppression of a variegated cellular pattern of expression requires a full complement of distant cis elements," Mol Cell Biol. 17(4):2279-90. Under the influence of these enhancer elements, gene expression may be higher (due to enhancer activity HS) and less variegated (due to silencer activity of HS).

Analogs of the HS elements of gp91-phox are active in other promoter-enhancer systems. See, for example, May C, Rivella S, Callegari J, Heller G, Gaensler K M, Luzzatto L, Sadelain M, (2000) Therapeutic haemoglobin synthesis in beta-thalassaemic mice expressing lentivirus-encoded human beta-globin. Nature 406(6791):82-6, where analogous beta-globin HS elements were included into lentivector upstream of beta-globin promoter to drive expression of beta-globin cDNA.

Promoters and enhancers have the same general function of activating transcription in the cell. They are often overlapping and contiguous, often seeming to have a very similar modular organization. Taken together, these considerations suggest that enhancers and promoters are homologous entities and that the transcriptional activator proteins bound to these sequences may interact with the cellular transcriptional machinery in fundamentally the same way. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Aside from this operational distinction, enhancers and promoters are very similar entities. Constructs of elements that control transcription and expression may therefore be comprised of various elements arranged so as to provide means of control of enhanced utility and operation.

A signal that may prove useful is a polyadenylation signal (hGH, BGH, SV40). The use of internal ribosome binding sites (IRES) elements are used to create multigene, or polycistronic, messages. IRES elements are able to bypass the ribosome scanning model of 5'-methylated cap-dependent translation and begin translation at internal sites (Pelletier and Sonenberg, 1988). IRES elements from two members of the picornavirus family (polio and encephalomyocarditis) have been described (Pelletier and Sonenberg, 1988), as well as an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

In any event, it will be understood that promoters are DNA elements that when positioned functionally upstream of a gene leads to the expression of that gene. Most transgenes that will be transformed using the lentiviral vectors of the present invention are functionally positioned downstream of a promoter element.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

10. Brief Description of the Sequence Listings

SEQ ID NO: 1 provides the nucleotide sequence encoding a chimeric glycoprotein comprising a cytoplasmic tail domain derived from MLV-A and a transmembrane and extracellular domain derived from feline endogenous virus RD114.

SEQ ID NO:2 provides the amino acid sequence of the chimeric glycoprotein encoded by SEQ ID NO: 1.

SEQ ID NO:3 provides the nucleotide sequence encoding an alternate chimeric glycoprotein.

SEQ ID NO 4 provides the amino acid sequence of the chimeric glycoprotein encoded by SEQ ID NO: 3.

11. Examples

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

A. Materials and Methodology Employed in Examples 1-10

1. Cells.

The 293T human embryo kidney cell line (ATCC CRL-1573) and the TE671 human rhabdomyosarcoma cell line (ATCC CRL-8805) were grown in DMEM (Life Technologies, France) supplemented with 10% fetal calf serum (FCS).

Human and cynomolgus macaque (*Macaca fascicularis*) CD34$^+$ cells were obtained from mobilized blood and bone marrow samples, respectively, as described previously[26-28]. CD34$^+$ cells were recovered after Ficoll-Paque (Pharmacia, Sweden) gradient centrifugation and were purified with anti-CD34 M450 Dynabeads (Dynal, Norway). CD34$^+$ cell purity was over 95%.

Human and cynomolgus macaque peripheral blood mononuclear cells (PBMCs) were separated from fresh blood of healthy donors using a Ficoll-Hypaque/Percoll gradient (Pharmacia, Sweden), as described previously[29]. Peripheral blood lymphocytes (PBLs) were enriched from the PBMC fraction by overnight adherence at 37° C. to remove adherent monocytes and were monitored for CD3 marker expression (75-85% were CD3$^+$).

2. Antibodies

Anti-RD114 GP (ViroMed Biosafety Labs, USA) was a goat antiserum raised against the RD114 gp70 envelope glycoprotein (SU), used diluted to 1/5,000 for Western Blots. Anti-SIV CA (NIH AIDS Research and Reference Reagent Program, USA) was a mouse monoclonal antibody (2F12) raised against the SIVmac251 p27 capsid protein (CA), used diluted to 1/500 for Western Blots. Anti-MLV CA (ViroMed Biosafety Labs, USA) was a goat antiserum raised against the Rausher leukemia virus (RLV) p30 capsid protein (CA), used diluted to 1/10,000 for Western Blots.

3. Packaging and Transfer Vector Constructs.

The pSIV-12 packaging plasmid (FIG. 1) is a derivative of pSIV8[25] and expresses the SIVmac251 gag-pol genes under control of the hCMV promoter and an HIV-1 rev gene expression unit into which the two exons of rev have been fused and placed under control of the 3-hydroxy-3-methylglutaryl coenzyme A reductase (HMG) promoter, HMG intron I and the SV40 polyadenylation sequences. The pSIV-T1$^+$ plasmid[30] encodes a packaging-competent SIVmac251-based vector that expresses the enhanced green fluorescent protein (GFP) marker gene under control of the CMV promoter (FIG. 1).

The pSIV-T1$^+$ plasmid encodes a packaging-competent SIVmac251-based vector that expresses the enhanced green fluorescent protein (GFP) marker gene under control of the CMV promoter. The pTG5349 murine leukemia virus (MLV) packaging plasmid and the pTG13077 plasmid, encoding an MLV-based vector containing a CMV-GFP internal transcriptional unit, were kindly provided by Transgene SA (Strasbourg, France).

4. Viral Glycoprotein Expression Constructs.

The following plasmids, phCMV-G[31], EboV-GP (kind gift of V. Volchkov), phCMV-HA[32], phCMV-10A1[33] and phCMV-GALV[33] encode the vesicular stomatitis virus (VSV) G protein, the glycoprotein of the Zaire strain of Ebola Virus (EboV), the fowl plague virus (FPV) H7-HA hemagglutinin, the MLV-10A1 and the gibbon ape leukemia virus (GALV) envelope glycoproteins, respectively. All glycoproteins were expressed under control of the same cis-acting signals: CMV promoter, rabbit β-globin intron II and polyadenylation sequences (FIG. 1).

phCMV-G was used as a backbone to express the glycoproteins derived from the feline endogenous virus RD114 (Genbank X87829[34]) and the 4070A strain of amphotropic MLV (MLV-A[35]). The phCMV-RD114 expression vector, expressing the RD114 virus envelope glycoprotein (RD114 GP), and the phCMV-GALV construct were further modified to express the RD114/TR (FIG. 2B) and GALV/TR[8,13,15] chimeric glycoproteins carrying the MLV-A GP cytoplasmic tail.

Figure 7:
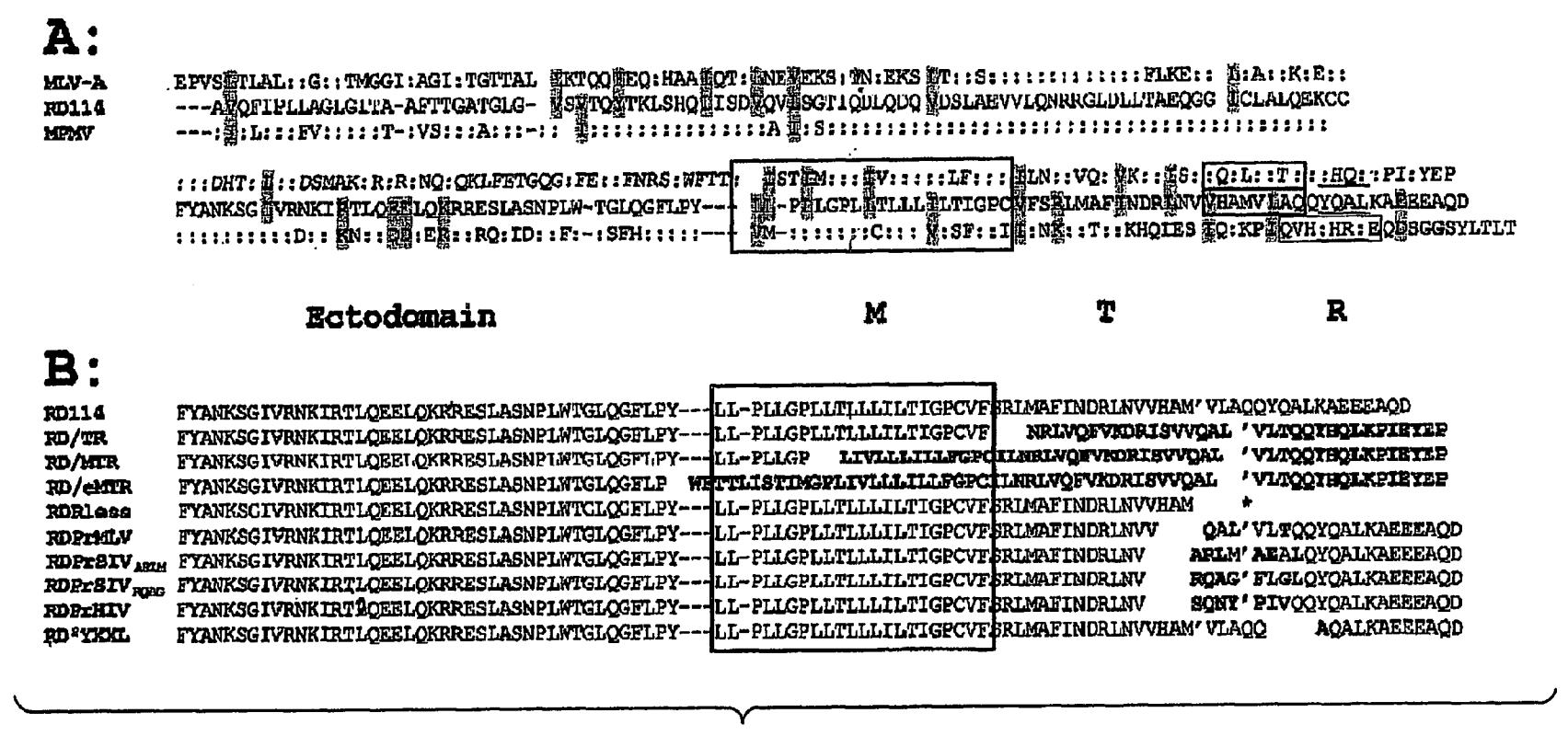

The phCMV-RD expression vector, expressing the RD114 virus envelope glycoprotein (RD114 GP), was further modified to generate a series of mutants that harbour modifications in the RD114 GP transmembrane domain (TMD) and/or cytoplasmic tail (CT). All subsequent constructs were generated by PCR-mediated and oligonucleotide site-directed mutagenesis (details and sequences are available upon request) and cloned in the phCMV-RD plasmid. The amino-acid sequences of the carboxy-terminal portions of the mutant RD114 GPs are shown in FIG. 7.

5. Syncytia Assays.

The HeLa cells used for the fusion assay were stable transfectants of either a β-galactosidase gene (LacZ) under the control of the HIV-1 long terminal repeat (LTR), whose expression is Tat-dependent (HeLaCD4LTRLacZ cells), or were constitutively expressing the Tat protein of HIV-1 (Hela-Tat cells), as described previously (9). Envelope-mediated fusion was quantified essentially as described previously (9, 16). In this assay, the HIV-1 LTR-driven expression of β-galactosidase is transactivated by the Tat protein upon fusion of envelope-expressing cells with receptor-bearing indicator cells. Twenty-four hours prior to transfection, $5\times10^4$ HeLaCD4LTRLacZ cells were seeded per twelve-well plates. Viral glycoprotein expression constructs were transfected into the HeLa cells described above using a calcium-phosphate transfection protocol (Clontech, France) according to the manufacturer's recommendations using 1 µg of plasmid. 24 hours post-transfection, $10^5$ indicator Hela-Tat cells were cocultivated with the viral glycoprotein-presenting cells for 36 to 48 hours. Cell-cell fusion was measured following fixation with 0.5% (weight/volume) glutaraldehyde in PBS (phosphate buffer saline), washed with PBS, and stained by incubation in a 5-bromo-4-chloro-3-indolyl-β-D-galactopyranoside (X-Gal) solution as described previously (9, 16). Blue syncytia, indicating fusion between the envelope-presenting and Tat-containing indicator cells, were counted regardless of the number of nuclei per syncytia.

6. Production of Retroviral Vectors.

Pseudotyped SIV-derived vectors were generated as previously described[25] by transient transfection of 293T cells. The pSIV-T1+ vector construct (8.1 µg), the pSIV-12 packaging construct (8.1 µg), and the viral glycoprotein-expression construct (2.7 µg) were used to co-transfect 293T cells seeded the day before in 10 cm plates. The medium (12 ml/plate) was replaced 16 hrs after transfection, and supernatant was harvested 24 hrs later. Concentration of the vector particles was performed by pelleting the virions in 26-ml ultracentrifugation tubes, which were spun for one hr at 32,000 rpm at 4° C. in a 70Ti Beckman rotor. Viral pellets were re-suspended in serum-free DMEM supplemented with 1% bovine serum albumin (BSA) in 1/100 of the initial volume of the viral supernatant, aliquoted and stored at −80° C.

Pseudotyped MLV-derived vectors were generated in a similar manner by transient transfection of the pTG5349 MLV packaging construct (8.1 µg), of the pTG13077 MLV vector construct (8.1 µg) and of the glycoprotein-expressing construct (2.7 µg). Plasmid DNAs were transfected into $2.5\times10^6$ 293T cells seeded the day before in 10 cm plates using a calcium-phosphate transfection protocol (Clontech, France) according to the manufacturer's recommendations. The medium (8 ml/plate) was replaced 16 hrs after transfection, and supernatant was harvested 24 hrs later and filtered through 0.45 µm-pore-sized membranes.

7. Immunoblots and Viral Incorporation of the Glycoproteins.

Virus producer cells were lysed in a 20 mM Tris-HCl buffer (pH 6.5) containing 1% Triton-X100, 0.05% SDS (sodium dodecyl-sulfate), 5 mg/ml sodium deoxycholate, 150 mM NaCl, and 1 mM PMSF. Lysates were incubated for 10 min at 4° C. and were centrifuged for 5 min at 13,000×g to pellet the nuclei. Supernatants were then frozen at −80° C. until further analysis. Purified virus samples were obtained by ultracentrifugation of viral supernatants (8 ml) through a 1.5-ml 20% sucrose cushion in a SW41 Beckman Rotor (25,000 rpm, 2.5 hrs, 4° C.). Viral pellets were suspended in 100 µl of PBS, and frozen at −80° C.

Samples (30 µg for cell lysates, or 20 µl for purified viruses) were mixed 5:1 (vol:vol) in a 375 mM Tris-HCl (pH 6.8) buffer containing 6% SDS, 30% β-mercapto-ethanol, 10% glycerol, and 0.06% bromophenol blue, boiled for 5 min, then run on 9% SDS-PAGE. After protein transfer onto nitrocellulose filters, immunostaining was performed in TBS (Tris-base saline, pH 7.4) with 10% milk powder and 0.1% TWEEN. The blots were probed with the relevant antibody and developed using HRPO-conjugated Ig (immunoglobulins) raised against the species of each primary antibody (DAKO, UK) and an enhanced chemiluminescence kit (Amersham Life Science).

8. Metabolic Labeling and Immunoprecipitation.

Twelve hours after transfection with the different onco-retroviral or lentiviral vector component, virus producer cells were starved in cysteine- and methionine-free culture medium for 1 h and labeled at 37° C. for 16 hrs in 3 ml of cysteine- and methionine-free DMEM containing 100 µCi of $^{35}$S-cysteine and $^{35}$S-methionine (ICN) per ml and 2% dialysed fetal calf serum. Cells were lysed and immunoprecipitated as previously described (9) with a goat anti-RD114 SU serum. For analyses of the processing of the cytoplamsic tail of the TM GP subunit, the supernatant of virus producer cells were harvested and filtered through a 0.45-mm-pore-size filter. Supernatants were ultracentrifuged on a 2-ml 20% sucrose cushion for 2 hrs at 30,000 rpm in an SW41 rotor (Beckman). The pellets were lysed by adding 150 ml of lysis buffer (50 mM Tris HCl (pH 7.5), 15 mM NaCl, 5 mM MgCl2, 5 mM KCl, 1% Triton X-100, 0.5% sodium deoxycholate). One-fifth of the lysate was preserved and electrophoresed as such for a crude analysis of the virus protein content by western-blotting, whereas the remaining lysate was submitted to immunoprecipitation with anti-RD114 SU antibodies. Immunoprecipitates were electrophoresed in sodium dodecyl sulfate (SDS)—12% polyacrylamide gels under reducing conditions to dissociate the co-immunoprecipitated TM GP subunit from the SU.

9. Infection Assays.

Determination of transduction efficiencies and infectious titers was performed as detailed previously[25], using TE671 as target cells. Stability of vector pseudotypes in human or macaque sera was examined by titrating surviving viral particles after incubation in 1:1 mixtures (volume:volume) of virus preparations with fresh sera for 1 hr at 37° C., as previously described[36]. Approximately $5\times10^4$ GFP infectious units of pseudotyped vector particles were used per point. Sera were harvested from healthy blood donors and conditioned as published[36]. Stability of virions was determined as the percentage of infectivity of primate serum-treated viruses versus fetal calf serum-treated viruses. Heat-inactivated sera (56° C., 1 hr) were used as controls.

TE671 target cells were seeded at a density of $3\times10^5$ cells per well in 6-well plates one day prior transduction. Serial dilutions of vector preparations were added to the cells in the presence of 6 µg/ml of polybrene, and the cultures were incubated for 4 hrs at 37° C. The vector-containing medium was then replaced with normal culture medium and the cells were incubated for 72 hrs at 37° C. The transduction efficiency, determined as the percentage of GFP-positive cells, was measured by FACS analysis following individualization of the transduced cells in trypsin and their re-suspension in PBS. The infectious titres, provided as infectious units (i.u.)/ml, were calculated by using the formula: Titre=% inf×(3× $10^5$/100)×d; where "d" is the dilution factor of the viral supernatant and "% inf" is the percentage of GFP-positive cells as determined by FACS analysis using dilutions of the viral supernatant that transduce between 1% and 5% of GFP-positive target cells.

10. Transduction of Primary Cells.

Purified CD34$^+$ cells were incubated overnight in 12-well plates at 2×10$^6$ cells/well in 2 ml of StemSpan SFEM medium supplemented with antibiotics (StemCell Technologies, Meylan, France) and with 10 ng/ml of thrombopoietin (TPO; Peprotech Inc, London, UK). Pre-activated CD34$^+$ cells were then seeded in 96-well plates (10$^4$/well) and were transduced with the pseudotyped vectors in a total volume of 200 µl StemSpan medium containing TPO and 6 µg/ml of polybrene. Variable multiplicities of infection (MOIs), determined using TE671 target cells, were applied to the target cells and were in the range of 0.5 to 60 infectious particles/target cell. Transduction in retronectin-coated wells (CH-296; Takara Shuzo, Japan) was performed using the same protocol in 96-well plates pre-coated for 2 hrs with 8 µg retronectin/well. After 16 hours, CD34$^+$ cells were washed, suspended in 400 µl of StemSpan medium supplemented with 10% fetal calf serum (Life Technologies, France), with antibiotics, and with 10 ng/ml of Flt3-L, TPO, and stem cell factor (SCF) for 3 days. GFP expression was analyzed by FACS analysis 5 days post-infection.

Human and macaque PBLs were pre-activated for 24 hr before infection as described previously by adding 1 µg of anti-CD3 (HIT3a, Pharmingen) and anti-CD28 (CD28.2, Pharmingen) antibodies to 1 ml of medium containing 2×10$^6$ human PBLs[29] or by adding 5 ng/ml of concanavalin A and 10 ng/ml of IL2 to 2×10$^6$ macaque PBLs[37]. For transduction, 10$^5$ activated PBLs were mixed with the pseudotyped vectors in a total volume of 1 ml of PBL medium supplemented with 6 µg/ml of polybrene, for 4 hrs at 37° C. After infection, cells were washed in PBS and incubated at 37° C. for 5 days in RPMI-1640 (Life Technologies, France) supplemented with IL2 until transduction efficiency was determined by FACS analysis.

B. Examples 1-10

Example 1

Ability of Different Viral Glycoproteins to Pseudotype an SIV Vector

We examined a panel of viral glycoproteins (GPs) for their ability to pseudotype lentiviral vectors derived from simian immunodeficiency virus (SIVmac251). These glycoproteins were derived from type C mammalian retroviruses, such as the Env GPs of the feline endogenous retrovirus RD114, the amphotropic murine leukemia virus (MLV-A), the MLV-10A1 and the gibbon ape leukemia virus (GALV), or from membrane-enveloped viruses, such as the fowl plague virus (FPV hemagglutinin—FPV-HA), the lymphocytic choriomeningitis virus (LCMV), Ebola virus (EboV), and vesicular stomatitis virus (VSV) GPs. Pseudotyped SIV vectors were generated by transient expression in 293T cells transfected with three plasmids (FIG. 1) encoding the SIV viral core proteins, an SIV-based transfer vector harboring the GFP marker gene, and the different GPs. Infection assays on TE671 human rhabdomyosarcoma cells indicated that titers higher than 10$^5$ i.u./ml were obtained for vectors generated with the GPs of VSV, LCMV, MLV-A and MLV-10A1 (FIG. 2A). In contrast, vectors generated with the GPs of EboV and FPV had low titers, of less than 5×10$^3$ i.u./ml. SIV vectors generated with the GPs of GALV and RD114 had intermediate titers, between 10$^4$ and 5×10$^4$ i.u./ml. These relative differences in infectivity of the pseudotyped vectors were reproduced on other target cells such as 293T cells (data not shown), suggesting that determination of the infectious titers on TE671 cells reflected the capacity of the different GPs to pseudotype SIV cores.

The infectious titers obtained with SIV vectors generated with the GPs of FPV, GALV and RD114 were surprisingly low in comparison to those achieved with MLV vectors pseudotyped with the same glycoproteins[21,34,38]. Since budding of lentiviral core particles is not dependent on the expression of viral glycoproteins[39], this suggested that the virions could not efficiently incorporate these GPs or, alternatively, that they could not egress from producer cells after GP assembly. Indeed, when vector-producer cells expressing the FPV-HA were treated with neuraminidase, infectivity of HA-pseudotyped vectors was strongly increased by up to 100 fold (FIG. 2A). This enhancement correlated with a 50-fold increased production of viral particles in the supernatant of producer cells (data not shown). This was most likely induced by neuramimidase-mediated release of virions from the cell surface on which they were retained because of binding to sialic-acid-containing cell-surface molecules[40,41]. However, such a defect in virion egress could not explain the lack of infectivity of SIV vectors generated with the GALV and RD114 GPs since the titers of MLV vectors pseudotyped with the latter glycoproteins are generally high[21,34]. This suggested, rather, a defect at the level of GP incorporation on the lentiviral cores. Previous studies have indicated that the cytoplasmic tail of mammalian type C retroviruses bears elements that control the formation and/or infectivity of pseudotypes with primate lentiviruses[8,13-15]. Since the MLV-A GP efficiently pseudotypes lentiviral vectors (FIG. 2A), we hypothesized that its cytoplasmic tail should contain all the elements required for optimal GP incorporation on lentiviral particles. Indeed, replacement of the cytoplasmic tail of RD114 (FIG. 2B) and GALV GPs with that of MLV-A GP resulted in strongly increased incorporation of either glycoprotein on lentiviral cores, as shown in FIG. 2C for the RD114 GP and elsewhere for the GALV GP[8,13,15]. These chimeric GALV and RD114 GPs, named GALV/TR and RD114/TR, preserved the host-range of the initial glycoproteins, as assessed on receptor-interference assays (data not shown), and conferred 25 fold increased titers to the SIV vectors (FIG. 2A).

Example 2

Characterization of Pseudotyped SIV-Based Vector Stocks

We sought to characterize the properties of vectors coated with the modified or unmodified viral glycoproteins that efficiently pseudotyped the SIV vector particles. The SIV vector pseudotypes were concentrated by ultracentrifugation, resuspended in a storage buffer containing 1% BSA, aliquoted and stored at −80° C. prior to infection assays. Although vectors coated with MLV-10A1 GP had fair titers before concentration, they were not used in the further analyses because they could not be efficiently concentrated (data not shown). In contrast, vectors pseudotyped with FPV-HA, VSV-G or with the GALV/TR, RD114/TR, MLV-A and LCMV glycoproteins were very efficiently concentrated, allowing recovery of more than 80%, on average, of the infectious particles after a 100-fold concentration of the physical particles (data not shown). As vectors pseudotyped with the FPV-HA and LCMV glycoproteins failed to transduce the primary hematopoietic cells tested here (i.e., PBLs and CD34+ cells; data not shown), they were not analyzed further. Infectious titers of the concentrated stocks of vectors pseudotyped with the remaining glycoproteins (i.e., MLV-A, GALV/TR, RD114/TR and VSV-G) were determined using TE671 target cells and were in the range of $5 \times 10^6$ for the less infectious pseudotypes, obtained with GALV/TR GP, to $1 \times 10^8$ i.u./ml for the most infectious one, obtained with VSV-G (FIG. 3A). Similar differences in titers between the vector pseudotypes were detected on other human adherent cell lines (data not shown). This indicated that titer determination using the highly permissive TE671 cells reflected the evaluation of the specific infectivity of pseudotyped vectors. Importantly, the number of infectious particles correlated with the presence of physical particles. As shown in FIG. 3B, within a given preparation of pseudotyped vectors, similar amounts of virion-associated capsid proteins were detected for the vector pseudotypes that gave the highest titers (VSV-G and MLV-A or RD114/TR GPs). Lower amounts of physical particles were reproducibly detected for virions pseudotyped with GALV/TR GPs, in agreement with their lower titers (FIG. 3A). However, important differences in the absolute quantities of virion-associated capsid proteins were noticed when two independent vector preparations were compared, despite comparable infectious titers (data not shown). Thus, to minimize artifacts due to differences in the quality of vectors stocks, each subsequent evaluation experiment was conducted using pseudotyped vectors generated concurrently. Moreover, since the detection of virion-associated capsid proteins did not appear to be a valid indicator of infectious particles and precluded comparison of results, normalization of the pseudotyped vector stocks was performed using titers determined on TE671 cells.

Example 3

Stability of Vector Pseudotypes in Primate Sera

Vectors suitable for in vivo gene delivery should be stable at 37° C. and should retain high infectivity in primate sera. The stability of the vector pseudotypes was therefore determined by comparing titers of viral particles incubated for one hour at 37° C. versus 4° C. Lentiviral vectors pseudotyped with RD114/TR GP or VSV-G were stable at 37° C., with more than 85% of the vector particles remaining infectious after incubation at 37° C. (data not shown). In comparison, vectors pseudotyped with MLV-A and GALV/TR GPs lost more than 75% of infectivity following incubation at 37° C. (data not shown), suggesting that the latter GPs incorporated into lentiviral core particles were temperature-sensitive.

The stability of the pseudotyped vectors in human and cynomolgus macaque sera was evaluated. The same quantities of pseudotyped infectious particles were mixed with fresh primate sera at a ratio of 50/50 (v/v) and incubated for one hr at 37° C. Heat-inactivated primate sera as well as fetal calf serum (FCS) were used as controls. The results, represented as the percentages of residual infectivity after incubation in fresh or heat-inactivated primate sera relative to the infectivity of FCS-incubated virions (100%), are shown in FIG. 4. The VSV-G-pseudotyped vectors were inactivated by both human and macaque sera, resulting in more than 90% degradation of viral particles. Vectors pseudotyped with the retroviral glycoproteins were significantly more resistant in human sera, although their levels of resistance were variable according to the serum sample tested and the type of retroviral GP. Vectors pseudotyped with MLV-A glycoproteins were stable in human serum but were relatively sensitive to inactivation by macaque serum. Vectors coated with GALV/TR GP displayed variable levels of stability in human and macaque sera. In contrast, lentiviral vectors pseudotyped with the RD114/TR GP exhibited complete stability in all human sera tested (FIG. 4A) and presented good stability in macaque sera (FIG. 4B).

Example 4

Transduction of Human and Macaque Primary Hematopoietic Cells

We next compared the different vector pseudotypes for their capacity to transduce primary hematopoietic cells such as CD34+ cells and PBLs. Human CD34+ cells derived from mobilized blood were pre-activated overnight in serum-free medium supplemented with TPO and were transduced for 16 hours with a single-hit of SIV vectors pseudotyped with the MLV-A, GALV/TR, RD114/TR or VSV-G glycoproteins. Variable multiplicities of infection (MOIs), as determined using infectious titers assessed on TE671 cells, were used to transduce the CD34+ cells. Side-by-side transductions experiments were performed in the presence, or in the absence, of CH-296 retronectin fragment[42-44]. After infection, cells were grown for 5 days in the presence of low concentrations of TPO, SCF and Flt3-L. GFP expression was readily detected in the transduced cells by flow cytometry, allowing us to evaluate the influence of the MOIs and the pseudotyping GP on transduction efficiency (FIG. 5A). For transduction in the absence of retronectin, the percentage of GFP+ cells initially increased as a direct function of the MOI and the curves flattened at MOIs comprised between 2 and 20, reaching a maximum of 25% GFP+ cells. These moderate transduction efficiencies were likely due to the sub-optimal infection protocol, and specifically the single and short incubation of target cells with virions. In these experimental conditions, the most efficient vectors were those pseudotyped with the VSV-G glycoprotein (mean GFP+ cells: 24.75%±3.23%; n=5), although, at MOIs lower than 2, SIV vectors pseudotyped with GALV/TR and MLV-A GPs exhibited a transduction efficiency higher than that of VSV-G-pseudotyped vectors (see inset in FIG. 5A). However, at the most efficient MOIs tested, vectors generated with the MLV-A, GALV/TR and RD114/TR glycoproteins achieved 5 to 12-fold lower transduction efficiencies than VSV-G-pseudotypes (FIG. 5A). The relatively low titers of vectors generated with the GALV/TR GP (FIG. 3A) did not allow transduction efficiency to be evaluated at high MOIs. Divergent results were obtained when infections of CD34+ cells were performed on retronectin-coated plates (FIG. 5A). Under these conditions, the VSV-G-pseudotyped vectors retained the same maximal transduction efficiency (24.56%±3.27% GFP+ cells; n=5) than in the absence of retronectin, in agreement with results of others[45]. In contrast, the RD114/TR-pseudotyped vectors exhibited a 10-fold increased transduction efficiency, reaching up to 65% GFP+ cells (mean: 51.30%±8.74%; n=5), indicating that the combined use of RD114/TR GP and retronectin synergistically enhanced infection. The retronectin also enhanced the transduction efficiency of vectors pseudotyped with GALV/TR and MLV-A GPs, yet with a much lower magnitude compared to vectors pseudotyped with RD114/TR GP (FIG. 5A).

We then transduced macaque CD34+ cells derived from bone marrow with the pseudotyped vectors (FIG. 5B). In the absence of retronectin, the best pseudotyping GP was VSV-G, allowing transduction of up to 26% GFP+ cells (21.7%±3.51%; n=5). SIV vectors pseudotyped with the GALV/TR and with the MLV-A GPs were the less efficient to transduce macaque CD34⁺ cells (maximal transduction efficiency of 3% GFP⁺ cells). Compared to vectors pseudotyped with VSV-G, the RD114/TR GP-pseudotyped vectors resulted in about 2-fold less efficient transduction (10.12%±1.26%, n=4). The presence of retronectin during transduction did not improve the efficiency of transduction by VSV-G-pseudotyped vectors (FIG. 5B). However, in a manner similar to transduction of the human CD34⁺ cells, retronectin enhanced transduction of macaque CD34⁺ cells by lentiviral vectors pseudotyped with MLV-A and RD114/TR GPs. Under these conditions, maximal levels of transduction of up to 30% GFP⁺ cells (24.23%±4.15%, n=5) could be obtained with RD114/TR-pseudotyped vectors (FIG. 5B).

Figure 6:
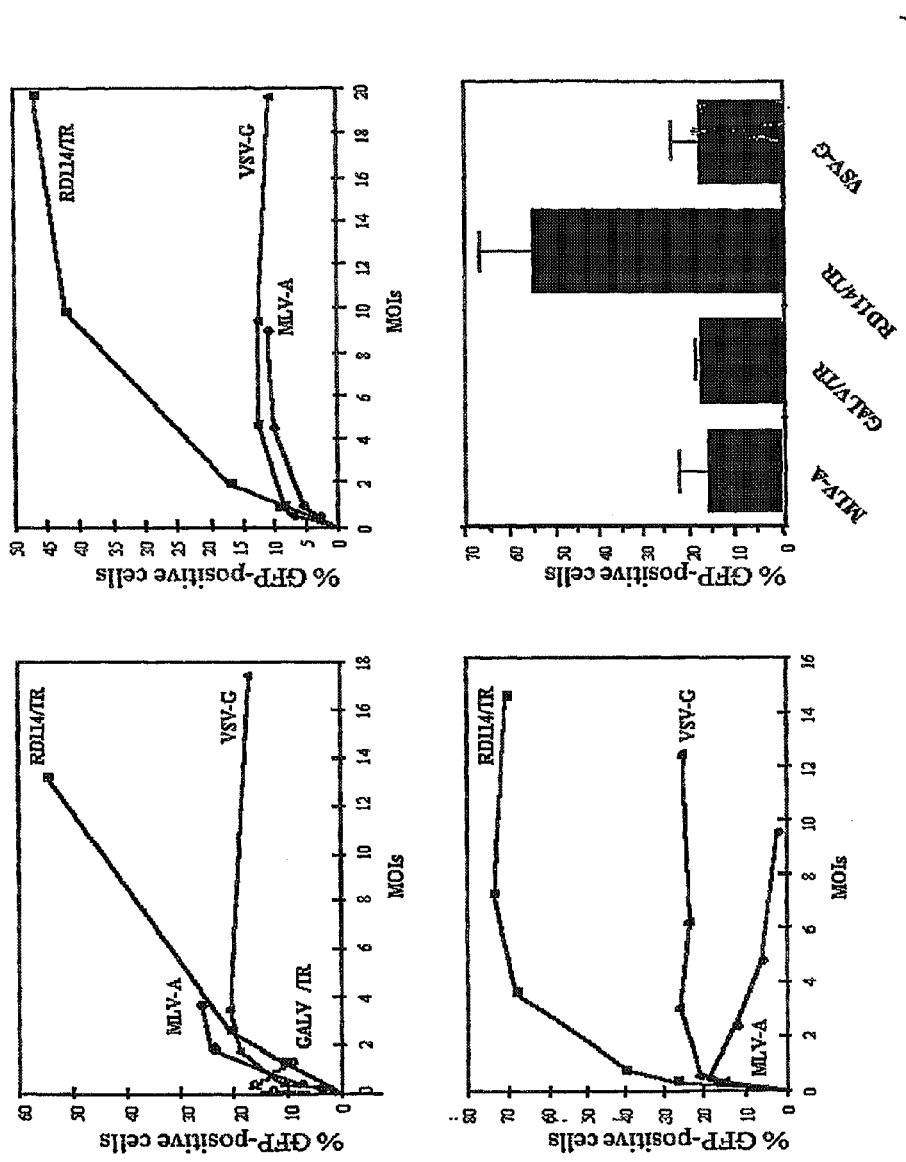
FIG. 6A. Transduction of human peripheral blood lymphocytes. Peripheral blood lymphocytes (PBLs) of human origins were transduced with the indicated SIV-vector pseudotypes at different multiplicities of infection (MOIs). Human PBLs were activated with soluble anti-CD3 and anti-CD28 antibodies for 24 hours. Macaque PBLs were activated with concanavalin A and rhIL2 for 2 days prior to infection. Activated PBLs were infected for 4 hrs with SIV vectors pseudotyped with VSV-G (triangles), MLV-A GP (closed circles), GALV/TR GP (open circles) or RD114/TR GP (closed squares). Infected cells were washed in PBS, grown in PBL culture medium and transduction efficiency was assessed five days post-infection. The results of experiments performed with PBLs from different donors are shown, as well as the statistical analyses of the maximal transduction efficiencies of at least four experiments performed with PBLs derived from different donors and stocks of pseudotyped vectors.
FIG. 6B. Transduction of macaque peripheral blood lymphocytes. Peripheral blood lymphocytes (PBLs) of cynomolgus macaque origins were transduced with the indicated SIV-vector pseudotypes at different multiplicities of infection (MOIs). Human PBLs were activated with soluble anti-CD3 and anti-CD28 antibodies for 24 hours. Macaque PBLs were activated with concanavalin A and rhIL2 for 2 days prior to infection. Activated PBLs were infected for 4 hrs with SIV vectors pseudotyped with VSV-G (triangles), MLV-A GP (closed circles), GALV/TR GP (open circles) or RD114/TR GP (closed squares). Infected cells were washed in PBS, grown in PBL culture medium and transduction efficiency was assessed five days post-infection. The results of experiments performed with PBLs from different donors are shown, as well as the statistical analyses of the maximal transduction efficiencies of at least four experiments performed with PBLs derived from different donors and stocks of pseudotyped vectors.
Figure 6:
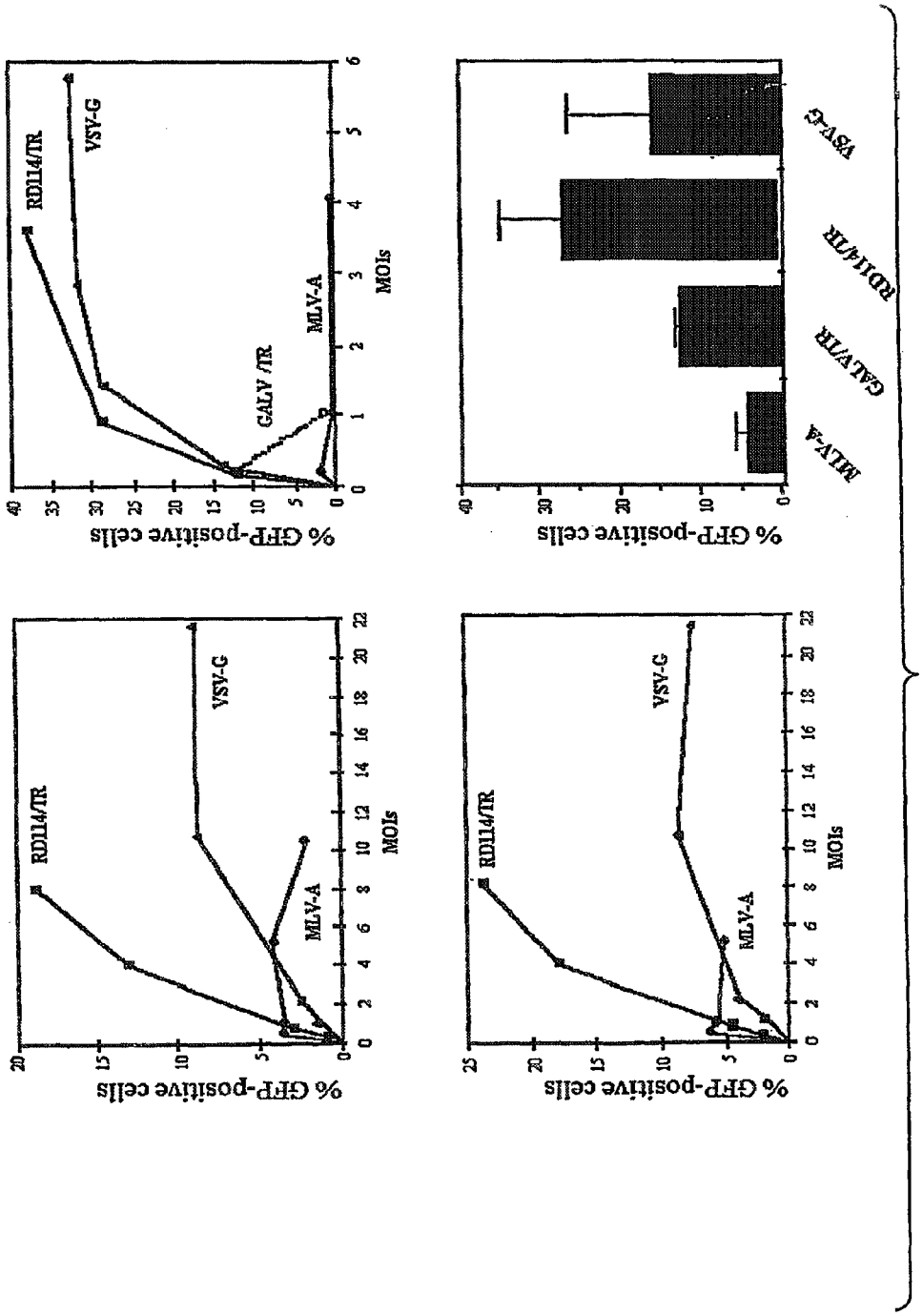

We then determined the transduction efficiencies of the pseudotyped SIV vectors in human and macaque PBLs. PBLs, isolated from fresh blood, were incubated for 4 hours with the vectors in the absence of retronectin. Pre-activation of the PBLs for 24 hrs with soluble anti-CD3 and anti-CD28 antibodies was necessary for transduction with lentiviral vectors, as previously reported[26,29,46]. As a result of these experimental conditions that favored stimulation and survival of CD3⁺ cells, transduction of PBLs was oriented to T cells. GFP expression, determined at 5 days post-infection (FIG. 6), showed that transduction of the PBLs was dependent on the MOI. At low MOIs, the percentages of GFP⁺ cells steadily increased for the different vector pseudotypes until reaching plateaus. The MOIs required for reaching these plateaus varied with the vector pseudotype. The plateaus of transduction were quickly reached at MOIs of less than 5 infectious particles per cell for lentiviral vectors pseudotyped with VSV-G, with MLV-A GP or with GALV/TR GP (FIG. 6A). In contrast, the threshold MOI necessary to reach a plateau with RD114/TR GP-pseudotyped virions was of about 5-10 infectious particles per cell (FIG. 6A). Interestingly, the maximal transduction levels also varied with the vector pseudotype tested. VSV-G-pseudotyped vectors only transduced a maximum of 10-23% of T cells (mean: 16.87%±6.53%; n=4). This somewhat low level of transduction is in agreement with our previous results[26] obtained with a VSV-G-pseudotyped HIV-1-derived vector of the same generation and design as the SIV-T1⁺ vector used in this report. In contrast, much higher levels of transduction, reaching 50-75%, were achieved with vectors pseudotyped with the RD114/TR chimeric GP (55.04%±11.74%; n=4). Maximal transduction efficiencies obtained with the other pseudotyped vectors remained low although, as mentioned above, the low titers of vectors coated with the GALV/TR chimeric GP did not allow us to assay for MOIs higher than 2. Additionally, for some vector preparations, the transduction efficiency was found to decrease when high MOIs of MLV-A GP or GALV/TR GP-pseudotyped SIV vectors were used to transduce the human PBLs (FIG. 6A). This effect was probably due to competition for receptor binding induced by an excess of defective particles or by soluble GP "shed" from viral particles, as suggested in recent studies[44,47].

Similar results were obtained for transduction of macaque PBLs, although the threshold MOIs necessary to reach the plateaus of infection seemed higher than those necessary for human PBLs and the maximal levels of transduction were lower than those obtained with human PBLs (FIG. 6B). Transduction efficiencies obtained with vector particles pseudotyped with GALV/TR or MLV-A GPs remained very low (less than 4-12% GFP⁺ cells) and were found to decrease at MOIs higher than 1. In comparison to vectors pseudotyped with these latter GPs or with VSV-G (15.32%±10.06%; n=4), PBL transduction with RD114/TR GP-pseudotyped vectors was facilitated. Up to 40% of GFP⁺ cells could be transduced (26.86%±8.07%; n=4) although higher transduction levels might clearly be expected when using MOIs superior to those applied in these experiments.

Altogether these results indicated that the RD114/TR glycoprotein was particularly potent to allow transduction of primate CD34⁺ cells and PBLs with pseudotyped SIV vectors, although the RD114/TR GP-pseudotyped SIV vectors required the retronectin CH-296 fragment for optimal transduction of short-term stimulated CD34⁺ cells.

Example 5

Design of RD114 GP Cytoplasmic-Tail Mutants

As determined by the morphology of its intracellular core particle, the feline endogenous virus RD114 is a type C mammalian retrovirus (32). However its GP is typical of that of simian type D retroviruses (28), with which it shares the same cell surface receptor, RDR (31, 38), and bears significant homology with the GP of MPMV (Mason-Pfizer monkey virus), in the TM subunit, in particular (FIG. 7). In a previous report, we have found that the RD114 feline endogenous virus glycoprotein did not allow efficient pseudotype formation with lentiviral cores (35). Here we sought to investigate the determinants of the RD114 GP that restrict pseudotyping with lentiviral vectors derived from SIV (simian immunodeficiency virus).

Recent studies have indicated that the transmembrane domain and/or cytoplasmic tail of mammalian type C retroviruses bear elements that control formation and/or infectivity of pseudotypes with HIV-1 vectors (4, 34, 36). Such elements might possibly influence the infectivity of viral particles at different levels: i) cellular co-localisation of the GP and viral cores necessary for viral assembly, ii) GP interactions with viral core proteins that condition GP incorporation, and iii) activation of GP fusogenicity through cleavage of its cytoplasmic tail by the retroviral protease during or shortly after virion budding. The GPs of both amphotropic MLV (MLV-A) and RD114 efficiently pseudotypes MLV core particles (6, 39). Therefore, since the GP of MLV-A also efficiently pseudotypes SIV viral cores (24, 35), we assumed that it should contain elements that optimally control the assembly and/or infectivity of SIV vector pseudotypes, in contrast to those carried by the RD114 GP. Thus, to define determinants that restrict the capacity of the RD114 GP to pseudotype lentiviral core particles, we generated a panel of RD114 GP mutants into which sub-regions derived from its trans-membrane domain (TMD) and/or its cytoplasmic tail (CT) were replaced by their counterparts derived from MLV-A GP (FIG. 7B). Mutant RD/TR was generated to address the importance of the MLV CT itself. Mutants RD/MTR and RD/eMTR carried the MLV TMD in addition to the MLV CT. The RDRless GP was a truncated version of RD114 GP and was generated by insertion of a stop codon at a position corresponding to a putative cleavage site of its CT (see below). Mutant RDPrMLV harbored replacement of the putative RD114 CT cleavage site with that of MLV GP. The cytoplasmic tails of the other mutants, RDPrSIV$_{ARLM}$, RDPrSIV$_{ROAG}$ and RDPrHIV, contained substrates for the SIVmac or HIV-1 core proteases, which were respectively derived from cleavage sites found in the Gag proteins of SIVmac251 or of HIV-1. Finally, mutant RDΔYXXL was designed to evaluate the importance of a putative tyrosine endocytosis motif carried by the RD114 CT, which might influence GP localisation, cell-surface expression and/or fusogenicity. The influence of this motif has been well characterised for other retroviral GPs (1, 13, 19).

Production of all GP mutants was achieved using identical expression-vectors under control of a CMV promoter. 293 producer cells were co-transfected with plasmids encoding the components of vector particles, i.e., the viral core proteins, the transfer vector and either of the different GPs. No variations in the quantities of either core proteins or GPs were detected, as monitored by immuno-blotting of cell lysates using anti-RD114 SU antibodies (data not shown).

Example 6

Modifications of the RD114 GP Cytoplasmic Tail Alter Cell-Cell Fusogenicity

Figure 8:
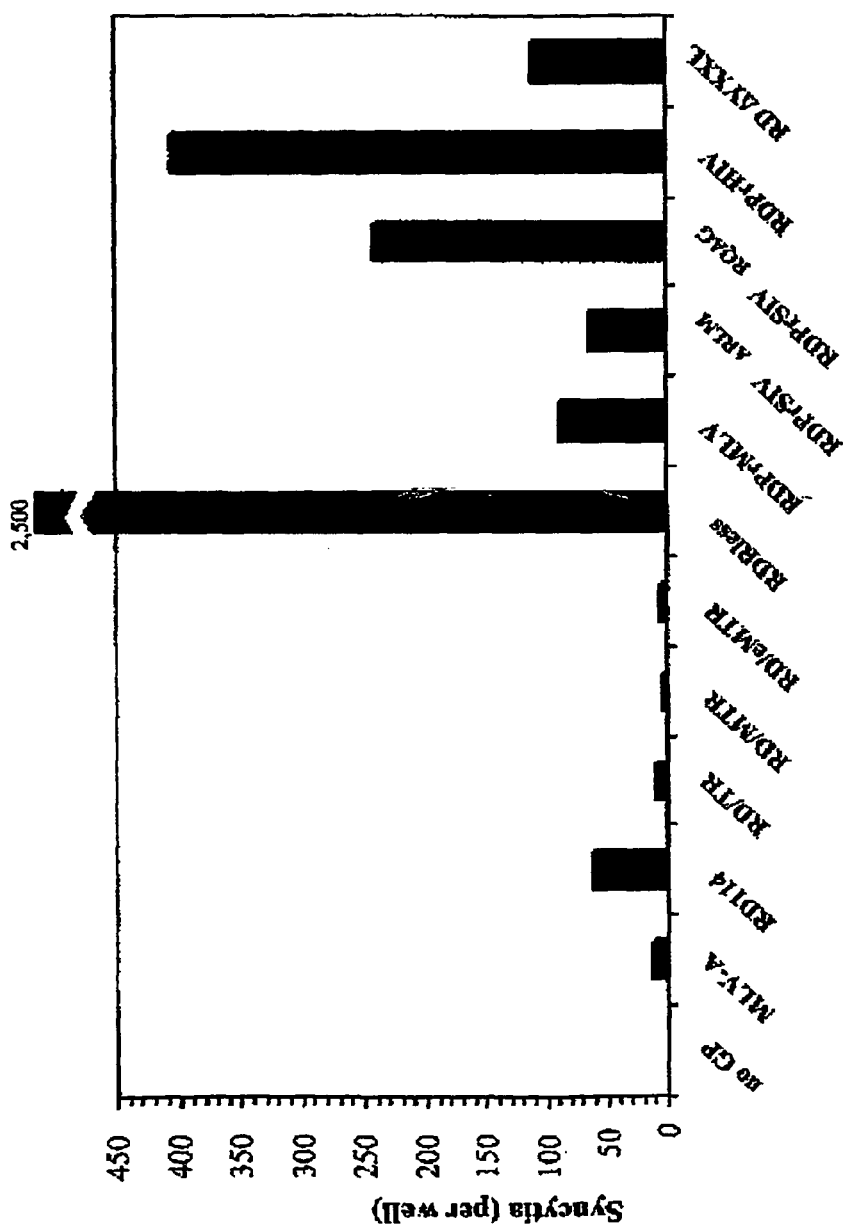
FIG. 8. Results of syncytia assays. Cell-cell fusogenicity of the GP chimeras determined by counting the number of syncytia in transfected cells seeded in 2 $cm^2$ wells. Mock-transfected cells (no GP) were used to determine the background number of syncytia (subtracted here). The data represent the results of three independent experiments.

Cultures of the GP-expressing cells showed formation of syncytia, whose incidence was found to depend on the type of mutation introduced in the cytoplasmic tail (FIG. 8). Compared to wild-type MLV-A GP, expression of the unmodified RD114 GP itself induced significant syncytia formation. This effect appeared to be caused by an inefficient control of GP fusogenicity by the RD114 CT since its substitution with that of MLV-A (mutants RD/TR, RD/MTR and RD/eMTR) significantly reduced the number of syncytia in the transfected cells to the levels detected with wild-type MLV-A GP (FIG. 8). The other RD114 chimeric GPs induced variable levels of syncytia. Maximal cytopathic effects were noticed for the RDPrHIV and RDRless mutants. With the exception of mutant RDPrSIV$_{ARLM}$ which was as fusogenic than the unmodified RD114 GP, the other chimeras (RDΔYXXL, RDPrMLV, and RDPrSIV$_{RQAG}$) induced the formation of syncytia at levels higher than those obtained with the wild-type RD114 GP (FIG. 8). Altered cell-cell fusogenicity was intrinsically linked to modifications of the RD114 GP and was not influenced by interaction with the other viral components present in the transfected cells. Indeed the same levels of syncytia were detected whether the cells expressed, or not, onco-retroviral or lentiviral core proteins (data not shown). Since no variation in GP-expression could be found for the different RD114 GP chimeras, these results established the role played by the RD114 GP cytoplasmic tail in the control of cell-cell fusogenicity. This CT-mediated fusion control was reminiscent of that of other mammalian type C and D retrovirus GPs, such as MLVs and MPMV (2, 30, 33). Sequence modification of the cytoplasmic tail of the RD114 glycoprotein most likely altered its fusion-inhibitory properties, at the instar of MLV-A GP (14, 17, 43). Thus, to minimise the cytopathic effects induced by modifications of the RD114 GP that could be counter-productive for the formation of viral particles, harvests of virions in the supernatants of producer cells were performed shortly, i.e., 36 hrs after transfection.

Example 7

Figure 9:
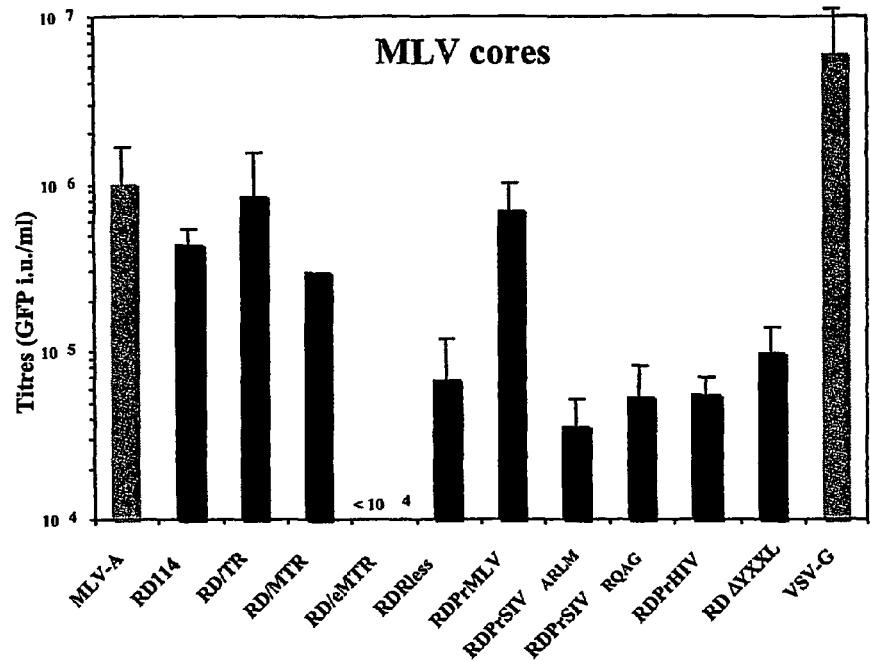
FIG. 9A. Infectivity of vector pseudotypes. Infectivity of MLV vectors pseudotyped with the indicated GP mutants as GFP i.u./ml. The graph shows the mean±SD of four independent experiments. Results obtained with vectors pseudotyped with either the MLV-A GP or with VSV-G are also shown, for comparison.
FIG. 9B. Infectivity of vector pseudotypes. Infectivity of SIV vectors pseudotyped with the indicated GP mutants as GFP i.u./ml. The graph shows the mean±SD of four independent experiments. Results obtained with vectors pseudotyped with either the MLV-A GP or with VSV-G are also shown, for comparison.
Figure 9:
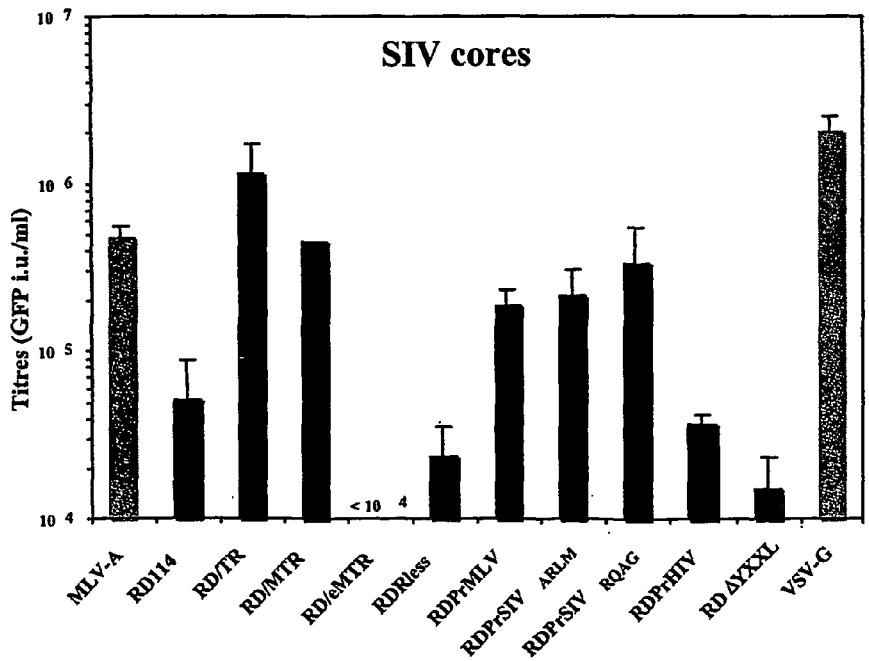

Modifications of the RD114 GP Cytoplasmic Tail Modulate Pseudotyping of Lentiviral or Onco-Retroviral Vectors The capacity of the RD114 GP mutants to pseudotype either SIVmac251- or MLV-based vectors was determined comparatively to wild-type RD114 GP, MLV-A GP and VSV-G. The infectivity of vectors generated in the presence of the different GPs was assessed using TE671 target cells (FIG. 9). Consistent with our previous results, the unmodified RD114 GP could well pseudotype MLV-based vectors (6), but not efficiently lentiviral-based vectors (35). Both SIV and MLV vectors generated with the RDΔYXXL GP mutant had 3 to 4 fold lower titres than vectors pseudotyped with unmodified RD114 GP (FIG. 9). Titres of vectors generated with the hyperfusogenic mutant RDRless were also lower than those generated with wild-type RD114 GP, yet we could not rule out that the particularly strong cytopathic effect exerted by this mutant (FIG. 8) did not preclude the optimal formation of vector particles. Importantly, the RD/TR and RD/MTR chimeric GPs efficiently pseudotyped the SIV-based vectors. In the case of the RD/TR mutant, this resulted in infectious titres higher than $10^6$ i.u./ml; i.e., up to 25 fold higher than those obtained with the wild-type RD114 GPs, and in the same range, if not higher, than infectious titres obtained with SIV vectors pseudotyped with MLV-A GP or VSV-G (FIG. 9B). In contrast, MLV-derived vectors generated with the same chimeric GPs displayed only up to a 2-fold increase of infectivity compared to vectors pseudotyped with wild-type RD114 GP, whose titres were already high (FIG. 9A). Since the cytoplasmic tail was the minimal domain modified in these RD114 GP chimeras that led to increased infectivity of pseudotyped lentiviral vectors, these data therefore suggested that the CT of MLV-A, rather than its TMD, harboured a component that facilitated pseudotype formation with SIV vectors. Investigation of further RD114 GP chimeras (FIG. 7B) established that this component was located in a region that encompassed a putative cleavage site in its cytoplasmic tail.

Viral protease-mediated removal of the C-terminal end from mammalian type C and D retroviruses TM proteins, called R peptide for MLVs, has been shown to be essential to activate their fusion functions (2,30, 33). This carboxy-terminal processing of the TM protei7 s occurs during of after buddirag of the viriofzs. Cleavage of the cytoplasmic tail and subsequent activation of fusogenicity has not been reported so far for the RD114 GP. Our results indicate that processing of the RD114 TM is also likely to be required in order to promote full fusion activity of the glycoprotein upon receptor binding. Indeed, truncation of the RD114 GP by insertion of a premature stop codon (mutant RDRless) resulted in high cell-cell fusogenic activity (FIG. 8), a phenotype similar to that of the R-truncated GP mutants of either type C or D mammalian retroviruses (2,10, 30,33). Moreover sequence alignment of the cytoplasmic tail of RD114 GP with the CTs of several type C and type D mammalian retroviral GPs allowed to predict the position of a 8 amino-acid-long sequence—VHAMVLAQ (SEQ ID NO: 27)—in the cytoplasmic tail of the RD114 GP that most likely formed a retroviral protease cleavage site (FIG. 7A). Interestingly, replacement of this sequence by cleavage sites derived from the MLV CT (mutant RDPrMLV) or from SIV Gag proteins (mutants RDPrSIVARLM and RDPrSIVRQAG) resulted in up to 7 fold increased infectivity of SIV vector pseudotypes (FIG. 9B). Likewise, insertion of a cleavage site derived from HIV-1 Gag proteins (mutant RDPrHIV) selectively increased pseudotype formation with HIV-1-based vectors (data not shown), but not with SIV-derived vectors (FIG. 9B). These results therefore indicated that this 8 amino-acids sequence contains an essential component that modulates pseudotype formation with lentiviral vector particles.

Very different results were obtained when the latter RD114 GP chimeras were used to pseudotype MLV vector particles (FIG. 9A). Although MLV vectors pseudotyped with the RDPrMLV mutant displayed similar or slightly increased infectivity compared to viral pseudotypes formed with the wild-type RD114 GP, RD114 chimeric GPs harbouring lentiviral cleavage sites (RDPrSIV$_{ARLM}$, RDPrSIV$_{RQAG}$ and RDPrHIV) dramatically decreased the infectivity of the MLV pseudotyped vectors, by up to 20 fold (FIG. 9A). Thus the RD114 chimeras behaved differentially when they were associated to either lentiviral or onco-retroviral cores. Therefore these results strongly suggested that particular core/CTs interactions occurred in a virus type-specific manner and could control GP incorporation and/or processing of the cytoplasmic tail.

Example 8

Modifications of the RD114 GP Cytoplasmic Tail Alter Viral Incorporation

We then sought to determine whether modifications of the RD114 glycoprotein might affect its, incorporation on viral particles. These experiments were conducted comparatively to unmodified RD114 GP on a subset of the GP mutants, RDPrMLV, RDPrSIV$_{ARLM}$, RDPrSIV$_{RQAG}$ and RD/TR, which did not induce syncytia formation in a too extensive manner (FIG. 8). Indeed, the high cell-cell fusogenic activity of the other mutants (RDPrHIV and RDRless) compromised the quality of the purified virion preparations by releasing cell debris in the producer cell supernatants (data not shown). Viral particles carrying either SIV or MLV cores were generated with the RD114 GP chimeras and were purified by ultracentrifugation through 20% sucrose cushions. Detection and quantification of both viral core proteins and glycoproteins were performed by immunoblotting of the purified virions using anti-CA or anti-RD114 GP antibodies and allowed to measure the densities of RD114 GP chimeras on the viral particles (FIG. 4). No GP could be detected in the pellets of ultracentrifuged supernatants from producer cells that only expressed the glycoproteins in the absence of viral cores (FIG. 4), thus demonstrating the specificity of the signals obtained with the purified virions. Compared to wild-type RD114 GP, the RDPrSIV$_{ARLM}$ GP mutant was equally well incorporated on SIV core particles, despite the increased infectivity conferred by this GP (FIG. 9B). In contrast, incorporation of the RDPrMLV, RDPrSIV$_{RQAG}$ and RD/TR chimeric GPs on SIV vector particles was increased by 3 to 10 fold (FIG. 4), in agreement with the strongly enhanced titres obtained with these mutant GPs (FIG. 9B). Thus, these results indicated that incorporation of the RD114 GP chimeras on SIV cores particles and infectious titres of the pseudotyped vectors were correlated, although the case of the RDPrSIV$_{ARLM}$ GP mutant ruled out an absolute correlation.

Contrasting results were obtained for incorporation of the same GP chimeras on MLV core particles. Incorporation of the RD/TR GP chimera was weakly increased, by up to 2 fold (FIG. 4), consistent with the slightly enhanced viral titres obtained with this particular mutant (FIG. 9A). However, compared to unmodified RD114 GP, the RDPrMLV, RDPrSIV$_{ARLM}$ and RDPrSIV$_{RQAG}$ GP mutants had similar densities on MLV particles (FIG. 4), despite the strongly reduced titres of the two latter GP chimeras on the pseudotyped MLV vectors (FIG. 9A). Therefore, on pseudotyped MLV cores, no correlation could be demonstrated between GP incorporation and infectivity.

Example 9

Modifications of the RD114 GP Cytoplasmic Tail Alter its Cleavage in a Viral Core-Dependent Manner We then investigated whether the cytoplasmic tail of the RD114 GP chimeras was cleaved in pseudotyped MLV or SIV viral core particles. Transfected cells, producing either of the two types of pseudotyped virons, were radio-labelled with $^{35}$S-methionine and $^{35}$S-cysteine. Lysates of the virion-producer cells or of virions purified on 20% sucrose cushions were incubated with anti-RD114 SU antibodies. After immuno-precipitation of the glycoproteins, samples were reduced and denatured to allow dissociation of the TM proteins for the immuno-precipitated GP complexes and then analyzed by SDS-PAGE (FIG. 5). Lysates of virion-producer cells revealed similar quantities of both SU and TM glycoproteins, as expected. All mutant TM glycoproteins had the same electrophoretic mobility on gels (FIGS. 5A and B), indicating that the majority of the CTs of the different TM species were not cleaved inside the producer cells. These results also confirmed that the modulation of the cell-cell fusogenicity of the mutant RD114 GPs was not dependent on processing of their TM proteins (FIG. 8) but, rather, was intrinsically linked to alteration of the structure or conformation of their cytoplasmic tails.

The different RD114 GP chimeras had similar intensities on the purified MLV viral cores, for both SU and TM subunits (FIG. 5A). This result confirmed that modification of their cytoplasmic tails did not affect their incorporation on oncoretroviral cores (FIG. 4). However, processing of the incorporated TM glycoproteins was detected in a manner dependent on the type of RD114 GP chimera. Indeed, compared to the size of their TM proteins in cell lysates, the TM subunits of the unmodified RD114 GP and of the chimeric RDPrMLV and RD/TR chimeras were approximately 2 kDa shorter (FIG. 5). This observation directly confirmed the genetic evidence for TM processing of the RD114 GP by the viral core protease. In contrast, only unprocessed TMs were detected on MLV cores for the RDPrSIV$_{ARLM}$ and RDPrSIV$_{RQAG}$ GP mutants (FIG. 5A) that harbour lentiviral protease-specific cleavage sites (FIG. 7B). These results were in agreement with the strongly reduced infectivity of MLV vectors pseudotyped with the latter RD114 chimeric GPs (FIG. 9A) and confirmed that cleavage of the cytoplasmic tail of the RD114 GP is required to allow virion infection.

In contrast to MLV cores, variable quantities of both SU and TM glycoproteins were detected on SIV core particles (FIG. 5B) and were in agreement with the results of differential GP incorporation into virions (FIG. 4). In the case of the RDPrSIV$_{RQAG}$ and RD/TR GP mutants whose SUs were readily incorporated on SIV particles, the TM proteins could be observed (FIG. 5B). Efficient processing of the cytoplasmic tails of the latter RD114 GP chimeras could be detected, in agreement with the results of infectivity of the SIV vector pseudotypes (FIG. 9B). The TM proteins of the unmodified RD114 GP and of the RDPrMLV and RDPrSIV$_{ARLM}$ mutant GPs were not easily detected under normal conditions of exposure of the gels, in agreement with the results of incorporation (FIG. 9B). Over-exposure of the gels revealed that the TM proteins of the latter GPs were processed (data not shown). This result explained the low infectious levels obtained with SIV vector particles generated with these latter GPs (FIG. 9B).

Example 10

Modifications of the RD114 GP Cytoplasmic Tail do not Affect GP Localisation in Lipid Rafts Recent reports have shown that lentiviruses may assemble and bud selectively from lipid rafts (18, 25, 26). Therefore one possibility to explain the differential incorporation of the RD114 GP mutants on pseudotyped SIV particles could be the variation of co-localisation of viral core components and glycoproteins at the viral assembly site as a result of modification of the RD114 GP cytoplasmic tail. Thus we investigated whether the RD114 GP might localise to lipid rafts and whether modification of its cytoplasmic tail may alter cellular localisation. Lipid rafts are resistant to nonionic detergents at low temperature and can be physically separated from the bulk of soluble membranes by sucrose gradient centrifugation. Membranes of cells transfected with the different GP mutants were fractionated under these conditions and the GP content of the membrane fractions was analyzed by western-blot analysis (FIG. 6). Wild-type RD114 GP as well as cytoplasmic tail mutants appeared in the detergent-resistant fractions of the lysates of transfected cells, indicating that all GPs were targeted to rafts.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,682,195
U.S. Pat. No. 4,683,202
U.S. Pat. No. 5,466,468
U.S. Pat. No. 5,645,897
U.S. Pat. No. 5,686,279
U.S. Pat. No. 5,705,629
U.S. Pat. No. 5,846,225
U.S. Pat. No. 5,846,233
U.S. Pat. No. 5,925,565
U.S. Pat. No. 5,928,906
U.S. Pat. No. 5,935,819
U.S. Pat. No. 5,994,136
U.S. Pat. No. 6,013,516
U.S. Pat. No. 6,136,597
EP 266,032

SUPERSCRIPT NUMBERED REFERENCES

1. Nègre D, Duisit G, Mangeot P-E, Moullier P, Darlix J-L, Cosset F-L. Lentiviral vectors derived from simian immunodeficiency virus (SIV). In: Trono D, ed. Current Topics in Microbiology and Immunology. Vol. 261; 2002: 53-74
2. Naldini L, Blömer U, Gallay P, Ory D, Mulligan R, Gage F H, Verma I M, Trono D. In vivo gene delivery and stable transduction of nondividing cells by a lentiviral vector. Science. 1996; 272:263-267
3. Blömer U, Naldini L, Kafri T, Trono D, Verma I M, Gage F H. Highly efficient and sustained gene transfer in adult neurons with a lentiviral vector. J Virol. 1997; 71:6641-6649
4. Kafri T, Blömer U, Peterson D A, Gage F H, Verma I M. Sustained expression of genes delivered directly into liver and muscle by lentiviral vectors. Nat Genet. 1997; 17:314-317
5. Naldini L, Blömer U, Gage F H, Trono D, Verma I M. Efficient transfer, integration, and sustained long-term expression of the transgene in adult rat brains injected with a lentiviral vector. Proc Natl Acad Sci USA. 1996; 93:11382-11388
6. Park F. Efficient lentiviral transduction of liver requires cell cycling in vivo. Nat Genet. 2000; 24:49-52
7. Takahashi M, Miyoshi H, Verma I M, Gage F H. Rescue from photoreceptor degeneration in the rd mouse by human immunodeficiency virus vector-mediated gene transfer. J Virol. 1999; 73:7812-7816
8. Christodoulopoulos I, Cannon P. Sequences in the cytoplasmic tail of the gibbon ape leukemia virus envelope protein that prevent its incorporation into lentivirus vectors. J Virol. 2001; 75:4129-4138
9. Desmaris N, Bosch A, Salaun C, Petit C, Prevost M C, Tordo N, Perrin P, Schwartz O, deRocquigny H, Heard J M. Production and neurotropism of lentivirus vectors pseudotyped with lyssavirus envelope glycoproteins. Mol Ther. 2001; 4:149-156
10. Kobinger G P, Weiner D J, Yu Q C, Wilson J M. Filovirus-pseudotyped lentiviral vector can efficiently and stably transduce airway epithelia in vivo. Nat Biotechnol. 2001; 19:225-230
11. Lewis B C, Chinnasamy N, Morgan R A, Varmus H E. Development of an Avian Leukosis-Sarcoma Virus Subgroup A Pseudotyped Lentiviral Vector. J Virol. 2001; 75:9339-9344
12. Mochizuki H, Schwartz J P, Tanaka K, Brady R O, Reiser J. High-Titer Human Immunodeficiency Virus Type 1-Based Vector Systems for Gene Delivery into Nondividing Cells. J. Virol. 1998; 72:8873-8883
13. Salmon P, Nègre D, Trono D, Cosset F-L. A chimeric GALV-derived envelope glycoprotein harboring the cytoplasmic tail of MLV envelope efficiently pseudotypes HIV-1 vectors. J Gen Med. 2000; 2 (sup):23
14. Sandrin V, Boson B, Cosset F-L. Insertion of lentiviral protease substrates in the cytoplasmic tail of the feline endogenous virus RD114 glycoprotein enhances viral incorporation and infectivity of pseudotyped lentiviral vectors. in preparation. 2001
15. Stitz J, Buchholz C, Engelstadter M, Uckert W, Bloemer U, Schmitt I, Cichutek K. Lentiviral vectors pseudotyped with envelope glycoproteins derived from gibbon ape leukemia virus and murine leukemia virus 10A1. Virology. 2000; 273:16-20
16. Gatlin J, Melkus M W, Padgett A, Kelly P F, Garcia J V. Engraftment of NOD/SCID Mice with Human CD34+ Cells Transduced by Concentrated Oncoretroviral Vector Particles Pseudotyped with the Feline Endogenous Retrovirus (RD114) Envelope Protein. J. Virol. 2001; 75:9995-9999
17. Goerner M, Horn P A, Peterson L, Kurre P, Storb R, Rasko J E, Kiem H P. Sustained multilineage gene persistence and expression in dogs transplanted with CD34(+) marrow cells transduced by RD114-pseudotype oncoretrovirus vectors. Blood. 2001; 98:2065-2070
18. Kelly P, Vandergriff J, Nathwani A, Nienhuis A, Vanin E. Highly efficient gene transfer into cord blood nonobese diabetic/severe combined immunodeficiency repopulating cells by oncoretroviral vector particles pseudotyped with the feline endogenous retrovirus (RD114) envelope protein. Blood. 2000; 96:1206-1214
19. Marandin A, Dubart A, Pflumio F, Cosset F-L, Cordette V, Chapel-Fernandes S, Coulombel L, Vainchenker W, Louache F. Retroviral-mediated gene transfer into human CD34+/38-primitive cells capable of reconstituting long-term cultures in vitro and in nonobese diabetic-severe combined immunodeficiency mice in vivo. Human Gene Ther. 1998; 9:1497-1511

20. Movassagh M, Desmyter C, Baillou C, Chapel-Fernandes S, Guigon M, Klatzmann D, Lemoine F M. High-level gene transfer to cord blood progenitors using gibbon ape leukemia virus pseudotyped retroviral vectors and an improved clinically applicable protocol. Hum Gene Ther. 1998; 9:225-234

21. Porter C D, Collins M K L, Tailor C S, Parker M H, Cosset F-L, Weiss R A, Takeuchi Y. Comparison of efficiency of infection of human gene therapy target cells via four different retroviral receptors. Human Gene Therapy. 1996; 7:913-919

22. Peng K W, Pham L, Ye H, Zufferey R, Trono D, Cosset F-L, Russell S J. Organ distribution of gene expression after intravenous infusion of targeted and untargeted lentiviral vectors. Gene Therapy. 2001; 8:1456-1463

23. Seganti L, Superti F, Girmenia C, Melucci L, Orsi N. Study of receptors for vesicular stomatitis virus in vertebrate and invertebrate cells. Microbiologica. 1986; 9:259-267

24. DePolo N J, Reed J D, Sheridan P L, Townsend K, Sauter S L, Jolly D J, Dubensky T W. VSV-G pseudotyped lentiviral vector particles produced in human cells are inactivated by human serum. Mol Ther. 2000; 2:218-222

25. Nègre D, Mangeot P, Duisit G, Blanchard S, Vidalain P, Leissner P, Winter A, Rabourdin-Combe C, Mehtali M, Moullier P, Darlix J-L, Cosset F-L. Characterization of novel safe lentiviral vectors derived from simian immunodeficiency virus (SIVmac251) that efficiently transduce mature human dendritic cells. Gene Ther. 2000; 7:1613-1623

26. Salmon P, Kindler V, Ducrey O, Chapuis B, Zubler R H, Trono D. High-level transgene expression in human hematopoietic progenitors and differentiated blood lineages after transduction with improved lentiviral vectors. Blood. 2000; 96:3392-3398

27. Salmon P, Arrighi J F, Piguet V, Chapuis B, Zubler R H, Trono D, Kindler V. Transduction of CD34+ cells with lentiviral vectors enables the production of large quantities of transgene-expressing immature and mature dendritic cells. J Gene Med. 2001; 3:311-320

28. Thiebot H, Louache F, Vaslin B, Revel T d, Neildez O, Larghero J, Vainchenker W, Dormont D, Grand R L. Early and persistent bone marrow hematopoiesis defect in simian/human immunodeficiency virus-infected macaques despite efficient reduction of viremia by highly active antiretroviral therapy during primary infection. J Virol. 2001; 75:11594-11602

29. Maurice M, Verhoeyen E, Salmon P, Trono D, Russell S J, Cosset F-L. Efficient gene transfer into human primary blood lymphocytes by surface-engineered lentiviral vectors that display a T cell-activating polypeptide. Blood. 2002; 99:in press 30. Mangeot P-E, Nègre D, Dubois B, Winter A J, Leissner P, Methali M, Kaiserlian D, Cosset F-L, Darlix J-L. Development of minimal lentiviral vectors derived from simian immunodeficiency virus (SIVmac251) and their use for the gene transfer in human dendritic cells. J. Virol. 2000; 74:8307-8315

31. Yee J K, Friedmann T, Burns J C. Generation of high-titer pseudotyped retroviral vectors with very broad host range. Methods Cell Biol. 1994; 43:99-112

32. Hatziioannou T, Valsesia-Wittmann S. Russell S, Cosset F-L. Incorporation of fowl plague virus hemagglutinin into murine leukemia virus particles and analysis of the infectivity of the pseudotyped retroviruses. J Virol. 1998; 72:5313-5317

33. Collins M K L, Weiss R A, Takeuchi Y, Cosset F-L. Expression systems. PCT/GB96/02061. WO 97/08330. 1996

34. Cosset F-L, Takeuchi Y, Battini J, Weiss R, Collins M. High titer packaging cells producing recombinant retroviruses resistant to human serum. J. Virol. 1995; 69:7430-7436

35. Ott D, Friedrich R, Rein A. Sequence analysis of amphotropic and 10A1 murine leukemia virus: close relationship to mink cell focus forming viruses. J Virol. 1990; 64:757-766

36. Takeuchi Y, Cosset F L, Lachmann P J, Okada H, Weiss R A, Collins M K L. Type C retrovirus inactivation by human complement is determined by both the viral genome and producer cell. J. Virol. 1994; 68:8001-8007

37. Matheux F, Lauret E, Rousseau V, Larghero J, Boson B, Vaslin B, Cheret A, DeMaeyer E, Dormont D, LeGrand R. Simian immunodeficiency virus resistance of macaques infused with interferon beta-engineered lymphocytes. J Gen Virol. 2000; 81:2741-2750

38. Hatziioannou T, Delahaye E, Martin F, Russell S J, Cosset F-L. Retroviral display of functional binding domains fused to the amino-terminus of influenza haemagglutinin. Human Gene Therapy. 1999; 10:1533-1544

39. Freed E O. HIV-1 gag proteins: diverse functions in the virus life cycle. Virology. 1998; 251:1-15

40. Bosch V, Kramer B, Pfeiffer T, Starck L, Steinhauer D A. inhibition of release of lentivirus particles with incorporated human influenza virus haemagglutinin by binding to sialic acid-containing cellular receptors. J Gen Virol. 2001; 82:2485-2494

41. Wagner R, Wolff T, Herwig A, Pleschka S, Klenk H D. Interdependence of hemagglutinin glycosylation and neuraminidase as regulators of influenza virus growth: a study by reverse genetics. J Virol. 2000; 74:6316-6323

42. Carstanjen D, Dutt P, Moritz T. Heparin inhibits retrovirus binding to fibronectin as well as retrovirus gene transfer on fibronectin fragments. J Virol. 2001; 75:6218-6222

43. Moritz T, Dutt P, Xiao X, Carstanjen D, Vik T, Hanenberg H, Williams D A. Fibronectin improves transduction of reconstituting hematopoietic stem cells by retroviral vectors: evidence of direct viral binding to chymotryptic carboxy-terminal fragments. Blood. 1996; 88:855-862

44. Relander T, Brun A, Hawley R G, Karlsson S, Richter J. Retroviral transduction of human CD34+ cells on fibronectin fragment CH-296 is inhibited by high concentrations of vector containing medium. J Gene Med. 2001; 3:207-218

45. Haas D L, Case S S, Crooks G M, Kohn D B. Critical factors influencing stable transduction of human CD34(+) cells with HIV-1-derived lentiviral vectors. Mol Ther. 2000; 2:71-80

46. Dardalhon V, Herpers B, Noraz N, Pflumio F, Guetard D, Leveau C, Dubart-kupperschmitt A, Charneau P, Taylor N. Lentivirus-mediated gene transfer in primary T cells is enhanced by a central DNA flap. Gene therapy. 2001; 8:190-198

47. Slingsby J H, Baban D, Sutton J, Esapa M, Price T, Kingsman S M, Kingsman A J, Slade A. Analysis of 4070A envelope levels in retroviral preparations and effect on target cell transduction efficiency. Hum Gene Ther. 2000; 11:1439-1451

48. Ott D E. Cellular proteins in HIV virions. Rev Med Virol. 1997; 7:167-180

49. Swanstrom R, Wills J W. Synthesis, assembly, and processing of viral proteins. In: Coffin J M, Hughes S H, Varmus H E, eds. Retroviruses. New York, USA: Cold Spring Harbor Laboratory Press; 1997: 263-334
50. Takeuchi Y, Simpson G, Vile R, Weiss R, Collins M. Retroviral pseudotypes produced by rescue of moloney murine leukemia virus vector by C-type, but not D-type, retroviruses. Virology. 1992a; 186:792-794
51. Pickl W F, Pimentel-Muinos F X, Seed B. Lipid rafts and pseudotyping. J Virol. 2001; 75:7175-7183
52. Cosson P. Direct interaction between the envelope and matrix proteins of HIV-1. The Embo J. 1996; 15:5783-5788
53. Murakami T, Freed E O. Genetic evidence for an interaction between human immunodeficiency virus type 1 matrix and alpha-helix 2 of the gp41 cytoplasmic tail. J Virol. 2000; 74:3548-3554
54. Vincent M J, Melsen L R, Martin A S, Compans R W. Intracellular interaction of simian immunodeficiency virus Gag and Env proteins. J Virol. 1999; 73:8138-8144
55. Wyma D J, Kotov A, Aiken C. Evidence for a stable interaction of gp41 with Pr55(Gag) in immature human immunodeficiency virus type 1 particles. J Virol. 2000; 74:9381-9387
56. Brody B A, Rhee S S, Hunter E. Postassembly cleavage of a retroviral glycoprotein cytoplasmic domain removes a necessary incorporation signal and activates fusion activity. J Virol. 1994; 68:4620-4627
57. Ragheb J A, Anderson W F. pH-independent murine leukemia virus ecotropic envelope-mediated cell fusion: Implications for the role of the R peptide and p12E TM in viral entry. J Virol. 1994; 68:3220-3231
58. Rein A, Mirro J, Haynes J G, Ernst S M, Nagashima K. Function of the cytoplasmic domain of a retroviral transmembrane protein: p15E-p2E cleavage activates the membrane fusion capability of the murine leukemia virus env protein. J Virol. 1994; 68:1773-1781
59. Galili U, Shohet S B, Kobrin E, Stults C L, Macher B A. Man, apes, and Old World monkeys differ from other mammals in the expression of alpha-galactosyl epitopes on nucleated cells. J Biol Chem. 1988; 263:17755-17762
60. Rother R P, Fodor W L, Springhorn J P, Birks C W, Setter E, Sandrin M S, Squinto S P, Rollins S A. A novel mechanism of retrovirus inactivation in human serum mediated by anti-alpha-galactosyl natural antibody. J Exp Med. 1995; 182:1345-1355
61. Takeuchi Y, Porter C, Strahan K, Preece A, Gustafsson K, Cosset P-L, Weiss R, Collins M. Sensitisation of cells and retroviruses to human serum by alpha(1-3) galactosyltransferase. Nature. 1996; 379:85-88
62. Takeuchi Y, Liong S H, Bieniasz P D, Jager U, Porter C D, Friedman T, McClure M O, Weiss R A. Sensitization of rhabdo-, lenti-, and spumaviruses to human serum by galactosyl(alpha1-3)galactosylation. J Virol. 1997; 71:6174-6178
63. DePolo N J, Harkleroad C E, Bodner M, Watt A T, Anderson C G, Greengard J S, Murthy K K, Jr T W D, Jolly D J. The resistance of retroviral vectors produced from human cells to serum inactivation in vivo and in vitro is primate species dependent. J Virol. 1999; 73:6708-6714
64. Montefiori D C, Cornell R J, Zhou J Y, Zhou J T, Hirsch V M, Johnson P R. Complement control proteins, CD46, CD55, and CD59, as common surface constituents of human and simian immunodeficiency viruses and possible targets for vaccine protection. Virology. 1994; 205:82-92
65. Lavillette D, Russell S J, Cosset F-L. Retargeting gene delivery by surface-engineered retroviral vector particles. Current Opinion in Biotechnology. 2001; 12:461-466
66. Russell S J, Cosset F-L. Modifying the Host Range Properties of Retroviral Vectors. Journal of Gene Medicine. 1999; 1:300-311
67. Donahue R E, Sorrentino B P, Hawley R G, An D S, Chen I S, Wersto R P. Fibronectin fragment CH-296 inhibits apoptosis and enhances ex vivo gene transfer by murine retrovirus and human lentivirus vectors independent of viral tropism in nonhuman primate CD34+ cells. Mol Ther. 2001; 3:359-367
68. Pizzato M, Marlow S A, Blair E D, Takeuchi Y. Initial binding of murine leukemia virus particles to cells does not require specific Env-receptor interaction. J Virol. 1999; 73:8599-8611
69. Barnett A L, Cunningham J M. Receptor binding transforms the surface subunit of the mammalian C-type retrovirus envelope protein from an inhibitor to an activator of fusion. J Virol. 2001; 75:9096-9105
70. Lavillette D, Ruggieri A, Boson B, Maurice M, Cosset F-L. Structural inter-relations between subdomains of the SU that regulate receptor-mediated transition between the fusion-inhibited and fusion-active conformations of the MLV glycoprotein. submitted. 2002
71. Jinno-Oue A, Oue M, Ruscetti S K. A unique heparin-binding domain in the envelope protein of the neuropathogenic PVC-211 murine leukemia virus may contribute to its brain capillary endothelial cell tropism. J Virol. 2001; 75:12439-12445
72. Klimstra W B, Heidner H W, Johnston R E. The furin protease cleavage recognition sequence of Sindbis virus PE2 can mediate virion attachment to cell surface heparan sulfate. J Virol. 1999; 73:6299-6306
73. Uckert W, Willimsky G, Pedersen F S, Blankenstein T, Pedersen L. RNA levels of human retrovirus receptors Pit1 and Pit2 do not correlate with infectibility by three retroviral vector pseudotypes. Hum Gene Ther. 1998; 9:2619-2627
74. Lavillette D, Boson B, Russell S, Cosset F-L. Membrane fusion by murine leukemia viruses is activated in cis or in trans by interactions of the receptor-binding domain with a conserved disulfide loop at the carboxy-terminus of the surface glycoproteins. J of Virol. 2001; 75:3685-3695
75. Rodrigues P, Heard J M. Modulation of Phosphate Uptake and Amphotropic Murine Leukemia Virus Entry by Post-translational Modifications of PIT-2. J. Virol. 1999: 3789-3799

NUMBERED REFERENCES IN PARENTHESES

1. Berlioz-Torrent, C., B. L. Shacklett, L. Erdtmann, L. Delamarre, I. Bouchaert, P. Sonigo, M. C. Dokhelar, and R. Benarous 1999. Interactions of the cytoplasmic domains of human and simian retroviral transmembrane proteins with components of the clathrin adaptor complexes modulate intracellular and cell surface expression of envelope glycoproteins J Virol. 73:1350-1361.
2. Brody, B. A., S. S. Rhee, and E. Hunter 1994. Postassembly cleavage of a retroviral glycoprotein cytoplasmic domain removes a necessary incorporation signal and activates fusion activity J Virol. 68:4620-4627.
3. Brody, B. A., S. S. Rhee, M. A. Sommerfelt, and E. Hunter 1992. A viral protease-mediated cleavage of the transmembrane glycoprotein of Mason-Pfizer monkey virus can be suppressed by mutations within the matrix protein Proc Natl Acad Sci USA. 89:3443-7.

4. Christodoulopoulos, I., and P. Cannon 2001. Sequences in the cytoplasmic tail of the gibbon ape leukemia virus envelope protein that prevent its incorporation into lentivirus vectors J Virol. 75:4129-38.
5. Collawn, J. F., A. Lai, D. Domingo, M. Fitch, S. Hatton, and I. S. Trowbridge 1993. YTRF is the conserved internalization signal of the transferrin receptor, and a second YTRF signal at position 31-34 enhances endocytosis J Biol Chem. 268:21686-21692.
6. Cosset, F.-L., Y. Takeuchi, J. Battini, R. Weiss, and M. Collins 1995. High titer packaging cells producing recombinant retroviruses resistant to human serum J. Virol. 69:7430-7436.
7. Cosson, P. 1996. Direct interaction between the envelope and matrix proteins of HIV-1 The Embo J. 15:5783-5788.
8. Delamarre, L., C. Pique, A. R. Rosenberg, V. Blot, M. P. Grange, I. L. Blanc, and M. C. Dokhelar 1999. The Y-S-L-I tyrosine-based motif in the cytoplasmic domain of the human T-cell leukemia virus type 1 envelope is essential for cell-to-cell transmission. J Virol. 73:9659-9663.
9. Denesvre, C., C. Carrington, A. Corbin, Y. Takeuchi, F.-L. Cosset, T. Schulz, M. Sitbon, and P. Sonigo 1996. TM domain swapping of murine leukemia virus and human T-cell leukemia virus envelopes confers different infectious abilities despite similar incorporation into virions J. Virol. 70:4380-4386.
10. Fielding, A., S. Chapel-Fernandes, M. Chadwick, F. Bullough, F.-L. Cosset, and S. Russell 2000. A hyperfusogenic Gibbon ape leukemia virus envelope glycoprotein: targeting of a cytotoxic gene by ligand display Human Gene Therapy. 11:817-826.
11. Freed, E. O. 1998. HIV-1 gag proteins: diverse functions in the virus life cycle Virology. 251:1-15.
12. Freed, E. O., and M. A. Martin 1995. Virion incorporation of envelope glycoproteins with long but not short cytoplasmic tails is blocked by specific, single amino acid substitutions in the human immunodeficiency virus type 1 matrix J Virol. 69:1984-1989.
13. Grange, M., V. Blot, L. Delamarre, I. Bouchaert, A. Rocca, A. Dautry-Varsat, and M. Dokhelar 2000. Identification of two intracellular mechanisms leading to reduced expression of oncoretrovirus envelope glycoproteins at the cell surface J Virol. 74:11734-11743.
14. Januszeski, M. M., P. M. Cannon, D. Chen, Y. Rozenberg, and W. F. Anderson 1997. Functional analysis of the cytoplasmic tail of Moloney murine leukemia virus envelope protein J Virol. 71:3613-9.
15. Kiernan, R. E., and E. O. F. EO 1998. Cleavage of the murine leukemia virus transmembrane env protein by human immunodeficiency virus type 1 protease: transdominant inhibition by matrix mutations J Virol. 72:9621-7.
16. Kim, F. J., I. Seiliez, C. Denesvre, D. Lavillette, F.-L. Cosset, and M. Sitbon 2000. Definition of an amino-terminal domain of the human T-cell leukemia virus type 1 envelope surface unit which extends the fusogenic range of an ecotropic murine leukemia virus Journal of Biological Chemistry. 275:23417-20.
17. Li, M., C. Yang, and R. W. Compans 2001. Mutations in the cytoplasmic tail of murine leukemia virus envelope protein suppress fusion inhibition by R peptide J Virol. 75:2337-44.
18. Lindwasser, O. W., and M. D. Resh 2001. Multimerization of human immunodeficiency virus type 1 Gag promotes its localization to barges, raft-like membrane microdomains J Virol. 75:7913-24.
19. Lodge, R., L. Delamarre, J. P. Lalonde, J. Alvarado, D. A. Sanders, M. C. Dokhelar, E. A. Cohen, and G. Lemay 1997. Two distinct oncornaviruses harbor an intracytoplasmic tyrosine-based basolateral targeting signal in their viral envelope glycoprotein J Virol. 71:5696-702.
20. Mangeot, P.-E., D. Nègre, B. Dubois, A. J. Winter, P. Leissner, M. Methali, D. Kaiserlian, F.-L. Cosset, and J.-L. Darlix 2000. Development of minimal lentiviral vectors derived from simian immunodeficiency virus (SIV-mac251) and their use for the gene transfer in human dendritic cells J Virol. 74:8307-8315.
21. Murakami, T., and E. O. Freed 2000. Genetic evidence for an interaction between human immunodeficiency virus type 1 matrix and alpha-helix 2 of the gp41 cytoplasmic tail J Virol. 74:3548-54.
22. Naldini, L., U. Blömer, P. Gallay, D. Ory, R. Mulligan, F. H. Gage, I. M. Verma, and D. Trono 1996. In vivo gene delivery and stable transduction of nondividing cells by a lentiviral vector Science. 272:263-267.
23. Nègre, D., G. Duisit, P.-E. Mangeot, P. Moullier, J.-L. Darlix, and F.-L. Cosset 2002. Lentiviral vectors derived from simian immunodeficiency virus (SIV), p. 53-74. In D. Trono (ed.), Current Topics in Microbiology and Immunology, vol. 261.
24. Nègre, D., P. Mangeot, G. Duisit, S. Blanchard, P. Vidalain, P. Leissner, A. Winter, C. Rabourdin-Combe, M. Mehtali, P. Moullier, J.-L. Darlix, and F.-L. Cosset 2000. Characterization of novel safe lentiviral vectors derived from simian immunodeficiency virus (SIVmac251) that efficiently transduce mature human dendritic cells Gene Ther. 7:1613-1623.
25. Nguyen, D. H., and J. E. Hildreth 2000. Evidence for budding of human immunodeficiency virus type 1 selectively from glycolipid-enriched membrane lipid rafts J Virol. 74:3264-72.
26. Ono, A., and E. O. Freed 2001. Plasma membrane rafts play a critical role in HIV-1 assembly and release PNAS. 98:13925-13930.
27. Ott, D., R. Friedrich, and A. Rein 1990. Sequence analysis of amphotropic and 10A1 murine leukemia virus: close relationship to mink cell focus forming viruses. J Virol. 64:757-766.
28. Overbaugh, J., A. D. Miller, and M. V. Eiden 2001. Receptors and Entry Cofactors for Retroviruses Include Single and Multiple Transmembrane-Spanning Proteins as well as Newly Described Glycophosphatidylinositol-Anchored and Secreted Proteins Microbiol Mol Biol Rev. 65:371-89.
29. Pickl, W. F., F. X. Pimentel-Muinos, and B. Seed 2001. Lipid rafts and pseudotyping J Virol. 75:7175-83.
30. Ragheb, J. A., and W. F. Anderson 1994. pH-independent murine leukemia virus ecotropic envelope-mediated cell fusion: Implications for the role of the R peptide and p12E TM in viral entry. J Virol. 68:3220-3231.
31. Rasko, J. E., J. L. Battini, R. J. Gottschalk, I. Mazo, and A. D. Miller 1999. The RD114/simian type D retrovirus receptor is a neutral amino acid transporter Proc Natl Acad Sci USA. 96:2129-2134.
32. Reeves, R. H., and S. J. O'Brien 1984. Molecular genetic characterisation of the RD114 gene family of endogenous feline retroviral sequences J. Virol. 52:164-171.
33. Rein, A., J. Mirro, J. G. Haynes, S. M. Ernst, and K. Nagashima 1994. Function of the cytoplasmic domain of a retroviral transmembrane protein: p15E-p2E cleavage activates the membrane fusion capability of the murine leukemia virus env protein J Virol. 68:1773-1781.
34. Salmon, P., D. Nègre, D. Trono, and F.-L. Cosset 2000. A chimeric GALV-derived envelope glycoprotein harboring the cytoplasmic tail of MLV envelope efficiently pseudotypes HIV-1 vectors J Gen Med. 2 (sup):23.
35. Sandrin, V., B. Boson, P. Salmon, W. Gay, D. Nègre, R. L. Grand, D. Trono, and F.-L. Cosset 2002. Lentiviral vectors pseudotyped with a modified RD114 envelope glycoprotein show increased stability in sera and augmented transduction of primary lymphocytes and CD34+ cells derived from human and non-human primates Blood. in press.
36. Stitz, J., C. Buchholz, M. Engelstadter, W. Uckert, U. Bloemer, I. Schmitt, and K Cichutek 2000. Lentiviral vectors pseudotyped with envelope glycoproteins derived from gibbon ape leukemia virus and murine leukemia virus 10A1 Virology. 273:16-20.
37. Swanstrom, R., and J. W. Wills 1997. Synthesis, assembly, and processing of viral proteins, p. 263-334. In J. M. Coffin, S. H. Hughes, and H. E. Varmus (eds), Retroviruses. Cold Spring Harbor Laboratory Press, New York, USA.
38. Tailor, C. S., A. Nouri, Y. Zhao, Y. Takeuchi, and D. Kabat 1999. A sodium-dependent neutral-amino-acid transporter mediates infections of feline and baboon endogenous retroviruses and simian type D retroviruses J Virol. 73:4470-4474.
39. Takeuchi, Y., F. L. Cosset, P. J. Lachmann, H. Okada, R. A. Weiss, and M. K. L. Collins 1994. Type C retrovirus inactivation by human complement is determined by both the viral genome and producer cell J. Virol. 68:8001-8007.
40. Takeuchi, Y., R. G. Vile, G. Simpson, B. O'Hara, M. K. L. Collins, and R. A. Weiss 1992b. Feline leukemia virus subgroup B uses the same cell surface receptor as gibbon ape leukemia virus J Virol. 66:1219-1222.
41. Vincent, M. J., L. R. Melsen, A. S. Martin, and R. W. Compans 1999. Intracellular interaction of simian immunodeficiency virus Gag and Env proteins J Virol. 73:8138-44.
42. Wyma, D. J., A. Kotov, and C. Aiken 2000. Evidence for a stable interaction of gp41 with Pr55(Gag) in immature human immunodeficiency virus type 1 particles J Virol. 74:9381-7.
43. Yang, C., and R. W. Compans 1997. Analysis of the murine leukemia virus R peptide: delineation of the molecular determinants which are important for its fusion inhibition activity J Virol. 71:8490-8496.
Yee, J. K., T. Friedmann, and J. C. Burns 1994. Generation of high-titer pseudotyped retroviral vectors with very broad host range Methods Cell Biol. 43:99-112.

ADDITIONAL REFERENCES

Akkina, Walton, Chen, Li, Planelles, Chen, "High-efficiency gene transfer into CD34+ cells with a human immunodeficiency virus type 1-based retroviral vector pseudotyped with vesicular stomatitis virus envelope glycoprotein G," *J. Virol.*, 70:2581-2585, 1996.
Almendro et al., "Cloning of the human platelet endothelial cell adhesion molecule-1 promoter and its tissue-specific expression. Structural and functional characterization," *J. Immunol.*, 157(12):5411-5421, 1996.
An, Wersto, Agricola, Metzger, Lu, Amado, Chen, Donahue, "Marking and gene expression by a lentivirus vector in transplanted human and nonhuman primate CD34(+) cells," *J. Virol.*, 74:1286-1295, 2000.
Angel, Bauman, Stein, Dellus, Rahmsdorf, and Herrlich, "12-0-tetradecanoyl-phorbol-13-acetate Induction of the Human Collagenase Gene is Mediated by an Inducible Enhancer Element Located in the 5'Flanking Region," *Mol. Cell. Biol.*, 7:2256, 1987a.
Angel, Imagawa, Chiu, Stein, Imbra, Rahmsdorf, Jonat, Herrlich, and Karin, "Phorbol Ester-Inducible Genes Contain a Common cis Element Recognized by a TPA-Modulated Trans-acting Factor," *Cell*, 49:729, 1987b
Arrighi, Hauser, Chapuis, Zubler, Kindler, "Long-term culture of human CD34(+) progenitors with FLT3-ligand, thrombopoietin, and stem cell factor induces extensive amplification of a CD34(-)CD14(-) and CD34(-)CD14 (+) dendritic cell precursor," *Blood*, 93:2244-2252, 1999.
Atchison and Perry, "Tandem Kappa Immunoglobulin Promoters are Equally Active in the Presence of the Kappa Enhancer: Implications for Model of Enhancer Function," *Cell*, 46:253, 1986.
Atchison and Perry, "The Role of the Kappa Enhancer and its Binding Factor NF-kappa B in the Developmental Regulation of Kappa Gene Transcription," *Cell*, 48:121, 1987.
Banerji et al., "Expression of a Beta-Globin Gene is Enhanced by Remote SV40 DNA Sequences," *Cell*, 27:299, 1981.
Banerji, Olson, and Schaffner, "A lymphocyte-specific cellular enhancer is located downstream of the joining region in immunoglobulin heavy-chain genes," *Cell*, 35:729, 1983.
Berkhout, Silverman, and Jeang, "Tat Trans-activates the Human Immunodeficiency Virus Through a Nascent RNA Target," *Cell*, 59:273, 1989.
Bhatia, Bonnet, Kapp, Wang, Murdoch, Dick, "Quantitative analysis reveals expansion of human hematopoietic repopulating cells after short-term ex vivo culture," *J. Exp. Med.*, 186:619-624, 1997.
Blanar, Baldwin, Flavell, and Sharp, "A gamma-interferon-induced factor that binds the interferon response sequence of the MHC class I gene, H-2Kb," *EMBO J.*, 8:1139, 1989.
Blomer, Naldini, Kafri, Trono, Verma, Gage, "Highly efficient and sustained gene transfer in adult neurons with a lentivirus vector," *J. Virol.*, 71:6641-6649, 1997.
Bodine and Ley, "An enhancer element lies 3' to the human a gamma globin gene," *EMBO J.*, 6:2997, 1987.
Boshart, Weber, Jahn, Dorsch-Hasler, Fleckenstein, and Schaffner, "A very strong enhancer is located upstream of an immediate early gene of human cytomegalovirus," *Cell*, 41:521, 1985.
Bosze, Thiesen, and Charnay, "A transcriptional enhancer with specificity for erythroid cells is located in the long terminal repeat of the friend murine leukemia virus," *EMBO J.*, 5:1615, 1986.
Braddock, Chambers, Wilson, Esnouf, Adams, Kingsman, and Kingsman, "HIV-I Tat activates presynthesized RNA in the nucleus," *Cell*, 58:269, 1989.
Bray, Prasad, Dubay, Hunter, Jeang, Rekosh, Hammarskjold, "A small element from the Mason-Pfizer monkey virus genome makes human immunodeficiency virus type 1 expression and replication Rev-independent," *Proc. Natl. Acad. Sci.* 91:1256-60, 1994.
Brown, Tiley, Cullen, "Efficient polyadenylation within the human immunodeficiency virus type 1 long terminal repeat requires flanking U3-specific sequences," *J. Virol.*, 65:3340-3343, 1991.
Bulla and Siddiqui, "The hepatitis B virus enhancer modulates transcription of the hepatitis B virus surface-antigen gene from an internal location," *J. Virol.*, 62:1437, 1986.
Campbell and Villarreal, "Functional analysis of the individual enhancer core sequences of polyoma virus: cell-specific uncoupling of DNA replication from transcription," *Mol. Cell. Biol.*, 8:1993, 1988.
Campere and Tilghman, "Postnatal repression of the alpha-fetoprotein gene is enhancer independent," *Genes and Dev.*, 3:537, 1989.

Campo, Spandidos, Lang, Wilkie, "Transcriptional control signals in the genome of bovine papilloma virus type 1," Nature, 303:77, 1983.

Carbonelli et al. "A plasmid vector for isolation of strong promoters in E. coli," FEMS Microbiol Lett. 177(1):75-82, 1999.

Case, Price, Jordan, Yu, Wang, Bauer, Haas, Xu, Stripecke, Naldini, Kohn, Crooks, "Stable transduction of quiescent CD34(+)CD38(-) human hematopoietic cells by HIV-1 based lentiviral vectors," Proc. Natl. Acad. Sci. USA, 96:2988-2993, 1999.

Celander and Haseltine, "Glucocorticoid Regulation of Murine Leukemia Virus Transcription Elements is Specified by Determinants Within the Viral Enhancer Region," J. Virology, 61:269, 1987.

Celander, Hsu, and Haseltine, "Regulatory Elements Within the Murine Leukemia Virus Enhancer Regions Mediate Glucocorticoid Responsiveness," J. Virology, 62:1314, 1988.

Chandler, Maler, and Yamamoto, "DNA Sequences Bound Specifically by Glucocorticoid Receptor in vitro Render a Heterlogous Promoter Hormone Responsive in vivo," Cell, 33:489, 1983.

Chandler et al., "RNA splicing specificity determined by the coordinated action of RNA recognition motifs in SR proteins," Proc Natl Acad Sci USA. 94(8):3596-3601, 1997.

Chang, Erwin, and Lee, "Glucose-regulated Protein (GRP94 and GRP78) Genes Share Common Regulatory Domains and are Coordinately Regulated by Common Trans-acting Factors," Mol. Cell. Biol., 9:2153, 1989.

Charneau, Mirambeau, Roux, Paulous, Buc, Clavel, "HIV-1 reverse transcription: a termination step at the center of the genome," J. Mol. Biol. 241:651-662, 1994.

Chatterjee, Lee, Rentoumis, and Jameson, "Negative Regulation of the Thyroid-Stimulating Hormone Alpha Gene by Thyroid Hormone: Receptor Interaction Adjacent to the TATA Box," Proc Natl. Acad. Sci. U.S.A., 86:9114, 1989.

Chen and Okayama, "High-efficiency transformation of mammalian cells by plasmid DNA," Mol. Cell. Biol. 7:2745-2752, 1987

Cherrington and Ganem, "Regulation of polyadenylation in human immunodeficiency virus (HIV): contributions of promoter proximity and upstream sequences," Embo. J., 11:1513-1524, 1992.

Choi, Chen, Kriegler, and Roninson, "An altered pattern of cross-resistance in multi-drug-resistant human cells results from spontaneous mutations in the mdr-1 (p-glycoprotein) gene," Cell, 53:519, 1988.

Cocea, "Duplication of a region in the multiple cloning site of a plasmid vector to enhance cloning-mediated addition of restriction sites to a DNA fragment," Biotechniques, 23:814-816, 1997.

Cohen, Walter, and Levinson, "A Repetitive Sequence Element 3' of the Human c-Ha-ras1 Gene Has Enhancer Activity," J. Cell. Physiol., 5:75, 1987.

Corbeau, et al., PNAS (U.S.A.,) 93(24):14070-14075, 1996.

Costa, Lai, Grayson, and Darnell, "The Cell-Specific Enhancer of the Mouse Transthyretin (Prealbumin) Gene Binds a Common Factor at One Site and a Liver-Specific Factor(s) at Two Other Sites," Mol. Cell. Biol., 8:81, 1988.

Cripe, Haugen, Turk, Tabatabai, Schmid, Durst, Gissmann, Roman, and Turek, "Transcriptional Regulation of the Human Papilloma Virus-16 E6-E7 Promoter by a Keratinocyte-Dependent Enhancer, and by Viral E2 Trans-Activator and Repressor Gene Products: Implications for Cervical Carcinogenesis," EMBO J., 6:3745, 1987.

Culotta and Hamer, "Fine Mapping of a Mouse Metallothionein Gene Metal-Response Element," Mol. Cell. Biol., 9:1376, 1989.

Dandolo, Blangy, and Kamen, "Regulation of Polyma Virus Transcription in Murine Embryonal Carcinoma Cells," J. Virology, 47:55, 1983.

Das, Klaver, Klasens, van Wamel, "A conserved hairpin motif in the R-U5 region of the human immunodeficiency virus type 1 RNA genome is essential for replication," J. Virol. 71:2346-2356.

Dao, Hannum, Kohn, Nolta, "FLT3 ligand preserves the ability of human CD34+ progenitors to sustain long-term hematopoiesis in immune-deficient mice after ex vivo retroviral-mediated transduction," Blood, 89:446-456, 1997.

Dao, Hashino, Kato, Nolta, "Adhesion to fibronectin maintains regenerative capacity during ex vivo, culture and transduction of human hematopoietic stem and progenitor cells," Blood, 92:4612-4621, 1998.

Deschamps, Meijlink, and Verma, "Identification of a Transcriptional Enhancer Element Upstream From the Proto-Oncogene Fos," Science, 230:1174, 1985.

De Villiers, Schaffner, Tyndall, Lupton, and Kamen, "Polyoma Virus DNA Replication Requires an Enhancer," Nature, 312:242, 1984.

DeZazzo, Kilpatrick, Imperiale, "Involvement of long terminal repeat U3 sequences overlapping the transcription control region in human immunodeficiency virus type 1 mRNA 3' end formation," Mol. Cell. Biol., 11:1624-1630, 1991.

Donello, Loeb, Hope, "Woodchuck hepatitis virus contains a tripartite posttranscriptional regulatory element," J. Virol., 72:5085-5092, 1998.

Dorrell, Gan, Pereira, Hawley, Dick, "Expansion of human cord blood CD34(+)CD38(-) cells in ex vivo culture during retroviral transduction without a corresponding increase in SCID repopulating cell (SRC) frequency: dissociation of SRC phenotype and function," Blood, 95:102-110, 2000.

Dull, Zufferey, Kelly, Mandel, Nguyen, Trono, Naldini, "A third generation lentivirus vector with a conditional packaging system," J. Virol., 72:8463-8471, 1998.

Edbrooke, Burt, Cheshire, and Woo, "Identification of cis-acting sequences responsible for phorbol ester induction of human serum amyloid a gene expression via a nuclear-factor-kappa β-like transcription factor," Mol. Cell. Biol., 9:1908, 1989.

Edlund, Walker, Barr, and Rutter, "Cell-specific expression of the rat insulin gene: evidence for role of two distinct 5' flanking elements," Science, 230:912, 1985.

Fechheimer, Boylan, Parker, Sisken, Patel and Zimmer, "Transfection of mammalian cells with plasmid DNA by scrape loading and sonication loading," Proc Nat'l. Acad. Sci. USA 84:8463-8467, 1987

Feng and Holland, "HIV-I Tat Trans-Activation Requires the Loop Sequence Within Tar," Nature, 334:6178, 1988.

Firak and Subramanian, "Minimal Transcription Enhancer of Simian Virus 40 is a 74-Base-Pair Sequence that Has Interacting Domains," Mol. Cell. Biol., 6:3667, 1986.

Foecking and Hofstetter, "Powerful and Versatile Enhancer-Promoter Unit for Mammalian Expression Vectors," Gene, 45(1):101-105, 1986.

Froehler, Ng, Matteucci, "Synthesis of DNA via deoxynucleoside H-phosphonate intermediates." Nuc. Acids Res. 14:5399-407, 1986.

Fujita, Shibuya, Hotta, Yamanishi, and Taniguchi, "Interferon-Beta Gene Regulation: Tandemly Repeated Sequences of a Synthetic 6-bp Oligomer Function as a Virus-Inducible Enhancer," *Cell*, 49:357, 1987.

Gilles, Morris, Oi, and Tonegawa, "A tissue-specific transcription enhancer element is located in the major intron of a rearranged immunoglobulin heavy-chain gene," *Cell*, 33:717, 1983.

Gilmartin, Fleming, Oetjen, "Activation of HIV-1 pre-mRNA 3' processing in vitro requires both an upstream element and TAR," *Embo. J.*, 11:4419-4428, 1992.

Gloss, Bernard, Seedorf, and Klock, "The Upstream Regulatory Region of the Human Papilloma Virus-16 Contains an E2 Protein-Independent Enhancer Which is Specific for Cervical Carcinoma Cells and Regulated by Glucocorticoid Hormones," *EMBO J.*, 6:3735, 1987.

Godbout, Ingram, and Tilghman, "Fine-Structure Mapping of the Three Mouse Alpha-Fetoprotein Gene Enhancers," *Mol. Cell. Biol.*, 8:1169, 1988.

Goodbourn, Burstein, and Maniatis, "The Human Beta-Interferon Gene Enhancer is Under Negative Control," *Cell*, 45:601, 1986.

Goodbourn and Maniatis, "Overlapping Positive and Negative Regulatory Domains of the Human β-Interferon Gene," *Proc. Natl. Acad. Sci. USA*, 85:1447, 1988.

Gopal, "Gene transfer method for transient gene expression, stable transformation, and cotransformation of suspension cell cultures," *Mol. Cell. Biol.* 5:1188-1190, 1985.

Gossen and Bujard, *Proc. Natl. Acad. Sci.*, 89:5547-5551, 1992.

Graham and Van Der Eb, "A new technique for the assay of infectivity of human adenovirus 5 DNA," *Virology* 52:456-467, 1973

Greco and Dachs, "Gene directed enzyme/prodrug therapy of cancer: historical appraisal and future prospectives," *J. Cell. Phys.* 187: 22-36, 2001

Greene, Bohnlein, and Ballard, "HIV-1, and Normal T-Cell Growth: Transcriptional Strategies and Surprises," *Immunology Today*, 10:272, 1989

Grosschedl and Baltimore, "Cell-Type Specificity of Immunoglobulin Gene Expression is Regulated by at Least Three DNA Sequence Elements," *Cell*, 41:885, 1985.

Haslinger and Karin, "Upstream Promoter Element of the Human Metallothionein-II Gene Can Act Like an Enhancer Element," *Proc Natl. Acad. Sci. U.S.A.*, 82:8572, 1985.

Hauber and Cullen, "Mutational Analysis of the Trans-Activation-Responsive Region of the Human Immunodeficiency Virus Type I Long Terminal Repeat," *J. Virology*, 62:673, 1988.

Hen, Borrelli, Fromental, Sassone-Corsi, and Chambon, "A Mutated Polyoma Virus Enhancer Which is Active in Undifferentiated Embryonal Carcinoma Cells is not Repressed by Adenovirus-2 E1A Products," *Nature*, 321:249, 1986.

Hensel, Meichle, Pfizenmaier, and Kronke, "PMA-Responsive 5'Flanking Sequences of the Human TNF Gene," *Lymphokine Res.*, 8:347, 1989.

Herr and Clarke, "The SV40 Enhancer is Composed of Multiple Functional Elements That Can Compensate for One Another," *Cell*, 45:461, 1986.

Hirochika, Browker, and Chow, "Enhancers and Trans-Acting E2 Transcriptional Factors of Papilloma Viruses," *J. Virol.*, 61:2599, 1987.

Hirsch, Gaugler, Deagostini-Bauzin, Bally-Cuif, and Gordis, "Identification of Positive and Negative Regulatory Elements Governing Cell-Type-Specific Expression of the Neural-Cell-Adhesion-Molecule Gene," *Mol. Cell. Biol.*, 10:1959, 1990.

Holbrook, Gulino, and Ruscetti, "cis-Acting Transcriptional Regulatory Sequences in the Gibbon Ape Leukemia Virus (GALV) Long Terminal Repeat," *Virology*, 157:211, 1987.

Horlick and Benfield, "The upstream muscle-specific enhancer of the rat muscle creatine kinase gene is composed of multiple elements," *Mol. Cell. Biol.*, 9:2396, 1989.

Huang, Ostrowski, Berard, and Hagar, "Glucocorticoid regulation of the ha-musv p21 gene conferred by sequences from mouse mammary tumor virus," *Cell*, 27:245, 1981.

Hug, Costas, Staeheli, Aebi, and Weissmann, "Organization of the Murine Mx Gene and Characterization of its Interferon- and Virus-Inducible Promoter," *Mol. Cell. Biol.*, 8:3065, 1988.

Hwang, Lim, and Chae, "Characterization of the S-Phase-Specific Transcription Regulatory Elements in a DNA-Replication-Independent Testis-Specific H2B (TH2B) Histone Gene," *Mol. Cell. Biol.*, 10:585, 1990.

Imagawa, Chiu, and Karin, "Transcription Factor AP-2 Mediates Induction by Two Different Signal-Transduction Pathways: Protein Kinase C and cAMP," *Cell*, 51:251, 1987.

Imbra and Karin, "Phorbol Ester Induces the Transcriptional Stimulatory Activity of the SV40 Enhancer," *Nature*, 323:555, 1986.

Imler, Lemaire, Wasvlyk, and Waslyk, "Negative Regulation Contributes to Tissue Specificity of the Immunoglobulin Heavy-Chain Enhancer," *Mol. Cell. Biol*, 7:2558, 1987.

Imperiale and Nevins, "Adenovirus 5 E2 Transcription Unit: an E1A-Inducible Promoter with an Essential Element that Functions Independently of Position or Orientation," *Mol. Cell. Biol.*, 4:875, 1984.

Jakobovits, Smith, Jakobovits, and Capon, "A Discrete Element 3' of Human Immunodeficiency Virus 1 (HIV-1) and HIV-2 mRNA Initiation Sites Mediates Transcriptional Activation by an HIV Trans-Activator," *Mol. Cell. Biol.*, 8:2555, 1988.

Jameel and Siddiqui, "The Human Hepatitis B Virus Enhancer Requires Transacting Cellular Factor(s) for Activity," *Mol. Cell. Biol.*, 6:710, 1986.

Jaynes, Johnson, Buskin, Gartside, and Hauschka, "The Muscle Creatine Kinase Gene is Regulated by Multiple Upstream Elements, Including a Muscle-Specific Enhancer," *Mol. Cell. Biol.*, 8:62, 1988.

Johnson, Wold, and Hauschka, "Muscle creatine kinase sequence elements regulating skeletal and cardiac muscle expression in transgenic mice," *Mol. Cell. Biol.*, 9:3393, 1989.

Kadesch and Berg, "Effects of the Position of the Simian Virus 40 Enhancer on Expression of Multiple Transcription Units in a Single Plasmid," *Mol. Cell. Biol.*, 6:2593, 1986.

Kafri, et al., "Sustained expression of genes delivered directly into liver and muscle by lentiviral vectors," *Nat. Genetics*, 17:314-317, 1997.

Karin, Haslinger, Heguy, Dietlin, and Cooke, "Metal-Responsive Elements Act as Positive Modulators of Human Metallothionein-IIA Enhancer Activity," *Mol. Cell. Biol.*, 7:606, 1987.

Katinka, Yaniv, Vasseur, and Blangy, "Expression of Polyoma Early Functions in Mouse Embryonal Carcinoma Cells Depends on Sequence Rearrangements in the Beginning of the Late Region," *Cell*, 20:393, 1980.

Kawamoto, Makino, Niw, Sugiyama, Kimura, Anemura, Nakata, and Kakunaga, "Identification of the Human Beta-Actin Enhancer and its Binding Factor," *Mol. Cell. Biol.*, 8:267, 1988.

Kiledjian, Su, Kadesch, "Identification and characterization of two functional domains within the murine heavy-chain enhancer," Mol. Cell. Biol., 8:145, 1988.

Klages, Zufferey, Trono, "A stable system for the high-titer production of multiply aattenuated lentiviral vectors," Mol. Ther. 2:170-176, 2000.

Klamut, Gangopadyhay, Worton, and Ray, "Molecular and Functional Analysis of the Muscle-Specific Promoter Region of the Duchenne Muscular Dystrophy Gene," Mol. Cell. Biol., 10:193, 1990.

Klein et al., "High-velocity microprojectiles for delivering nucleic acids into living cells," Nature, 327:70-73, 1987.

Koch, Benoist, and Mathis, "Anatomy of a new β-cell-specific enhancer," Mol. Cell. Biol., 9:303, 1989.

Kohn, Nolta, Weinthal, Bahner, Yu, Lilley, Crooks, "Toward gene therapy for Gaucher disease," Hum. Gene Ther., 2:101-105, 1991.

Kotsopoulou, Kim, Kingsman, Kingsman, Mitrophanous. "A Rev-independent human immunodeficiency virus type 1 (HIV-1)-based vector that exploits a codon-optimized HIV-1 gag-pol gene," J. Virol. 74:4839-52, 2000.

Kraus et al., "Alternative promoter usage and tissue specific expression of the mouse somatostatin receptor 2 gene," FEBS Lett., 428(3):165-170, 1998.

Kriegler and Botchan, "A retrovirus LTR contains a new type of eukaryotic regulatory element," In: Eukaryotic Viral Vectors, Gluzman (ed.), Cold Spring Harbor, Cold Spring Harbor Laboratory, NY, 1982.

Kriegler et al., "Promoter substitution and enhancer augmentation increases the penetrance of the sv40 a gene to levels comparable to that of the harvey murine sarcoma virus ras gene in morphologic transformation," In: Gene Expression, Alan Liss (Ed.), Hamer and Rosenberg, New York, 1983.

Kriegler et al., "Viral Integration and Early Gene Expression Both Affect the Efficiency of SV40 Transformation of Murine Cells: Biochemical and Biological Characterization of an SV40 Retrovirus," In: Cancer Cells 2/Oncogenes and Viral Genes, Van de Woude et al. (eds), Cold Spring Harbor, Cold Spring Harbor Laboratory, 1984.

Kriegler, Perez, Defay, Albert and Liu, "A Novel Form of TNF/Cachectin Is a Cell-Surface Cytotoxix Transmembrane Protein: Ramifications for the Complex Physiology of TNF," Cell, 53:45, 1988.

Kuhl, De La Fuenta, Chaturvedi, Parinool, Ryals, Meyer, and Weissman, "Reversible Silencing of Enhancers by Sequences Derived From the Human IFN-alpha Promoter," Cell, 50:1057, 1987.

Kunz, Zimmerman, Heisig, and Heinrich, "Identification of the Promoter Sequences Involved in the Interleukin-6-Dependent Expression of the Rat Alpha-2-Macroglobulin Gene," Nucl. Acids Res., 17:1121, 1989.

Lareyre et al., "A 5-kilobase pair promoter fragment of the murine epididymal retinoic acid-binding protein gene drives the tissue-specific, cell-specific, and androgen-regulated expression of a foreign gene in the epididymis of transgenic mice," J Biol Chem., 274(12):8282-8290, 1999.

Larsen, Harney, and Moore, "Repression medaites cell-type-specific expression of the rat growth hormone gene," Proc Natl. Acad. Sci. USA., 83:8283, 1986.

Laspia, Rice, and Mathews, "HIV-1 Tat protein increases transcriptional initiation and stabilizes elongation," Cell, 59:283, 1989.

Latimer, Berger, and Baumann, "Highly conserved upstream regions of the alpha.sub.1-antitrypsin gene in two mouse species govern liver-specific expression by different mechanisms," Mol. Cell. Biol., 10:760, 1990.

Lee, Mulligan, Berg, and Ringold, "Glucocorticoids Regulate Expression of Dihydrofolate Reductase cDNA in Mouse Mammary Tumor Virus Chimaeric Plasmids," Nature, 294:228, 1981.

Lee et al., "Activation of beta3-adrenoceptors by exogenous dopamine to lower glucose uptake into rat adipocytes," J Auton Nerv Syst. 74(2-3):86-90, 1997.

Levenson et al., "Internal ribosomal entry site-containing retroviral vectors with green fluorescent protein and drug resistance markers," Human Gene Therapy, 9:1233-1236, 1998.

Levinson, Khoury, VanDeWoude, and Gruss, "Activation of SV40 Genome by 72-Base-Pair Tandem Repeats of Moloney Sarcoma Virus," Nature, 295:79, 1982. Lewis and Emerman, "Passage through mitosis is required for oncoretroviruses but not for the human immunodeficiency virus," J. Virol., 68:510-516, 1994.

Lin, Cross, Halden, Dragos, Toledano, and Leonard, "Delineation of an enhancerlike positive regulatory element in the interleukin-2 receptor .alpha.-chain gene," Mol. Cell. Biol., 10:850, 1990.

Luria, Gross, Horowitz, and Givol, "Promoter Enhancer Elements in the Rearranged Alpha-Chain Gene of the Human T-Cell Receptor," EMBO J., 6:3307, 1987.

Lusky, Berg, Weiher, and Botchan, "Bovine Papilloma Virus Contains an Activator of Gene Expression at the Distal End of the Early Transcription Unit," Mol. Cell. Biol. 3:1108, 1983.

Lusky and Botchan, "Transient Replication of Bovine Papilloma Virus Type 1 Plasmids: cis and trans Requirements," Proc Natl. Acad. Sci. U.S.A., 83:3609, 1986.

Majors and Varmus, "A Small Region of the Mouse Mammary Tumor Virus Long Terminal Repeat Confers Glucocorticoid Hormone Regulation on a Linked Heterologous Gene," Proc. Natl. Acad. Sci. U.S.A., 80:5866, 1983.

Marthas et al. J. Virol., 67:6047-6055, 1993.

Mazurier, Moreau-Gaudry, Maguer-Satta, Salesse, Pigeonnier-Lagarde, Ged, Belloc, Lacombe, Mahon, Reiffers, de Verneuil, "Rapid analysis and efficient selection of human transduced primitive hematopoietic cells using the humanized S65T green fluorescent protein," Gene Ther., 5:556-562, 1998.

McNeall, Sanchez, Gray, Chesterman, and Sleigh, "Hyperinducible Gene Expression From a Metallotionein Promoter Containing Additional Metal-Responsive Elements," Gene, 76:81, 1989.

Miksicek, Heber, Schmid, Danesch, Posseckert, Beato, and Schutz, "Glucocorticoid Responsiveness of the Transcriptional Enhancer of Moloney Murine Sarcoma Virus," Cell, 46:203, 1986.

Miyoshi, Smith, Mosier, Verma, Torbett, "Transduction of human CD34+ cells that mediate long-term engraftment of NOD/SCID mice by HIV vectors," Science, 283:682-686, 1999.

Mizushima and Nagata, "pEF-BOS, a powerful mammalian expression vector," Nucleic Acids Res., 18:5322, 1990.

Mordacq and Linzer, "Co-localization of Elements Required for Phorbol Ester Stimulation and Glucocorticoid Repression of Proliferin Gene Expression," Genes and Dev., 3:760, 1989.

Moreau, Hen, Wasylyk, Everett, Gaub, and Chambon, "The SV40 base-repair repeat has a striking effect on gene expression both in sv40 and other chimeric recombinants," Nucl. Acids Res., 9:6047, 1981.

Muesing et al., *Cell,* 48:691, 1987.

Naldini, Blomer, gallay, Ory, Mulligan, Gage, Verma, Trono, "In vivo gene delivery and stable transduction of nondividing cells by a lentiviral vector," *Science,* 272:263-267, 1996a.

Naldini, Blomer, Gage, Trono, Verma, "Efficient transfer, integration, and sustained long-term expression of the transgene in adult rat brains injected with a lentiviral vector," *Proc. Natl. Acad. Sci. USA,* 93:11382-11388, 1996b.

Naldini, "Lentiviruses as gene transfer agents for delivery to non-dividing cells," *Curr. Opin. Biotechnol.* 9:457-463, 1998.

Ng, Gunning, Liu, Leavitt, and Kedes, "Regulation of the Human Beta-Actin Promoter by Upstream and Intron Domains," *Nuc. Acids Res.,* 17:601, 1989.

Nomoto et al., "Cloning and characterization of the alternative promoter regions of the human LIMK2 gene responsible for alternative transcripts with tissue-specific expression," *Gene,* 236(2):259-271, 1999.

Ornitz, Hammer, Davison, Brinster, and Palmiter, "Promoter and enhancer elements from the rat elastase i gene function independently of each other and of heterologous enhancers," Mol. Cell. Biol. 7:3466, 1987.

Ondek, Sheppard, and Herr, "Discrete Elements Within the SV40 Enhancer Region Display Different Cell-Specific Enhancer Activities," *EMBO J.,* 6:1017, 1987.

Ory et al., *Proc. Natl. Acad. Sci.,* 93:11400-11406, 1996.

Palmiter, Chen, and Brinster, "Differential regulation of metallothionein-thymidine kinase fusion genes in transgenic mice and their offspring," *Cell,* 29:701, 1982.

Pech, Rao, Robbins, and Aaronson, "Functional identification of regulatory elements within the promoter region of platelet-derived growth factor 2," *Mol. Cell. Biol.,* 9:396, 1989.

Perez-Stable and Constantini, "Roles of fetal γ-globin promoter elements and the adult β-globin 3' enhancer in the stage-specific expression of globin genes," *Mol. Cell. Biol.,* 10:1116, 1990.

Piacibello, Sanavio, Severino, Dane, Gammaitoni, Fagioli, Perissinotto, Cavalloni, Kollet Lapidot, Aglietta, "Engraftment in nonobese diabetic severe combined immunodeficient mice of human CD34(+) cord blood cells after ex vivo expansion: evidence for the amplification and self-renewal of repopulating stem cells," *Blood,* 93:3736-3749, 1999.

Picard and Schaffner, "A Lymphocyte-Specific Enhancer in the Mouse Immunoglobulin Kappa Gene," *Nature,* 307:83, 1984.

Pinkert, Ornitz, Brinster, and Palmiter, "An albumin enhancer located 10 kb upstream functions along with its promoter to direct efficient, liver-specific expression in transgenic mice," *Genes and Dev.,* 1:268, 1987.

Ponta, Kennedy, Skroch, Hynes, and Groner, "Hormonal Response Region in the Mouse Mammary Tumor Virus Long Terminal Repeat Can Be Dissociated From the Proviral Promoter and Has Enhancer Properties," *Proc. Natl. Acad. Sci. U.S.A.,* 82:1020, 1985.

Porton, Zaller, Lieberson, and Eckhardt, "Immunoglobulin heavy-chain enhancer is required to maintain transfected .gamma.2a gene expression in a pre-b-cell line," *Mol. Cell. Biol.,* 10:1076, 1990.

Potter et al., "Enhancer-dependent expression of human k immunoglobulin genes introduced into mouse pre-B lymphocytes by electroporation," *Proc Nat'l Acad. Sci. USA,* 81:7161-7165, 1984.

Queen and Baltimore, "Immunoglobulin Gene Transcription is Activated by Downstream Sequence Elements," *Cell,* 35:741, 1983.

Quinn, Farina, Gardner, Krutzsch, and Levens, "Multiple components are required for sequence recognition of the ap1 site in the gibbon ape leukemia virus enhancer," *Mol. Cell. Biol.,* 9:4713, 1989.

Redondo, Hata, Brocklehurst, and Krangel, "A T-Cell-Specific Transcriptional Enhancer Within the Human T-Cell Receptor .delta. Locus," *Science,* 247:1225, 1990.

Resendez Jr., Wooden, and Lee, "Identification of highly conserved regulatory domains and protein-binding sites in the promoters of the rat and human genes encoding the stress-inducible 78-kilodalton glucose-regulated protein," *Mol. Cell. Biol.,* 8:4579, 1988.

Reisman and Rotter, "Induced Expression From the Moloney Murine Leukemia Virus Long Terminal Repeat During Differentiation of Human Myeloid Cells is Mediated Through its Transcriptional Enhancer," *Mol. Cell. Biol.,* 9:3571, 1989.

Remington's Pharmaceutical Sciences, 15$^{th}$ Ed., pages 1035-1038 and 1570-1580.

Ripe, Lorenzen, Brenner, and Breindl, "Regulatory elements in the 5' flanking region and the first intron contribute to transcriptional control of the mouse alpha-1-type collagen gene," *Mol. Cell. Biol.,* 9:2224, 1989.

Rippe, Brenner and Leffert, "DNA-mediated gene transfer into adult rat hepatocytes in primary culture," *Mol. Cell Biol.,* 10:689-695, 1990.

Rittling, Coutinho, Amarm, and Kolbe, "AP-1/jun-binding Sites Mediate Serum Inducibility of the Human Vimentin Promoter," *Nuc. Acids Res.,* 17:1619, 1989.

Roe, Reynolds, Yu, Brown, "Integration of murine leukemia virus DNA depends on mitosis," *Embo. J.,* 12:2099-2108, 1993.

Rosen, Sodroski, and Haseltine, "The location of cis-acting regulatory sequences in the human t-cell lymphotropic virus type III (HTLV-111/LAV) long terminal repeat," *Cell,* 41:813, 1988.

Sakai, Helms, Carlstedt-Duke, Gustafsson, Rottman, and Yamamoto, "Hormone-Mediated Repression: A Negative Glucocorticoid-Response Element From the Bovine Prolactin Gene," *Genes and Dev.,* 2:1144, 1988.

Sambrook, Fritsch, Maniatis, In: *Molecular Cloning: A Laboratory Manual* 2 rev. ed., Cold Spring Harbor, Cold Spring Harbor Laboratory Press, 1(77):19-17.29, 1989.

Satake, Furukawa, and Ito, "Biological activities of oligonucleotides spanning the f9 point mutation within the enhancer region of polyoma virus DNA," *J. Virology,* 62:970, 1988.

Scharfmann, Axelrod, Verma, "Long-term in vivo expression of retrovirus-mediated gene transfer in mouse fibroblast implants," *Proc. Natl. Acad. Sci. USA,* 88:4626-4630, 1991.

Schaffner, Schirm, Muller-Baden, Wever, and Schaffner, "Redundancy of Information in Enhancers as a Principle of Mammalian Transcription Control," *J. Mol. Biol.,* 201:81, 1988.

Schmid, Uittenbogaart, Keld, Giorgi, "A rapid method for measuring apoptosis and dual-color immunofluorescence by single laser flow cytometry," *J. Immunol. Methods,* 170:145-157, 1994.

Searle, Stuart, and Palmiter, "Building a metal-responsive promoter with synthetic regulatory elements," *Mol. Cell. Biol.,* 5:1480, 1985.

Sharp and Marciniak, "HIV Tar: an RNA Enhancer?," *Cell,* 59:229, 1989.

Shaul and Ben-Levy, "Multiple Nuclear Proteins in Liver Cells are Bound to Hepatitis B Virus Enhancer Element and its Upstream Sequences," *EMBO J.,* 6:1913, 1987.

Sherman, Basta, Moore, Brown, and Ting, "Class II Box Consensus Sequences in the HLA-DR.alpha. Gene: Transcriptional Function and Interaction with Nuclear Proteins," Mol. Cell. Biol., 9:50, 1989.

Sleigh and Lockett, "SV40 Enhancer Activation During Retinoic-Acid-Induced Differentiation of F9 Embryonal Carcinoma Cells," J. EMBO, 4:3831, 1985.

Spalholz, Yang, and Howley, "Transactivation of a Bovine Papilloma Virus Transcriptional Regulatory Element by the E2 Gene Product," Cell, 42:183, 1985.

Spandau and Lee, "Trans-Activation of Viral Enhancers by the Hepatitis B Virus X Protein," J. Virology, 62:427, 1988.

Spandidos and Wilkie, "Host-Specificities of Papilloma Virus, Moloney Murine Sarcoma Virus and Simian Virus 40 Enhancer Sequences," EMBO J., 2:1193, 1983.

Stephens and Hentschel, "The Bovine Papilloma Virus Genome and its Uses as a Eukaryotic Vector," Biochem. J., 248:1, 1987.

Stuart, Searle, and Palmiter, "Identification of Multiple Metal Regulatory Elements in Mouse Metallothionein-I Promoter by Assaying Synthetic Sequences," Nature, 317:828, 1985.

Sullivan and Peterlin, "Transcriptional Enhancers in the HLA-DQ Subregion," Mol. Cell. Biol., 7:3315, 1987.

Sutton, Reitsma, Uchida, Brown, "Transduction of human progenitor hematopoietic stem cells by human immunodeficiency virus type 1-based vectors is cell cycle dependent," J. Virol., 73:3649-3660, 1999.

Sutton, Wu, Rigg, Bohnlein, Brown, "Human immunodeficiency virus type 1 vectors efficiently transduce human hematopoietic stem cells,"" J. Virol., 72:5781-5788, 1998.

Swartzendruber and Lehman, "Neoplastic Differentiation: Interaction of Simian Virus 40 and Polyoma Virus with Murine Teratocarcinoma Cells," J. Cell. Physiology, 85:179, 1975.

Takebe, Seiki, Fujisawa, Hoy, Yokota, Arai, Yoshida, and Arai, "SR.alpha. Promoter: An Efficient and Versatile Mammalian cDNA Expression System Composed of the Simian Virus 40 Early Promoter and the R-U5 Segment of Human T-Cell Leukemia Virus Type 1 Long Terminal Repeat," Mol. Cell. Biol., 8:466, 1988.

Taylor and Kingston, "E1A Trans-Activation of Human HSP70 Gene Promoter Substitution Mutants is Independent of the Composition of Upstream and TATA Elements," Mol. Cell. Biol., 10:176, 1990.

Taylor and Kingston, "Factor Substitution in a Human HSP70 Gene Promoter: TATA-Dependent and TATA-Independent Interactions," Mol. Cell. Biol., 10:165, 1990.

Taylor, Solomon, Weiner, Paucha, Bradley, and Kingston, "Stimulation of the Human Heat-Shock Protein 70 Promoter in vitro by Simian Virus 40 Large T Antigen," J. Biol. Chem., 264:15160, 1989.

Tavernier, Gheysen, Duerinck, Can Der Heyden, and Fiers, "Deletion Mapping of the Inducible Promoter of Human IFN-beta Gene," Nature, 301:634, 1983.

Thiesen, Bosze, Henry, and Charnay, "A DNA Element Responsible for the Different Tissue Specificities of Friend and Moloney Retroviral Enhancers," J. Virology, 62:614, 1988.

Tronche, Rollier, Bach, Weiss, and Yaniv, "The Rat Albumin Promoter: Cooperation with Upstream Elements is Required When Binding of APF/HNF 1 to the Proximal Element is Partially Impaired by Mutation or Bacterial Methylation," Mol. Cell Biol., 9:4759, 1989.

Tronche, Rollier, Herbomel, Bach, Cereghini, Weiss, and Yaniv, "Anatomy of the Rat Albumin Promoter," Mol. Biol. Med., 7:173, 1990.

Trudel and Constantini, "A 3' Enhancer Contributes to the Stage-Specific Expression of the human Beta-Globin Gene," Genes and Dev., 6:954, 1987.

Tsumaki et al., "Modular arrangement of cartilage- and neural tissue-specific cis-elements in the mouse alpha2(XI) collagen promoter," J Biol Chem. 273(36):22861-22864, 1998.

Tur-Kaspa, Teicher, Levine, Skoultchi and Shafritz, "Use of electroporation to introduce biologically active foreign genes into primary rat hepatocytes," Mol. Cell Biol., 6:716-718, 1986.

Tyndall, La Mantia, Thacker, Favaloro, and Kamen, "A Region of the Polyoma Virus Genome Between the Replication Origin and Late Protein-Coding Sequences is Required in cis for Both Early Gene Expression and Viral DNA Replication," Nuc. Acids. Res., 9:6231, 1981.

Uchida, Sutton, Friera, He, Reitsma, Chang, Veres, Scollay, Weissman, "HIV, but not murine leukemia virus, vectors mediate high efficiency gene transfer into freshly isolated G0/G1 human hematopoietic stem cells," Proc. Natl. Acad. Sci. USA, 95:11939-11944, 1998.

Ueda, Tsuji, Yoshino, Ebihara, Yagasaki, Hisakawa, Mitsui, Manabe, Tanaka, Kobayashi, Ito, Yasukawa, Nakahata, "Expansion of human NOD/SCID-repopulating cells by stem cell factor, Flk2/Flt3 ligand, thrombopoietin, IL-6, and soluble IL-6 receptor," J. Clin. Invest., 105:1013-1021, 2000.

Unutmaz, Kewal, Ramani, Marmon, Littman, "Cytokine signals are sufficient for HIV-1 infection of resting human T lymphocytes," J. Exp. Med., 189:1735-1746, 1999.

Valsamakis, Schek, Alwine, "Elements upstream of the AAUAAA within the human immunodeficiency virus polyadenylation signal are required for efficient polyadenylation in vitro," Mol. Cell Biol., 12:3699-3705, 1992.

Valsamakis, Zeichner, Carswell, Alwine, "The human immunodeficiency virus type 1 polyadenylylation signal: a 3' long terminal repeat element upstream of the AAUAAA necessary for efficient polyadenylylation," Proc. Natl. Acad. Sci. USA, 88:2108-2112, 1991.

Vannice and Levinson, "Properties of the Human Hepatitis B Virus Enhancer: Position Effects and Cell-Type Nonspecificity," J. Virology, 62:1305, 1988.

Vasseur, Kress, Montreau, and Blangy, "Isolation and Characterization of Polyoma Virus Mutants Able to Develop in Multipotential Murine Embryonal Carcinoma Cells," Proc Natl. Acad. Sci. U.S.A., 77:1068, 1980.

Wang and Calame, "SV40 enhancer-binding factors are required at the establishment but not the maintenance step of enhancer-dependent transcriptional activation," Cell, 47:241, 1986.

Watanabe et al., "Gene transfection of mouse primordial germ cells in vitro and analysis of their survival and growth control, Experimental Cell Research, 230:76-83, 1997.

Weber, De Villiers, and Schaffner, "An SV40 'Enhancer Trap' Incorporates Exogenous Enhancers or Generates Enhancers From its Own Sequences," Cell, 36:983, 1984.

Weinberger, Jat, and Sharp, "Localization of a Repressive Sequence Contributing to B-cell Specificity in the Immunoglobulin Heavy-Chain Enhancer," Mol. Cell. Biol., 8:988, 1984.

Winoto and Baltimore, "αβ-lineage-specific Expression of the α T-Cell Receptor Gene by Nearby Silencers," Cell, 59:649, 1989.

Wu et al., "Promoter-dependent tissue-specific expressive nature of imprinting gene, insulin-like growth factor II, in human tissues," Biochem Biophys Res Commun. 233(1):221-226, 1997.

Wu, Wakefield, Liu, Xiao, Kralovics, Prchal, Kappes, "Development of a novel trans-lentiviral vector that affords predictable safety," *Mol. Ther.* 2:47-55, 2000.

Yang, Burkholder, Roberts, Martinell and McCabe, "In vivo and in vitro gene transfer to mammalian somatic cells by particle bombardment," *Proc Nat'l Acad Sci. USA,* 87:9568-9572, 1990.

Yutzey, Kline, and Konieczny, "An Internal Regulatory Element Controls Troponin I Gene Expression," *Mol. Cell. Biol.,* 9:1397, 1989.

Zennou, Petit, Guetard, Nerhbass, Mantagnier, Charneau, "HIV-1 genome nuclear import is mediated by a central DNA flap," *Cell* 101:173-185, 2000.

Zhao-Emonet et al., "The equine herpes virus 4 thymidine kinase is a better suicide gene than the human herpes virus 1 thymidine kinase," *Gene Ther.* 6(9):1638-1642, 1999.

Zufferey, Nagy, Mandel, Naldini, Trono, "Multiply attenuated lentiviral vector achieves efficient gene delivery in vivo," *Nat. Biotechnol.,* 15:871-875, 1997.

Zufferey, Dull, Mandel, Bukovsky, Quiroz, Naldini, Trono, "Self-inactivating lentivirus vector for safe and efficient in vivo gene delivery," *J. Virol.,* 72:9873-9880, 1998.

Zufferey, Donello, Trono, Hope, "Woodchuck hepatitis virus posttranscriptional regulatory element enhances expression of transgenes delivered by retroviral vectors," *J. Virol.,* 73:2886-2892, 1999.

Zufferey and Trono, Current Protocols in Neuroscience: unit 4.21: "High-titer production of lentiviral vectors," John Wiley & Sons, New York, 2000.

The invention claimed is:

1. The chimeric glycoprotein encoded by a nucleic acid comprising the sequence of SEQ ID NO: 1.

2. A nucleic acid encoding the chimeric glycoprotein of claim 1.

3. The nucleic acid of claim 2, wherein the nucleic acid comprises the sequence of SEQ ID NO: 1.

4. An expression construct comprising the nucleic acid of claim 2.

5. A cell transfected with the construct of claim 4.

6. A vector particle pseudotyped with the chimeric glycoprotein of claim 1, wherein the vector construct is derived from a lentivirus.

7. The vector particle of claim 6, wherein the vector construct is a recombinant viral vector construct.

8. The vector particle of claim 6, wherein the vector construct is derived from a simian immunodeficiency virus.

9. The vector particle of claim 6, wherein the vector construct is derived from a human immunodeficiency virus.

10. The vector particle of claim 7, wherein the vector construct further comprises a transgene.

11. The vector particle of claim 10, wherein the transgene is a marker or reporter gene.

12. The vector particle of claim 11, wherein the transgene is a gene encoding a green fluorescent protein (GFP).

13. The vector particle of claim 10, wherein the transgene is a therapeutic gene.

14. The vector particle of claim 13, wherein the transgene is an oncogene or a proto-oncogene.

15. The vector particle of claim 13, wherein the transgene is a drug susceptibility gene.

* * * * *

UNITED STATES PATENT AND TRADEMARK OFFICE
CERTIFICATE OF CORRECTION

PATENT NO. : 8,338,168 B2  
APPLICATION NO. : 10/512474  
DATED : December 25, 2012  
INVENTOR(S) : Trono et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1369 days.

Signed and Sealed this
Tenth Day of June, 2014

Michelle K. Lee
*Deputy Director of the United States Patent and Trademark Office*

SEQUENCE LISTING

```
<160> NUMBER OF SEQ ID NOS: 43

<210> SEQ ID NO 1
<211> LENGTH: 1689
<212> TYPE: DNA
<213> ORGANISM: Chimaera sp.
<220> FEATURE:
<221> NAME/KEY: CDS
<222> LOCATION: (1)..(1689)

<400> SEQUENCE: 1 atg aaa ctc cca aca gga atg gtc att tta tgt agc cta ata ata gtt      48
Met Lys Leu Pro Thr Gly Met Val Ile Leu Cys Ser Leu Ile Ile Val
  1               5                  10                  15 cgg gca ggg ttt gac gac ccc cgc aag gct atc gca tta gta caa aaa      96
Arg Ala Gly Phe Asp Asp Pro Arg Lys Ala Ile Ala Leu Val Gln Lys
             20                  25                  30 caa cat ggt aaa cca tgc gaa tgc agc gga ggg cag gta tcc gag gcc     144
Gln His Gly Lys Pro Cys Glu Cys Ser Gly Gly Gln Val Ser Glu Ala
         35                  40                  45 cca ccg aac tcc atc caa cag gta act tgc cca ggc aag acg gcc tac     192
Pro Pro Asn Ser Ile Gln Gln Val Thr Cys Pro Gly Lys Thr Ala Tyr
     50                  55                  60 tta atg acc aac caa aaa tgg aaa tgc aga gtc act cca aaa atc tca     240
Leu Met Thr Asn Gln Lys Trp Lys Cys Arg Val Thr Pro Lys Ile Ser
 65                  70                  75                  80 cct agc ggg gga gaa ctc cag aac tgc ccc tgt aac act ttc cag gac     288
Pro Ser Gly Gly Glu Leu Gln Asn Cys Pro Cys Asn Thr Phe Gln Asp
                 85                  90                  95 tcg atg cac agt tct tgt tat act gaa tac cgg caa tgc agg cga att     336
Ser Met His Ser Ser Cys Tyr Thr Glu Tyr Arg Gln Cys Arg Arg Ile
            100                 105                 110 aat aag aca tac tac acg gcc acc ttg ctt aaa ata cgg tct ggg agc     384
Asn Lys Thr Tyr Tyr Thr Ala Thr Leu Leu Lys Ile Arg Ser Gly Ser
        115                 120                 125 ctc aac gag gta cag ata tta caa aac ccc aat cag ctc cta cag tcc     432
Leu Asn Glu Val Gln Ile Leu Gln Asn Pro Asn Gln Leu Leu Gln Ser
    130                 135                 140 cct tgt agg ggc tct ata aat cag ccc gtt tgc tgg agt gcc aca gcc     480
Pro Cys Arg Gly Ser Ile Asn Gln Pro Val Cys Trp Ser Ala Thr Ala
145                 150                 155                 160 ccc atc cat atc tcc gat ggt gga gga ccc ctc gat act aag aga gtg     528
Pro Ile His Ile Ser Asp Gly Gly Gly Pro Leu Asp Thr Lys Arg Val
                165                 170                 175 tgg aca gtc caa aaa agg cta gaa caa att cat aag gct atg act cct     576
```

```
                Trp Thr Val Gln Lys Arg Leu Glu Gln Ile His Lys Ala Met Thr Pro
                            180                 185                 190 gaa ctt caa tac cac ccc tta gcc ctg ccc aaa gtc aga gat gac ctt           624
Glu Leu Gln Tyr His Pro Leu Ala Leu Pro Lys Val Arg Asp Asp Leu
        195                 200                 205 agc ctt gat gca cgg act ttt gat atc ctg aat acc act ttt agg tta           672
Ser Leu Asp Ala Arg Thr Phe Asp Ile Leu Asn Thr Thr Phe Arg Leu
    210                 215                 220 ctc cag atg tcc aat ttt agc ctt gcc caa gat tgt tgg ctc tgt tta           720
Leu Gln Met Ser Asn Phe Ser Leu Ala Gln Asp Cys Trp Leu Cys Leu
225                 230                 235                 240 aaa cta ggt acc cct acc cct ctt gcg ata ccc act ccc tct tta acc           768
Lys Leu Gly Thr Pro Thr Pro Leu Ala Ile Pro Thr Pro Ser Leu Thr
                245                 250                 255 tac tcc cta gca gac tcc cta gcg aat gcc tcc tgt cag att ata cct           816
Tyr Ser Leu Ala Asp Ser Leu Ala Asn Ala Ser Cys Gln Ile Ile Pro
            260                 265                 270 ccc ctc ttg gtt caa ccg atg cag ttc tcc aac tcg tcc tgt tta tct           864
Pro Leu Leu Val Gln Pro Met Gln Phe Ser Asn Ser Ser Cys Leu Ser
        275                 280                 285 tcc cct ttc att aac gat acg gaa caa ata gac tta ggt gca gtc acc           912
Ser Pro Phe Ile Asn Asp Thr Glu Gln Ile Asp Leu Gly Ala Val Thr
    290                 295                 300 ttt act aac tgc acc tct gta gcc aat gtc agt agt cct tta tgt gcc           960
Phe Thr Asn Cys Thr Ser Val Ala Asn Val Ser Ser Pro Leu Cys Ala
305                 310                 315                 320 cta aac ggg tca gtc ttc ctc tgt gga aat aac atg gca tac acc tat          1008
Leu Asn Gly Ser Val Phe Leu Cys Gly Asn Asn Met Ala Tyr Thr Tyr
                325                 330                 335 tta ccc caa aac tgg acc aga ctt tgc gtc caa gcc tcc ctc ctc ccc          1056
Leu Pro Gln Asn Trp Thr Arg Leu Cys Val Gln Ala Ser Leu Leu Pro
            340                 345                 350 gac att gac atc aac ccg ggg gat gag cca gtc ccc att cct gcc att          1104
Asp Ile Asp Ile Asn Pro Gly Asp Glu Pro Val Pro Ile Pro Ala Ile
        355                 360                 365 gat cat tat ata cat aga cct aaa cga gct gta cag ttc atc cct tta          1152
Asp His Tyr Ile His Arg Pro Lys Arg Ala Val Gln Phe Ile Pro Leu
    370                 375                 380 cta gct gga ctg gga atc acc gca gca ttc acc acc gga gct aca ggc          1200
Leu Ala Gly Leu Gly Ile Thr Ala Ala Phe Thr Thr Gly Ala Thr Gly
385                 390                 395                 400 cta ggt gtc tcc gtc acc cag tat aca aaa tta tcc cat cag tta ata          1248
Leu Gly Val Ser Val Thr Gln Tyr Thr Lys Leu Ser His Gln Leu Ile
                405                 410                 415 tct gat gtc caa gtc tta tcc ggt acc ata caa gat tta caa gac cag          1296
Ser Asp Val Gln Val Leu Ser Gly Thr Ile Gln Asp Leu Gln Asp Gln
            420                 425                 430 gta gac tcg tta gct gaa gta gtt ctc caa aat agg agg gga ctg gac          1344
Val Asp Ser Leu Ala Glu Val Val Leu Gln Asn Arg Arg Gly Leu Asp
        435                 440                 445 cta cta acg gca gaa caa gga gga att tgt tta gcc tta caa gaa aaa          1392
Leu Leu Thr Ala Glu Gln Gly Gly Ile Cys Leu Ala Leu Gln Glu Lys
    450                 455                 460 tgc tgt ttt tat gct aac aag tca gga att gtg aga aac aaa ata aga          1440
Cys Cys Phe Tyr Ala Asn Lys Ser Gly Ile Val Arg Asn Lys Ile Arg
465                 470                 475                 480 acc cta caa gaa gaa tta caa aaa cgc agg gaa agc ctg gca acc aac          1488
Thr Leu Gln Glu Glu Leu Gln Lys Arg Arg Glu Ser Leu Ala Thr Asn
                485                 490                 495 cct ctc tgg acc ggg ctg cag ggc ttt ctt ccg tac ctc cta cct ctc          1536
```

```
Pro Leu Trp Thr Gly Leu Gln Gly Phe Leu Pro Tyr Leu Leu Pro Leu
            500                 505                 510 ctg gga ccc cta ctc acc ctc cta ctc ata cta acc att ggg cca tgc    1584
Leu Gly Pro Leu Leu Thr Leu Leu Leu Ile Leu Thr Ile Gly Pro Cys
            515                 520                 525 gtt ttc aat cga tta gtt caa ttt gtt aaa gac agg atc tca gta gtc    1632
Val Phe Asn Arg Leu Val Gln Phe Val Lys Asp Arg Ile Ser Val Val
            530                 535                 540 cag gct tta gtc ctg act caa caa tac cac cag cta aaa cca cta gaa    1680
Gln Ala Leu Val Leu Thr Gln Gln Tyr His Gln Leu Lys Pro Leu Glu
545                 550                 555                 560 tac gag cca                                                         1689
Tyr Glu Pro <210> SEQ ID NO 2
<211> LENGTH: 563
<212> TYPE: PRT
<213> ORGANISM: Chimaera sp.

<400> SEQUENCE: 2

Met Lys Leu Pro Thr Gly Met Val Ile Leu Cys Ser Leu Ile Ile Val
1               5                   10                  15

Arg Ala Gly Phe Asp Asp Pro Arg Lys Ala Ile Ala Leu Val Gln Lys
                20                  25                  30

Gln His Gly Lys Pro Cys Glu Cys Ser Gly Gly Gln Val Ser Glu Ala
            35                  40                  45

Pro Pro Asn Ser Ile Gln Gln Val Thr Cys Pro Gly Lys Thr Ala Tyr
        50                  55                  60

Leu Met Thr Asn Gln Lys Trp Lys Cys Arg Val Thr Pro Lys Ile Ser
65                  70                  75                  80

Pro Ser Gly Gly Glu Leu Gln Asn Cys Pro Cys Asn Thr Phe Gln Asp
                85                  90                  95

Ser Met His Ser Ser Cys Tyr Thr Glu Tyr Arg Gln Cys Arg Arg Ile
            100                 105                 110

Asn Lys Thr Tyr Tyr Thr Ala Thr Leu Leu Lys Ile Arg Ser Gly Ser
        115                 120                 125

Leu Asn Glu Val Gln Ile Leu Gln Asn Pro Asn Gln Leu Leu Gln Ser
    130                 135                 140

Pro Cys Arg Gly Ser Ile Asn Gln Pro Val Cys Trp Ser Ala Thr Ala
145                 150                 155                 160

Pro Ile His Ile Ser Asp Gly Gly Pro Leu Asp Thr Lys Arg Val
                165                 170                 175

Trp Thr Val Gln Lys Arg Leu Glu Gln Ile His Lys Ala Met Thr Pro
            180                 185                 190

Glu Leu Gln Tyr His Pro Leu Ala Leu Pro Lys Val Arg Asp Asp Leu
        195                 200                 205

Ser Leu Asp Ala Arg Thr Phe Asp Ile Leu Asn Thr Thr Phe Arg Leu
    210                 215                 220

Leu Gln Met Ser Asn Phe Ser Leu Ala Gln Asp Cys Trp Leu Cys Leu
225                 230                 235                 240

Lys Leu Gly Thr Pro Thr Pro Leu Ala Ile Pro Thr Pro Ser Leu Thr
                245                 250                 255

Tyr Ser Leu Ala Asp Ser Leu Ala Asn Ala Ser Cys Gln Ile Ile Pro
            260                 265                 270

Pro Leu Leu Val Gln Pro Met Gln Phe Ser Asn Ser Ser Cys Leu Ser
        275                 280                 285
```

```
Ser Pro Phe Ile Asn Asp Thr Glu Gln Ile Asp Leu Gly Ala Val Thr
    290                 295                 300

Phe Thr Asn Cys Thr Ser Val Ala Asn Val Ser Ser Pro Leu Cys Ala
305                 310                 315                 320

Leu Asn Gly Ser Val Phe Leu Cys Gly Asn Asn Met Ala Tyr Thr Tyr
                325                 330                 335

Leu Pro Gln Asn Trp Thr Arg Leu Cys Val Gln Ala Ser Leu Leu Pro
            340                 345                 350

Asp Ile Asp Ile Asn Pro Gly Asp Glu Pro Val Pro Ile Pro Ala Ile
        355                 360                 365

Asp His Tyr Ile His Arg Pro Lys Arg Ala Val Gln Phe Ile Pro Leu
    370                 375                 380

Leu Ala Gly Leu Gly Ile Thr Ala Ala Phe Thr Thr Gly Ala Thr Gly
385                 390                 395                 400

Leu Gly Val Ser Val Thr Gln Tyr Thr Lys Leu Ser His Gln Leu Ile
                405                 410                 415

Ser Asp Val Gln Val Leu Ser Gly Thr Ile Gln Asp Leu Gln Asp Gln
            420                 425                 430

Val Asp Ser Leu Ala Glu Val Val Leu Gln Asn Arg Arg Gly Leu Asp
        435                 440                 445

Leu Leu Thr Ala Glu Gln Gly Gly Ile Cys Leu Ala Leu Gln Glu Lys
    450                 455                 460

Cys Cys Phe Tyr Ala Asn Lys Ser Gly Ile Val Arg Asn Lys Ile Arg
465                 470                 475                 480

Thr Leu Gln Glu Glu Leu Gln Lys Arg Arg Glu Ser Leu Ala Thr Asn
                485                 490                 495

Pro Leu Trp Thr Gly Leu Gln Gly Phe Leu Pro Tyr Leu Leu Pro Leu
            500                 505                 510

Leu Gly Pro Leu Leu Thr Leu Leu Leu Ile Leu Thr Ile Gly Pro Cys
        515                 520                 525

Val Phe Asn Arg Leu Val Gln Phe Val Lys Asp Arg Ile Ser Val Val
    530                 535                 540

Gln Ala Leu Val Leu Thr Gln Gln Tyr His Gln Leu Lys Pro Leu Glu
545                 550                 555                 560

Tyr Glu Pro

<210> SEQ ID NO 3
<211> LENGTH: 2058
<212> TYPE: DNA
<213> ORGANISM: Chimaera sp.
<220> FEATURE:
<221> NAME/KEY: CDS
<222> LOCATION: (1)..(2058)

<400> SEQUENCE: 3 atg gta ttg ctg cct ggg tcc atg ctt ctc acc tca aac ctg cac cac      48
Met Val Leu Leu Pro Gly Ser Met Leu Leu Thr Ser Asn Leu His His
 1               5                  10                  15 ctt cgg cac cag atg agt cct ggg agc tgg aaa aga ctg atc atc ctc      96
Leu Arg His Gln Met Ser Pro Gly Ser Trp Lys Arg Leu Ile Ile Leu
             20                  25                  30 tta agc tgc gta ttc ggc ggc ggc ggg acg agt ctg caa aat aag aac     144
Leu Ser Cys Val Phe Gly Gly Gly Gly Thr Ser Leu Gln Asn Lys Asn
         35                  40                  45 ccc cac cag ccc atg acc ctc act tgg cag gta ctg tcc caa act gga     192
Pro His Gln Pro Met Thr Leu Thr Trp Gln Val Leu Ser Gln Thr Gly
     50                  55                  60
```

```
gac gtt gtc tgg gat aca aag gca gtc cag ccc cct tgg act tgg tgg      240
Asp Val Val Trp Asp Thr Lys Ala Val Gln Pro Pro Trp Thr Trp Trp
 65                  70                  75                  80 ccc aca ctt aaa cct gat gta tgt gcc ttg gcg gct agt ctt gag tcc      288
Pro Thr Leu Lys Pro Asp Val Cys Ala Leu Ala Ala Ser Leu Glu Ser
                 85                  90                  95 tgg gat atc ccg gga acc gat gtc tcg tcc tct aaa cga gtc aga cct      336
Trp Asp Ile Pro Gly Thr Asp Val Ser Ser Ser Lys Arg Val Arg Pro
            100                 105                 110 ccg gac tca gac tat act gcc gct tat aag caa atc acc tgg gga gcc      384
Pro Asp Ser Asp Tyr Thr Ala Ala Tyr Lys Gln Ile Thr Trp Gly Ala
        115                 120                 125 ata ggg tgc agc tac cct cgg gct agg act aga atg gca agc tct acc      432
Ile Gly Cys Ser Tyr Pro Arg Ala Arg Thr Arg Met Ala Ser Ser Thr
130                 135                 140 ttc tac gta tgt ccc cgg gat ggc cgg acc ctt tca gaa gct aga agg      480
Phe Tyr Val Cys Pro Arg Asp Gly Arg Thr Leu Ser Glu Ala Arg Arg
145                 150                 155                 160 tgc ggg ggg cta gaa tcc cta tac tgt aaa gaa tgg gat tgt gag acc      528
Cys Gly Gly Leu Glu Ser Leu Tyr Cys Lys Glu Trp Asp Cys Glu Thr
                165                 170                 175 acg ggg acc ggt tat tgg cta tct aaa tcc tca aaa gac ctc ata act      576
Thr Gly Thr Gly Tyr Trp Leu Ser Lys Ser Ser Lys Asp Leu Ile Thr
            180                 185                 190 gta aaa tgg gac caa aat agc gaa tgg act caa aaa ttt caa cag tgt      624
Val Lys Trp Asp Gln Asn Ser Glu Trp Thr Gln Lys Phe Gln Gln Cys
        195                 200                 205 cac cag acc ggc tgg tgt aac ccc ctt aaa ata gat ttc aca gac aaa      672
His Gln Thr Gly Trp Cys Asn Pro Leu Lys Ile Asp Phe Thr Asp Lys
210                 215                 220 gga aaa tta tcc aag gac tgg ata acg gga aaa acc tgg gga tta aga      720
Gly Lys Leu Ser Lys Asp Trp Ile Thr Gly Lys Thr Trp Gly Leu Arg
225                 230                 235                 240 ttc tat gtg tct gga cat cca ggc gta cag ttc acc att cgc tta aaa      768
Phe Tyr Val Ser Gly His Pro Gly Val Gln Phe Thr Ile Arg Leu Lys
                245                 250                 255 atc acc aac atg cca gct gtg gca gta ggt cct gac ctc gtc ctt gtg      816
Ile Thr Asn Met Pro Ala Val Ala Val Gly Pro Asp Leu Val Leu Val
            260                 265                 270 gaa caa gga cct cct aga acg tcc ctc gct ctc cca cct cct ctt ccc      864
Glu Gln Gly Pro Pro Arg Thr Ser Leu Ala Leu Pro Pro Pro Leu Pro
        275                 280                 285 cca agg gaa gcg cca ccg cca tct ctc ccc gac tct aac tcc aca gcc      912
Pro Arg Glu Ala Pro Pro Pro Ser Leu Pro Asp Ser Asn Ser Thr Ala
290                 295                 300 ctg gcg act agt gca caa act ccc acg gtg aga aaa aca att gtt acc      960
Leu Ala Thr Ser Ala Gln Thr Pro Thr Val Arg Lys Thr Ile Val Thr
305                 310                 315                 320 cta aac act ccg cct ccc acc aca ggc gac aga ctt ttt gat ctt gtg     1008
Leu Asn Thr Pro Pro Pro Thr Thr Gly Asp Arg Leu Phe Asp Leu Val
                325                 330                 335 cag ggg gcc ttc cta acc tta aat gct acc aac cca ggg gcc act gag     1056
Gln Gly Ala Phe Leu Thr Leu Asn Ala Thr Asn Pro Gly Ala Thr Glu
            340                 345                 350 tct tgc tgg ctt tgt ttg gcc atg ggc ccc cct tat tat gaa gca ata     1104
Ser Cys Trp Leu Cys Leu Ala Met Gly Pro Pro Tyr Tyr Glu Ala Ile
        355                 360                 365 gcc tca tca gga gag gtc gcc tac tcc acc gac ctt gac cgg tgc cgc     1152
Ala Ser Ser Gly Glu Val Ala Tyr Ser Thr Asp Leu Asp Arg Cys Arg
370                 375                 380
```

```
tgg ggg acc caa gga aag ctc acc ctc act gag gtc tca gga cac ggg   1200
Trp Gly Thr Gln Gly Lys Leu Thr Leu Thr Glu Val Ser Gly His Gly
385                 390                 395                 400 ttg tgc ata gga aag gtg ccc ttt acc cat cag cat ctc tgc aat cag   1248
Leu Cys Ile Gly Lys Val Pro Phe Thr His Gln His Leu Cys Asn Gln
                405                 410                 415 acc cta tcc atc aat tcc tcc gga gac cat cag tat ctg ctc ccc tcc   1296
Thr Leu Ser Ile Asn Ser Ser Gly Asp His Gln Tyr Leu Leu Pro Ser
            420                 425                 430 aac cat agc tgg tgg gct tgc agc act ggc ctc acc cct tgc ctc tcc   1344
Asn His Ser Trp Trp Ala Cys Ser Thr Gly Leu Thr Pro Cys Leu Ser
        435                 440                 445 acc tca gtt ttt aat cag act aga gat ttc tgt atc cag gtc cag ctg   1392
Thr Ser Val Phe Asn Gln Thr Arg Asp Phe Cys Ile Gln Val Gln Leu
    450                 455                 460 att cct cgc atc tat tac tat cct gaa gaa gtt ttg tta cag gcc tat   1440
Ile Pro Arg Ile Tyr Tyr Tyr Pro Glu Glu Val Leu Leu Gln Ala Tyr
465                 470                 475                 480 gac aat tct cac ccc agg act aaa aga gag gct gtc tca ctt acc cta   1488
Asp Asn Ser His Pro Arg Thr Lys Arg Glu Ala Val Ser Leu Thr Leu
                485                 490                 495 gct gtt tta ctg ggg ttg gga atc acg gcg gga ata ggt act ggt tca   1536
Ala Val Leu Leu Gly Leu Gly Ile Thr Ala Gly Ile Gly Thr Gly Ser
            500                 505                 510 act gcc tta att aaa gga cct ata gac ctc cag caa gcc ctg aca agc   1584
Thr Ala Leu Ile Lys Gly Pro Ile Asp Leu Gln Gln Ala Leu Thr Ser
        515                 520                 525 ctc cag atc gcc ata gat gct gac ctc cgg gcc ctc caa gac tca gtc   1632
Leu Gln Ile Ala Ile Asp Ala Asp Leu Arg Ala Leu Gln Asp Ser Val
    530                 535                 540 agc aag tta gag gac tca ctg act tcc ctg tcc gag gta gtg ctc caa   1680
Ser Lys Leu Glu Asp Ser Leu Thr Ser Leu Ser Glu Val Val Leu Gln
545                 550                 555                 560 aat agg aga ggc ctt gac ttg ctg ttt cta aaa gaa ggt ggc ctc tgt   1728
Asn Arg Arg Gly Leu Asp Leu Leu Phe Leu Lys Glu Gly Gly Leu Cys
                565                 570                 575 gcg gcc cta aag gaa gag tgc tgt ttt tac ata gac cac tca ggt gca   1776
Ala Ala Leu Lys Glu Glu Cys Cys Phe Tyr Ile Asp His Ser Gly Ala
            580                 585                 590 gta cgg gac tcc atg aaa aaa ctc aaa gaa aaa ctg gat aaa aga cag   1824
Val Arg Asp Ser Met Lys Lys Leu Lys Glu Lys Leu Asp Lys Arg Gln
        595                 600                 605 tta gag cgc cag aaa agc caa aac tgg tat gaa gga tgg ttc aat aac   1872
Leu Glu Arg Gln Lys Ser Gln Asn Trp Tyr Glu Gly Trp Phe Asn Asn
    610                 615                 620 tcc cct tgg ttc act acc ctg cta tca acc atc gct ggg ccc cta tta   1920
Ser Pro Trp Phe Thr Thr Leu Leu Ser Thr Ile Ala Gly Pro Leu Leu
625                 630                 635                 640 ctc ctc ctt ctg ttg ctc atc ctc ggg cca tgc atc atc aat cga tta   1968
Leu Leu Leu Leu Leu Leu Ile Leu Gly Pro Cys Ile Ile Asn Arg Leu
                645                 650                 655 gtt caa ttt gtt aaa gac agg atc tca gta gtc cag gct tta gtc ctg   2016
Val Gln Phe Val Lys Asp Arg Ile Ser Val Val Gln Ala Leu Val Leu
            660                 665                 670 act caa caa tac cac cag cta aag cct ata gag tac gag cca           2058
Thr Gln Gln Tyr His Gln Leu Lys Pro Ile Glu Tyr Glu Pro
        675                 680                 685

<210> SEQ ID NO 4
<211> LENGTH: 686
<212> TYPE: PRT
```

<213> ORGANISM: Chimaera sp.

<400> SEQUENCE: 4

Met Val Leu Leu Pro Gly Ser Met Leu Leu Thr Ser Asn Leu His His
1               5                   10                  15

Leu Arg His Gln Met Ser Pro Gly Ser Trp Lys Arg Leu Ile Ile Leu
            20                  25                  30

Leu Ser Cys Val Phe Gly Gly Gly Thr Ser Leu Gln Asn Lys Asn
        35                  40                  45

Pro His Gln Pro Met Thr Leu Thr Trp Gln Val Leu Ser Gln Thr Gly
        50                  55                  60

Asp Val Val Trp Asp Thr Lys Ala Val Gln Pro Trp Thr Trp Trp
65                  70                  75                  80

Pro Thr Leu Lys Pro Asp Val Cys Ala Leu Ala Ser Leu Glu Ser
                85                  90                  95

Trp Asp Ile Pro Gly Thr Asp Val Ser Ser Lys Arg Val Arg Pro
            100                 105                 110

Pro Asp Ser Asp Tyr Thr Ala Ala Tyr Lys Gln Ile Thr Trp Gly Ala
        115                 120                 125

Ile Gly Cys Ser Tyr Pro Arg Ala Arg Thr Arg Met Ala Ser Ser Thr
        130                 135                 140

Phe Tyr Val Cys Pro Arg Asp Gly Arg Thr Leu Ser Glu Ala Arg Arg
145                 150                 155                 160

Cys Gly Gly Leu Glu Ser Leu Tyr Cys Lys Glu Trp Asp Cys Glu Thr
                165                 170                 175

Thr Gly Thr Gly Tyr Trp Leu Ser Lys Ser Ser Lys Asp Leu Ile Thr
            180                 185                 190

Val Lys Trp Asp Gln Asn Ser Glu Trp Thr Gln Lys Phe Gln Gln Cys
        195                 200                 205

His Gln Thr Gly Trp Cys Asn Pro Leu Lys Ile Asp Phe Thr Asp Lys
        210                 215                 220

Gly Lys Leu Ser Lys Asp Trp Ile Thr Gly Lys Thr Trp Gly Leu Arg
225                 230                 235                 240

Phe Tyr Val Ser Gly His Pro Gly Val Gln Phe Thr Ile Arg Leu Lys
                245                 250                 255

Ile Thr Asn Met Pro Ala Val Ala Val Gly Pro Asp Leu Val Leu Val
            260                 265                 270

Glu Gln Gly Pro Pro Arg Thr Ser Leu Ala Leu Pro Pro Leu Pro
        275                 280                 285

Pro Arg Glu Ala Pro Pro Ser Leu Pro Asp Ser Asn Ser Thr Ala
290                 295                 300

Leu Ala Thr Ser Ala Gln Thr Pro Thr Val Arg Lys Thr Ile Val Thr
305                 310                 315                 320

Leu Asn Thr Pro Pro Thr Thr Gly Asp Arg Leu Phe Asp Leu Val
                325                 330                 335

Gln Gly Ala Phe Leu Thr Leu Asn Ala Thr Asn Pro Gly Ala Thr Glu
            340                 345                 350

Ser Cys Trp Leu Cys Leu Ala Met Gly Pro Pro Tyr Tyr Glu Ala Ile
        355                 360                 365

Ala Ser Ser Gly Glu Val Ala Tyr Ser Thr Asp Leu Asp Arg Cys Arg
        370                 375                 380

Trp Gly Thr Gln Gly Lys Leu Thr Leu Thr Glu Val Ser Gly His Gly
385                 390                 395                 400

Leu Cys Ile Gly Lys Val Pro Phe Thr His Gln His Leu Cys Asn Gln

```
                    405                 410                 415
Thr Leu Ser Ile Asn Ser Ser Gly Asp His Gln Tyr Leu Leu Pro Ser
            420                 425                 430

Asn His Ser Trp Trp Ala Cys Ser Thr Gly Leu Thr Pro Cys Leu Ser
        435                 440                 445

Thr Ser Val Phe Asn Gln Thr Arg Asp Phe Cys Ile Gln Val Gln Leu
    450                 455                 460

Ile Pro Arg Ile Tyr Tyr Tyr Pro Glu Glu Val Leu Leu Gln Ala Tyr
465                 470                 475                 480

Asp Asn Ser His Pro Arg Thr Lys Arg Glu Ala Val Ser Leu Thr Leu
                485                 490                 495

Ala Val Leu Leu Gly Leu Gly Ile Thr Ala Gly Ile Gly Thr Gly Ser
            500                 505                 510

Thr Ala Leu Ile Lys Gly Pro Ile Asp Leu Gln Gln Gly Leu Thr Ser
        515                 520                 525

Leu Gln Ile Ala Ile Asp Ala Asp Leu Arg Ala Leu Gln Asp Ser Val
    530                 535                 540

Ser Lys Leu Glu Asp Ser Leu Thr Ser Leu Ser Glu Val Val Leu Gln
545                 550                 555                 560

Asn Arg Arg Gly Leu Asp Leu Leu Phe Leu Lys Glu Gly Gly Leu Cys
                565                 570                 575

Ala Ala Leu Lys Glu Glu Cys Cys Phe Tyr Ile Asp His Ser Gly Ala
            580                 585                 590

Val Arg Asp Ser Met Lys Lys Leu Lys Glu Lys Leu Asp Lys Arg Gln
        595                 600                 605

Leu Glu Arg Gln Lys Ser Gln Asn Trp Tyr Glu Gly Trp Phe Asn Asn
    610                 615                 620

Ser Pro Trp Phe Thr Thr Leu Leu Ser Thr Ile Ala Gly Pro Leu Leu
625                 630                 635                 640

Leu Leu Leu Leu Leu Leu Ile Leu Gly Pro Cys Ile Ile Asn Arg Leu
                645                 650                 655

Val Gln Phe Val Lys Asp Arg Ile Ser Val Val Gln Ala Leu Val Leu
            660                 665                 670

Thr Gln Gln Tyr His Gln Leu Lys Pro Ile Glu Tyr Glu Pro
        675                 680                 685

<210> SEQ ID NO 5
<211> LENGTH: 5
<212> TYPE: PRT
<213> ORGANISM: MLV-related retrovirus

<400> SEQUENCE: 5

Ala Glu Ser Pro His
 1               5

<210> SEQ ID NO 6
<211> LENGTH: 71
<212> TYPE: PRT
<213> ORGANISM: MLV-related retrovirus

<400> SEQUENCE: 6

Gly Trp Phe Glu Gly Leu Phe Asn Arg Ser Pro Trp Phe Thr Thr Leu
 1               5                  10                  15

Ile Ser Thr Ile Met Gly Pro Leu Ile Val Leu Leu Ile Leu Leu Leu
                20                  25                  30

Phe Gly Pro Cys Ile Leu Asn Arg Leu Val Gln Phe Val Lys Asp Arg
            35                  40                  45
```

-continued

Ile Ser Val Val Gln Ala Leu Val Leu Thr Gln Gln Tyr His Gln Leu
        50                  55                  60

Lys Pro Ile Glu Tyr Glu Pro
 65                  70

<210> SEQ ID NO 7
<211> LENGTH: 5
<212> TYPE: PRT
<213> ORGANISM: RD114 retrovirus

<400> SEQUENCE: 7

Ala Gly Phe Asp Asp
 1               5

<210> SEQ ID NO 8
<211> LENGTH: 67
<212> TYPE: PRT
<213> ORGANISM: RD114 retrovirus

<400> SEQUENCE: 8

Leu Trp Thr Gly Leu Gln Gly Phe Leu Pro Tyr Leu Leu Pro Leu Leu
 1               5                  10                  15

Gly Pro Leu Leu Thr Leu Leu Leu Ile Leu Thr Ile Gly Pro Cys Val
                20                  25                  30

Phe Ser Arg Leu Met Ala Phe Ile Asn Asp Arg Leu Asn Val Val His
            35                  40                  45

Ala Met Val Leu Ala Gln Gln Tyr Gln Ala Leu Lys Ala Glu Glu Glu
        50                  55                  60

Ala Gln Asp
 65

<210> SEQ ID NO 9
<211> LENGTH: 66
<212> TYPE: PRT
<213> ORGANISM: Artificial
<220> FEATURE:
<223> OTHER INFORMATION: chimaera sp.

<400> SEQUENCE: 9

Leu Trp Thr Gly Leu Gln Gly Phe Leu Pro Tyr Leu Leu Pro Leu Leu
 1               5                  10                  15

Gly Pro Leu Leu Thr Leu Leu Leu Ile Leu Thr Ile Gly Pro Cys Val
                20                  25                  30

Phe Asn Arg Leu Val Gln Phe Val Lys Asp Arg Ile Ser Val Val Gln
            35                  40                  45

Ala Leu Val Leu Thr Gln Gln Tyr His Gln Leu Lys Pro Ile Glu Tyr
        50                  55                  60

Glu Pro
 65

<210> SEQ ID NO 10
<211> LENGTH: 196
<212> TYPE: PRT
<213> ORGANISM: MLV-related retrovirus

<400> SEQUENCE: 10

Glu Pro Val Ser Leu Thr Leu Ala Leu Leu Leu Gly Gly Leu Thr Met
 1               5                  10                  15

Gly Gly Ile Ala Ala Gly Ile Gly Thr Gly Thr Thr Ala Leu Thr Lys
                20                  25                  30

```
Thr Gln Gln Phe Glu Gln Leu His Ala Ala Leu Gln Thr Asp Leu Asn
            35                  40                  45

Glu Val Glu Lys Ser Ile Thr Asn Leu Glu Lys Ser Leu Thr Ser Leu
 50                  55                  60

Ser Glu Val Val Leu Gln Asn Arg Arg Gly Leu Asp Leu Leu Phe Leu
 65                  70                  75                  80

Lys Glu Gly Gly Leu Cys Ala Ala Leu Lys Glu Glu Cys Cys Phe Tyr
                 85                  90                  95

Ala Asp His Thr Gly Leu Val Arg Asp Ser Met Ala Lys Leu Arg Glu
             100                 105                 110

Arg Leu Asn Gln Arg Gln Lys Leu Phe Glu Thr Gly Gln Gly Trp Phe
         115                 120                 125

Glu Gly Leu Phe Asn Arg Ser Pro Trp Phe Thr Thr Leu Ile Ser Thr
130                 135                 140

Ile Met Gly Pro Leu Ile Val Leu Leu Leu Ile Leu Leu Phe Gly Pro
145                 150                 155                 160

Cys Ile Leu Asn Arg Leu Val Gln Phe Val Lys Asp Arg Ile Ser Val
                 165                 170                 175

Val Gln Ala Leu Val Leu Thr Gln Gln Tyr His Gln Leu Lys Pro Ile
180                 185                 190

Glu Tyr Glu Pro
        195

<210> SEQ ID NO 11
<211> LENGTH: 187
<212> TYPE: PRT
<213> ORGANISM: RD114 retrovirus

<400> SEQUENCE: 11

Ala Val Gln Phe Ile Pro Leu Leu Ala Gly Leu Gly Ile Thr Ala Ala
 1               5                  10                  15

Phe Thr Thr Gly Ala Thr Gly Leu Gly Val Ser Val Thr Gln Tyr Thr
            20                  25                  30

Lys Leu Ser His Gln Leu Ile Ser Asp Val Gln Val Leu Ser Gly Thr
         35                  40                  45

Ile Gln Asp Leu Gln Asp Gln Val Asp Ser Leu Ala Glu Val Val Leu
 50                  55                  60

Gln Asn Arg Arg Gly Leu Asp Leu Leu Thr Ala Glu Gln Gly Gly Ile
 65                  70                  75                  80

Cys Leu Ala Leu Gln Glu Lys Cys Cys Phe Tyr Ala Asn Lys Ser Gly
                 85                  90                  95

Ile Val Arg Asn Lys Ile Arg Thr Leu Gln Glu Glu Leu Gln Lys Arg
             100                 105                 110

Arg Glu Ser Leu Ala Ser Asn Pro Leu Trp Thr Gly Leu Gln Gly Phe
         115                 120                 125

Leu Pro Tyr Leu Leu Pro Leu Leu Gly Pro Leu Leu Thr Leu Leu Leu
130                 135                 140

Ile Leu Thr Ile Gly Pro Cys Val Phe Ser Arg Leu Met Ala Phe Ile
145                 150                 155                 160

Asn Asp Arg Leu Asn Val Val His Ala Met Val Leu Ala Gln Gln Tyr
                 165                 170                 175

Gln Ala Leu Lys Ala Glu Glu Ala Gln Asp
             180                 185

<210> SEQ ID NO 12
<211> LENGTH: 191
```

```
<212> TYPE: PRT
<213> ORGANISM: Mason-Pfizer monkey virus

<400> SEQUENCE: 12

Ala Ile Gln Leu Ile Pro Leu Phe Val Gly Leu Gly Ile Thr Thr Ala
  1               5                  10                  15

Val Ser Thr Gly Ala Ala Gly Leu Gly Val Ser Ile Thr Gln Tyr Thr
             20                  25                  30

Lys Leu Ser His Gln Leu Ile Ser Asp Val Gln Ala Ile Ser Ser Thr
         35                  40                  45

Ile Gln Asp Leu Gln Asp Gln Val Asp Ser Leu Ala Glu Val Val Leu
     50                  55                  60

Gln Asn Arg Arg Gly Leu Asp Leu Leu Thr Ala Glu Gln Gly Gly Ile
 65                  70                  75                  80

Cys Leu Ala Leu Gln Glu Lys Cys Cys Phe Tyr Ala Asn Lys Ser Gly
                 85                  90                  95

Ile Val Arg Asp Lys Ile Lys Asn Leu Gln Asp Leu Glu Arg Arg
             100                 105                 110

Arg Arg Gln Leu Ile Asp Asn Pro Phe Trp Thr Ser Phe His Gly Phe
             115                 120                 125

Leu Pro Tyr Val Met Pro Leu Leu Gly Pro Leu Leu Cys Leu Leu Leu
    130                 135                 140

Val Leu Ser Phe Gly Pro Ile Ile Phe Asn Lys Leu Met Thr Phe Ile
145                 150                 155                 160

Lys His Gln Ile Glu Ser Ile Gln Ala Lys Pro Ile Gln Val His Tyr
                165                 170                 175

His Arg Leu Glu Gln Asp Ser Gly Gly Ser Tyr Leu Thr Leu Thr
            180                 185                 190

<210> SEQ ID NO 13
<211> LENGTH: 98
<212> TYPE: PRT
<213> ORGANISM: RD114 retrovirus

<400> SEQUENCE: 13

Phe Tyr Ala Asn Lys Ser Gly Ile Val Arg Asn Lys Ile Arg Thr Leu
  1               5                  10                  15

Gln Glu Glu Leu Gln Lys Arg Arg Glu Ser Leu Ala Ser Asn Pro Leu
             20                  25                  30

Trp Thr Gly Leu Gln Gly Phe Leu Pro Tyr Leu Leu Pro Leu Leu Gly
         35                  40                  45

Pro Leu Leu Thr Leu Leu Leu Ile Leu Thr Ile Gly Pro Cys Val Phe
     50                  55                  60

Ser Arg Leu Met Ala Phe Ile Asn Asp Arg Leu Asn Val Val His Ala
 65                  70                  75                  80

Met Val Leu Ala Gln Gln Tyr Gln Ala Leu Lys Ala Glu Glu Glu Ala
                 85                  90                  95

Gln Asp

<210> SEQ ID NO 14
<211> LENGTH: 97
<212> TYPE: PRT
<213> ORGANISM: Artificial
<220> FEATURE:
<223> OTHER INFORMATION: chimaera sp.

<400> SEQUENCE: 14

Phe Tyr Ala Asn Lys Ser Gly Ile Val Arg Asn Lys Ile Arg Thr Leu
```

```
                1               5                  10                 15
Gln Glu Glu Leu Gln Lys Arg Arg Glu Ser Leu Ala Ser Asn Pro Leu
                20                  25                 30

Trp Thr Gly Leu Gln Gly Phe Leu Pro Tyr Leu Leu Pro Leu Leu Gly
            35                  40                 45

Pro Leu Leu Thr Leu Leu Ile Leu Thr Ile Gly Pro Cys Val Phe
        50                  55                 60

Asn Arg Leu Val Gln Phe Val Lys Asp Arg Ile Ser Val Val Gln Ala
 65                  70                  75                  80

Leu Val Leu Thr Gln Gln Tyr His Gln Leu Lys Pro Ile Glu Tyr Glu
                85                  90                 95

Pro
```

<210> SEQ ID NO 15
<211> LENGTH: 97
<212> TYPE: PRT
<213> ORGANISM: Artificial
<220> FEATURE:
<223> OTHER INFORMATION: chimaera sp.

<400> SEQUENCE: 15

```
Phe Tyr Ala Asn Lys Ser Gly Ile Val Arg Asn Lys Ile Arg Thr Leu
 1               5                  10                 15

Gln Glu Glu Leu Gln Lys Arg Arg Glu Ser Leu Ala Ser Asn Pro Leu
                20                  25                 30

Trp Thr Gly Leu Gln Gly Phe Leu Pro Tyr Leu Leu Pro Leu Leu Gly
            35                  40                 45

Pro Leu Ile Val Leu Leu Ile Leu Phe Gly Pro Cys Ile Leu
        50                  55                 60

Asn Arg Leu Val Gln Phe Val Lys Asp Arg Ile Ser Val Val Gln Ala
 65                  70                  75                  80

Leu Val Leu Thr Gln Gln Tyr His Gln Leu Lys Pro Ile Glu Tyr Glu
                85                  90                 95

Pro
```

<210> SEQ ID NO 16
<211> LENGTH: 101
<212> TYPE: PRT
<213> ORGANISM: Artificial
<220> FEATURE:
<223> OTHER INFORMATION: chimaera sp.

<400> SEQUENCE: 16

```
Phe Tyr Ala Asn Lys Ser Gly Ile Val Arg Asn Lys Ile Arg Thr Leu
 1               5                  10                 15

Gln Glu Glu Leu Gln Lys Arg Arg Glu Ser Leu Ala Ser Asn Pro Leu
                20                  25                 30

Trp Thr Gly Leu Gln Gly Phe Leu Pro Trp Phe Thr Thr Leu Ile Ser
            35                  40                 45

Thr Ile Met Gly Pro Leu Ile Val Leu Leu Ile Leu Phe Gly
        50                  55                 60

Pro Cys Ile Leu Asn Arg Leu Val Gln Phe Val Lys Asp Arg Ile Ser
 65                  70                  75                  80

Val Val Gln Ala Leu Val Leu Thr Gln Gln Tyr His Gln Leu Lys Pro
                85                  90                 95

Ile Glu Tyr Glu Pro
                100
```

```
<210> SEQ ID NO 17
<211> LENGTH: 81
<212> TYPE: PRT
<213> ORGANISM: Artificial
<220> FEATURE:
<223> OTHER INFORMATION: chimaera sp.

<400> SEQUENCE: 17

Phe Tyr Ala Asn Lys Ser Gly Ile Val Arg Asn Lys Ile Arg Thr Leu
 1               5                  10                  15

Gln Glu Glu Leu Gln Lys Arg Arg Glu Ser Leu Ala Ser Asn Pro Leu
             20                  25                  30

Trp Thr Gly Leu Gln Gly Phe Leu Pro Tyr Leu Leu Pro Leu Leu Gly
         35                  40                  45

Pro Leu Leu Thr Leu Leu Leu Ile Leu Thr Ile Gly Pro Cys Val Phe
     50                  55                  60

Ser Arg Leu Met Ala Phe Ile Asn Asp Arg Leu Asn Val Val His Ala
 65                  70                  75                  80

Met

<210> SEQ ID NO 18
<211> LENGTH: 98
<212> TYPE: PRT
<213> ORGANISM: Artificial
<220> FEATURE:
<223> OTHER INFORMATION: chimaera sp.

<400> SEQUENCE: 18

Phe Tyr Ala Asn Lys Ser Gly Ile Val Arg Asn Lys Ile Arg Thr Leu
 1               5                  10                  15

Gln Glu Glu Leu Gln Lys Arg Arg Glu Ser Leu Ala Ser Asn Pro Leu
             20                  25                  30

Trp Thr Gly Leu Gln Gly Phe Leu Pro Tyr Leu Leu Pro Leu Leu Gly
         35                  40                  45

Pro Leu Leu Thr Leu Leu Leu Ile Leu Thr Ile Gly Pro Cys Val Phe
     50                  55                  60

Ser Arg Leu Met Ala Phe Ile Asn Asp Arg Leu Asn Val Val Gln Ala
 65                  70                  75                  80

Leu Val Leu Thr Gln Gln Tyr Gln Ala Leu Lys Ala Glu Glu Glu Ala
                 85                  90                  95

Gln Asp

<210> SEQ ID NO 19
<211> LENGTH: 98
<212> TYPE: PRT
<213> ORGANISM: Artificial
<220> FEATURE:
<223> OTHER INFORMATION: chimaera sp.

<400> SEQUENCE: 19

Phe Tyr Ala Asn Lys Ser Gly Ile Val Arg Asn Lys Ile Arg Thr Leu
 1               5                  10                  15

Gln Glu Glu Leu Gln Lys Arg Arg Glu Ser Leu Ala Ser Asn Pro Leu
             20                  25                  30

Trp Thr Gly Leu Gln Gly Phe Leu Pro Tyr Leu Leu Pro Leu Leu Gly
         35                  40                  45

Pro Leu Leu Thr Leu Leu Leu Ile Leu Thr Ile Gly Pro Cys Val Phe
     50                  55                  60

Ser Arg Leu Met Ala Phe Ile Asn Asp Arg Leu Asn Val Ala Arg Leu
```

```
                65                  70                  75                  80
Met Ala Glu Ala Leu Gln Tyr Gln Ala Leu Lys Ala Glu Glu Glu Ala
                    85                  90                  95

Gln Asp

<210> SEQ ID NO 20
<211> LENGTH: 98
<212> TYPE: PRT
<213> ORGANISM: Artificial
<220> FEATURE:
<223> OTHER INFORMATION: chimaera sp.

<400> SEQUENCE: 20

Phe Tyr Ala Asn Lys Ser Gly Ile Val Arg Asn Lys Ile Arg Thr Leu
  1               5                  10                  15

Gln Glu Glu Leu Gln Lys Arg Arg Glu Ser Leu Ala Ser Asn Pro Leu
                20                  25                  30

Trp Thr Gly Leu Gln Gly Phe Leu Pro Tyr Leu Leu Pro Leu Leu Gly
            35                  40                  45

Pro Leu Leu Thr Leu Leu Leu Ile Leu Thr Ile Gly Pro Cys Val Phe
        50                  55                  60

Ser Arg Leu Met Ala Phe Ile Asn Asp Arg Leu Asn Val Arg Gln Ala
 65                 70                  75                  80

Gly Phe Leu Gly Leu Gln Tyr Gln Ala Leu Lys Ala Glu Glu Glu Ala
                85                  90                  95

Gln Asp

<210> SEQ ID NO 21
<211> LENGTH: 98
<212> TYPE: PRT
<213> ORGANISM: Artificial
<220> FEATURE:
<223> OTHER INFORMATION: chimaera sp.

<400> SEQUENCE: 21

Phe Tyr Ala Asn Lys Ser Gly Ile Val Arg Asn Lys Ile Arg Thr Leu
  1               5                  10                  15

Gln Glu Glu Leu Gln Lys Arg Arg Glu Ser Leu Ala Ser Asn Pro Leu
                20                  25                  30

Trp Thr Gly Leu Gln Gly Phe Leu Pro Tyr Leu Leu Pro Leu Leu Gly
            35                  40                  45

Pro Leu Leu Thr Leu Leu Leu Ile Leu Thr Ile Gly Pro Cys Val Phe
        50                  55                  60

Ser Arg Leu Met Ala Phe Ile Asn Asp Arg Leu Asn Val Ser Gln Asn
 65                 70                  75                  80

Tyr Pro Ile Val Gln Gln Tyr Gln Ala Leu Lys Ala Glu Glu Glu Ala
                85                  90                  95

Gln Asp

<210> SEQ ID NO 22
<211> LENGTH: 98
<212> TYPE: PRT
<213> ORGANISM: Artificial
<220> FEATURE:
<223> OTHER INFORMATION: chimaera sp.

<400> SEQUENCE: 22

Phe Tyr Ala Asn Lys Ser Gly Ile Val Arg Asn Lys Ile Arg Thr Leu
  1               5                  10                  15
```

-continued

```
Gln Glu Glu Leu Gln Lys Arg Arg Glu Ser Leu Ala Ser Asn Pro Leu
             20                  25                  30

Trp Thr Gly Leu Gln Gly Phe Leu Pro Tyr Leu Leu Pro Leu Leu Gly
         35                  40                  45

Pro Leu Leu Thr Leu Leu Leu Ile Leu Thr Ile Gly Pro Cys Val Phe
     50                  55                  60

Ser Arg Leu Met Ala Phe Ile Asn Asp Arg Leu Asn Val Val His Ala
 65                  70                  75                  80

Met Val Leu Ala Gln Gln Ala Gln Ala Leu Lys Ala Glu Glu Glu Ala
                 85                  90                  95

Gln Asp

<210> SEQ ID NO 23
<211> LENGTH: 68
<212> TYPE: PRT
<213> ORGANISM: Chimaera sp.

<400> SEQUENCE: 23

Ala Glu Ser Pro His Gly Trp Phe Glu Gly Leu Phe Met Arg Ser Pro
  1               5                  10                  15

Trp Phe Thr Thr Leu Ile Ser Thr Ile Met Gly Pro Leu Ile Phe Gly
             20                  25                  30

Pro Cys Ile Leu Met Arg Leu Val Gln Phe Val Lys Asp Ile Ser Val
         35                  40                  45

Val Gln Ala Leu Val Leu Thr Gln Gln Tyr His Gln Leu Lys Pro Ile
     50                  55                  60

Glu Tyr Glu Pro
 65

<210> SEQ ID NO 24
<211> LENGTH: 70
<212> TYPE: PRT
<213> ORGANISM: Chimaera sp.

<400> SEQUENCE: 24

Ala Gly Phe Asp Asp Leu Trp Thr Gly Leu Gln Gly Phe Leu Pro Tyr
  1               5                  10                  15

Leu Leu Pro Leu Leu Gly Pro Leu Leu Thr Leu Ile Leu Thr Ile Gly
             20                  25                  30

Pro Cys Val Phe Ser Arg Leu Met Ala Phe Ile Asn Asp Arg Leu Asn
         35                  40                  45

Val Val His Ala Met Val Leu Ala Gln Gln Tyr Gln Ala Leu Lys Ala
     50                  55                  60

Glu Glu Glu Ala Gln Asp
 65                  70

<210> SEQ ID NO 25
<211> LENGTH: 68
<212> TYPE: PRT
<213> ORGANISM: Chimaera sp.

<400> SEQUENCE: 25

Ala Gly Phe Asp Asp Leu Trp Thr Gly Leu Gln Gly Phe Leu Pro Tyr
  1               5                  10                  15

Leu Leu Pro Leu Leu Gly Pro Leu Leu Thr Leu Ile Leu Thr Ile Gly
             20                  25                  30

Pro Cys Val Phe Met Arg Leu Val Gln Phe Val Lys Asp Ile Ser Val
         35                  40                  45
```

```
Val Gln Ala Leu Val Leu Thr Gln Gln Tyr His Gln Leu Lys Pro Ile
    50                  55                  60

Glu Tyr Glu Pro
 65

<210> SEQ ID NO 26
<211> LENGTH: 4
<212> TYPE: PRT
<213> ORGANISM: Chimaera sp.
<220> FEATURE:
<221> NAME/KEY: misc_feature
<222> LOCATION: (2)..(3)
<223> OTHER INFORMATION: Xaa can be any naturally occurring amino acid

<400> SEQUENCE: 26

Tyr Xaa Xaa Leu
 1

<210> SEQ ID NO 27
<211> LENGTH: 8
<212> TYPE: PRT
<213> ORGANISM: Chimaera sp.

<400> SEQUENCE: 27

Val His Ala Met Val Leu Ala Gln
 1               5

<210> SEQ ID NO 28
<211> LENGTH: 52
<212> TYPE: PRT
<213> ORGANISM: Chimaera sp.

<400> SEQUENCE: 28

Glu Pro Val Ser Leu Thr Leu Ala Leu Gly Thr Met Gly Gly Ile Leu
 1               5                  10                  15

Lys Thr Gln Gln Phe Glu Gln His Ala Ala Thr Gln Thr Leu Asn Glu
            20                  25                  30

Val Glu Lys Ser Thr Asn Glu Lys Ser Leu Thr Ser Phe Leu Lys Glu
        35                  40                  45

Leu Ala Lys Glu
    50

<210> SEQ ID NO 29
<211> LENGTH: 89
<212> TYPE: PRT
<213> ORGANISM: Chimaera sp.

<400> SEQUENCE: 29

Ala Thr Gln Phe Ile Pro Leu Leu Ala Gly Leu Gly Leu Thr Ala Ala
 1               5                  10                  15

Phe Thr Thr Gly Ala Thr Gly Leu Gly Val Ser Val Thr Gln Tyr Thr
            20                  25                  30

Lys Leu Ser His Gln Leu Ile Ser Asp Val Gln Val Leu Ser Gly Thr
        35                  40                  45

Ile Gln Asp Leu Gln Asp Gln Val Asp Ser Leu Ala Glu Val Val Leu
    50                  55                  60

Gln Asn Arg Arg Gly Leu Asp Leu Leu Thr Ala Glu Gln Gly Gly Ile
 65                  70                  75                  80

Cys Leu Ala Leu Gln Glu Lys Cys Cys
                 85

<210> SEQ ID NO 30
```

```
<211> LENGTH: 12
<212> TYPE: PRT
<213> ORGANISM: Chimaera sp.

<400> SEQUENCE: 30

Ile Leu Phe Val Thr Val Ser Ala Ile Ala Thr Ser
1               5                   10

<210> SEQ ID NO 31
<211> LENGTH: 60
<212> TYPE: PRT
<213> ORGANISM: Chimaera sp.

<400> SEQUENCE: 31

Asp His Thr Leu Asp Ser Met Ala Lys Arg Arg Asn Gln Gln Lys Leu
1               5                   10                  15

Phe Glu Thr Gly Gln Gly Phe Glu Phe Asn Arg Ser Trp Phe Thr Thr
            20                  25                  30

Ile Ser Thr Ile Met Ile Val Leu Phe Ile Leu Asn Val Gln Val Lys
        35                  40                  45

Leu Ser Gln Leu Thr His Gln Pro Ile Tyr Glu Pro
    50                  55                  60

<210> SEQ ID NO 32
<211> LENGTH: 97
<212> TYPE: PRT
<213> ORGANISM: Chimaera sp.

<400> SEQUENCE: 32

Phe Tyr Ala Asn Lys Ser Gly Ile Val Arg Asn Lys Ile Phe Thr Leu
1               5                   10                  15

Gln Glu Glu Leu Gln Lys Arg Arg Glu Ser Leu Ala Ser Asn Pro Leu
            20                  25                  30

Trp Thr Gly Leu Gln Gly Phe Leu Pro Tyr Leu Leu Pro Leu Leu Gly
        35                  40                  45

Pro Leu Leu Thr Leu Leu Leu Ile Leu Thr Ile Gly Pro Cys Val Phe
    50                  55                  60

Ser Arg Leu Met Ala Phe Ile Asn Asp Arg Leu Asn Val Val His Ala
65                  70                  75                  80

Met Leu Ala Gln Gln Tyr Gln Ala Leu Lys Ala Glu Glu Glu Ala Gln
                85                  90                  95

Asp

<210> SEQ ID NO 33
<211> LENGTH: 54
<212> TYPE: PRT
<213> ORGANISM: Chimaera sp.

<400> SEQUENCE: 33

Asp Lys Asn Asp Asp Glu Phe Arg Gln Ile Asp Phe Ser Phe His Val
1               5                   10                  15

Met Cys Val Ser Phe Ile Leu Asn Lys Thr Lys His Gln Ile Glu Ser
            20                  25                  30

Ile Gln Lys Pro Ile Gln Val His His Arg Glu Gln Asp Ser Gly Gly
        35                  40                  45

Ser Tyr Leu Thr Leu Thr
    50

<210> SEQ ID NO 34
<211> LENGTH: 98
```

```
<212> TYPE: PRT
<213> ORGANISM: Chimaera sp.

<400> SEQUENCE: 34

Phe Tyr Ala Asn Lys Ser Gly Ile Val Arg Asn Lys Ile Arg Thr Leu
  1               5                  10                  15

Gln Glu Glu Leu Gln Lys Arg Arg Glu Ser Leu Ala Ser Asn Pro Leu
             20                  25                  30

Trp Thr Gly Leu Gln Gly Phe Leu Pro Tyr Leu Leu Pro Leu Leu Gly
         35                  40                  45

Pro Leu Leu Thr Leu Leu Leu Ile Leu Thr Ile Gly Pro Cys Val Phe
     50                  55                  60

Ser Arg Leu Met Ala Phe Ile Asn Asp Arg Leu Asn Val Val His Ala
 65                  70                  75                  80

Met Val Leu Ala Gln Gln Tyr Gln Ala Leu Lys Ala Glu Glu Glu Ala
                 85                  90                  95

Gln Asp

<210> SEQ ID NO 35
<211> LENGTH: 97
<212> TYPE: PRT
<213> ORGANISM: Chimaera sp.

<400> SEQUENCE: 35

Phe Tyr Ala Asn Lys Ser Gly Ile Val Arg Asn Lys Ile Arg Thr Leu
  1               5                  10                  15

Gln Glu Glu Leu Gln Lys Arg Arg Glu Ser Leu Ala Ser Asn Pro Leu
             20                  25                  30

Trp Thr Gly Leu Gln Gly Phe Leu Pro Tyr Leu Leu Pro Leu Leu Gly
         35                  40                  45

Pro Leu Leu Thr Leu Leu Leu Ile Leu Thr Ile Gly Pro Cys Val Phe
     50                  55                  60

Asn Arg Leu Val Gln Phe Val Lys Asp Arg Ile Ser Val Val Gln Ala
 65                  70                  75                  80

Leu Val Leu Thr Gln Gln Tyr Asx Gln Leu Lys Pro Ile Glu Tyr Glu
                 85                  90                  95

Arg

<210> SEQ ID NO 36
<211> LENGTH: 97
<212> TYPE: PRT
<213> ORGANISM: Chimaera sp.

<400> SEQUENCE: 36

Phe Tyr Ala Asn Lys Ser Gly Ile Val Arg Asn Lys Ile Arg Thr Leu
  1               5                  10                  15

Gln Glu Glu Leu Gln Lys Arg Arg Glu Ser Leu Ala Ser Asn Pro Leu
             20                  25                  30

Trp Thr Gly Leu Gln Gly Phe Leu Pro Tyr Leu Leu Pro Leu Leu Gly
         35                  40                  45

Pro Leu Ile Val Leu Leu Ile Leu Phe Gly Pro Cys Ile Leu
     50                  55                  60

Asn Arg Leu Val Gln Phe Val Lys Asp Arg Ile Ser Val Val Gln Ala
 65                  70                  75                  80

Leu Val Leu Thr Gln Gln Tyr Asx Gln Leu Lys Pro Ile Glu Tyr Glu
                 85                  90                  95

Pro
```

<210> SEQ ID NO 37
<211> LENGTH: 102
<212> TYPE: PRT
<213> ORGANISM: Chimaera sp.

<400> SEQUENCE: 37

Phe Tyr Ala Asn Lys Ser Gly Ile Val Arg Asn Lys Ile Arg Thr Leu
1               5                   10                  15

Gln Glu Glu Leu Gln Lys Arg Arg Glu Ser Leu Ala Ser Asn Pro Leu
            20                  25                  30

Trp Thr Gly Leu Gln Gly Phe Leu Pro Trp Phe Thr Thr Leu Ile Ser
        35                  40                  45

Thr Ile Met Gly Pro Leu Ile Val Leu Leu Ile Leu Leu Phe Gly
    50                  55                  60

Pro Cys Ile Leu Lys Asn Arg Leu Val Gln Phe Val Lys Asp Arg Ile
65                  70                  75                  80

Ser Val Val Gln Ala Leu Val Leu Thr Gln Gln Tyr Asx Gln Leu Lys
                85                  90                  95

Pro Ile Glu Tyr Glu Pro
            100

<210> SEQ ID NO 38
<211> LENGTH: 81
<212> TYPE: PRT
<213> ORGANISM: Chimaera sp.

<400> SEQUENCE: 38

Phe Tyr Ala Asn Lys Ser Gly Ile Val Arg Asn Lys Ile Arg Thr Leu
1               5                   10                  15

Gln Glu Glu Leu Gln Lys Arg Arg Glu Ser Leu Ala Ser Asn Pro Leu
            20                  25                  30

Trp Thr Gly Leu Gln Gly Phe Leu Pro Tyr Leu Leu Pro Leu Leu Gly
        35                  40                  45

Pro Leu Leu Thr Leu Leu Leu Ile Leu Thr Ile Gly Pro Cys Val Phe
    50                  55                  60

Ser Arg Leu Met Ala Phe Ile Asn Asp Arg Leu Asn Val Val His Ala
65                  70                  75                  80

Met

<210> SEQ ID NO 39
<211> LENGTH: 98
<212> TYPE: PRT
<213> ORGANISM: Chimaera sp.

<400> SEQUENCE: 39

Phe Tyr Ala Asn Lys Ser Gly Ile Val Arg Asn Lys Ile Arg Thr Leu
1               5                   10                  15

Gln Glu Glu Leu Gln Lys Arg Arg Glu Ser Leu Ala Ser Asn Pro Leu
            20                  25                  30

Trp Thr Gly Leu Gln Gly Phe Leu Pro Tyr Leu Leu Pro Leu Leu Gly
        35                  40                  45

Pro Leu Leu Thr Leu Leu Leu Ile Leu Thr Ile Gly Pro Cys Val Phe
    50                  55                  60

Ser Arg Leu Met Ala Phe Ile Asn Asp Arg Leu Asn Val Val Gln Ala
65                  70                  75                  80

Leu Val Leu Thr Gln Gln Tyr Gln Ala Leu Lys Ala Glu Glu Glu Ala
                85                  90                  95

Gln Asp

<210> SEQ ID NO 40
<211> LENGTH: 98
<212> TYPE: PRT
<213> ORGANISM: Chimaera sp.

<400> SEQUENCE: 40

Phe Tyr Ala Asn Lys Ser Gly Ile Val Arg Asn Lys Ile Arg Thr Leu
1               5                   10                  15

Gln Glu Glu Leu Gln Lys Arg Arg Glu Ser Leu Ala Ser Asn Pro Leu
            20                  25                  30

Trp Thr Gly Leu Gln Gly Phe Leu Pro Tyr Leu Leu Pro Leu Leu Gly
        35                  40                  45

Pro Leu Leu Thr Leu Leu Leu Ile Leu Thr Ile Gly Pro Cys Val Phe
    50                  55                  60

Ser Arg Leu Met Ala Phe Ile Asn Asp Arg Leu Asn Val Ala Arg Leu
65                  70                  75                  80

Met Ala Glu Ala Leu Gln Tyr Gln Ala Leu Lys Ala Glu Glu Glu Ala
                85                  90                  95

Gln Asp

<210> SEQ ID NO 41
<211> LENGTH: 98
<212> TYPE: PRT
<213> ORGANISM: Chimaera sp.

<400> SEQUENCE: 41

Phe Tyr Ala Asn Lys Ser Gly Ile Val Arg Asn Lys Ile Arg Thr Leu
1               5                   10                  15

Gln Glu Glu Leu Gln Lys Arg Arg Glu Ser Leu Ala Ser Asn Pro Leu
            20                  25                  30

Trp Thr Gly Leu Gln Gly Phe Leu Pro Tyr Leu Leu Pro Leu Leu Gly
        35                  40                  45

Pro Leu Leu Thr Leu Leu Leu Ile Leu Thr Ile Gly Pro Cys Val Phe
    50                  55                  60

Ser Arg Leu Met Ala Phe Ile Asn Asp Arg Leu Asn Val Arg Gln Ala
65                  70                  75                  80

Gly Phe Leu Gly Leu Gln Tyr Gln Ala Leu Lys Ala Glu Glu Glu Ala
                85                  90                  95

Gln Asp

<210> SEQ ID NO 42
<211> LENGTH: 98
<212> TYPE: PRT
<213> ORGANISM: Chimaera sp.

<400> SEQUENCE: 42

Phe Tyr Ala Asn Lys Ser Gly Ile Val Arg Asn Lys Ile Arg Thr Leu
1               5                   10                  15

Gln Glu Glu Leu Gln Lys Arg Arg Glu Ser Leu Ala Ser Asn Pro Leu
            20                  25                  30

Trp Thr Gly Leu Gln Gly Phe Leu Pro Tyr Leu Leu Pro Leu Leu Gly
        35                  40                  45

Pro Leu Leu Thr Leu Leu Leu Ile Leu Thr Ile Gly Pro Cys Val Phe
    50                  55                  60

Ser Arg Leu Met Ala Phe Ile Asn Asp Arg Leu Asn Val Ser Gln Asn

-continued

```
                 65                  70                  75                  80
Tyr Pro Ile Val Gln Gln Tyr Gln Ala Leu Lys Ala Glu Glu Glu Ala
                    85                  90                  95

Gln Asp

<210> SEQ ID NO 43
<211> LENGTH: 98
<212> TYPE: PRT
<213> ORGANISM: Chimaera sp.

<400> SEQUENCE: 43

Phe Tyr Ala Asn Lys Ser Gly Ile Val Arg Asn Lys Ile Arg Thr Leu
  1               5                  10                  15

Gln Glu Glu Leu Gln Lys Arg Arg Glu Ser Leu Ala Ser Asn Pro Leu
                 20                  25                  30

Trp Thr Gly Leu Gln Gly Phe Leu Pro Tyr Leu Leu Pro Leu Leu Gly
                 35                  40                  45

Pro Leu Leu Thr Leu Leu Ile Leu Thr Ile Gly Pro Cys Val Phe
         50                  55                  60

Ser Arg Leu Met Ala Phe Ile Asn Asp Arg Leu Asn Val Val His Ala
 65                  70                  75                  80

Met Val Leu Ala Gln Gln Ala Gln Ala Leu Lys Ala Glu Glu Glu Ala
                    85                  90                  95

Gln Asp
```